(12) United States Patent
Orinski

(10) Patent No.: US 8,332,052 B1
(45) Date of Patent: *Dec. 11, 2012

(54) MICROCIRCUIT COCHLEAR ELECTRODE ARRAY AND METHOD OF MANUFACTURE

(75) Inventor: William G. Orinski, Reno, NV (US)

(73) Assignee: Advanced Bionics, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/727,160

(22) Filed: Mar. 18, 2010

(51) Int. Cl.
*A61N 1/00* (2006.01)

(52) U.S. Cl. .............................. 607/137; 607/56; 607/57

(58) Field of Classification Search .................. 607/137, 607/57, 56; 128/898
See application file for complete search history.

(56) References Cited

U.S. PATENT DOCUMENTS

| | | | |
|---|---|---|---|
| 4,031,310 A | 6/1977 | Jachimowicz | |
| 4,261,372 A | 4/1981 | Hansen et al. | |
| 4,284,085 A | 8/1981 | Hansen et al. | |
| 4,762,135 A | 8/1988 | van der Puije et al. | |
| 4,832,051 A | 5/1989 | Jarvik et al. | |
| 5,580,699 A | 12/1996 | Layman et al. | |
| 5,658,709 A | 8/1997 | Layman et al. | |
| 5,720,099 A | 2/1998 | Parker et al. | |
| 5,987,361 A | 11/1999 | Mortimer | |
| 6,309,410 B1 | 10/2001 | Kuzma et al. | |
| 6,355,401 B1 | 3/2002 | Graves et al. | |
| 6,374,143 B1 | 4/2002 | Berrang et al. | |
| 6,421,569 B1 | 7/2002 | Treaba et al. | |
| 6,643,552 B2 | 11/2003 | Edell et al. | |
| 6,678,564 B2 | 1/2004 | Ketterl et al. | |
| 6,757,970 B1 | 7/2004 | Kuzma et al. | |
| 6,779,257 B2 | 8/2004 | Kiepen et al. | |
| 6,782,619 B2 | 8/2004 | Corbett et al. | |
| 6,843,870 B1 | 1/2005 | Bluger | |
| 6,974,533 B2 | 12/2005 | Zhou | |
| 7,047,081 B2 | 5/2006 | Kuzma | |

(Continued)

FOREIGN PATENT DOCUMENTS

AU    2004000903484    6/2004

(Continued)

OTHER PUBLICATIONS

Rodger et al., Flexible parylene-based multielectrode array technology for high-density neural stimulation and recording, Sensors and Actuators B 132 (2008) 449-460.

(Continued)

*Primary Examiner* — Niketa Patel
*Assistant Examiner* — Alyssa M Alter
(74) *Attorney, Agent, or Firm* — Steven L. Nichols; Van Cott, Bagley, Cornwall & McCarthy P.C.

(57) ABSTRACT

A microcircuit cochlear electrode array and process for the manufacture thereof, the electrode array comprising first and second flat microcircuits comprising a plurality of laterally spaced longitudinally extending electrical conductors and longitudinally spaced electrode receiving pads extending laterally from the conductors, the first flat microcircuit being helically wrapped in a first direction along an axis with its longitudinally spaced electrode receiving pads exposed on an end of an outer surface hereof and the second flat microcircuit helically being wrapped in an opposite direction on and along an outer surface of the first helically wrapped microcircuit with its longitudinally spaced electrode receiving pads exposed on an outer surface thereof adjacent the exposed longitudinally spaced electrode receiving pads of the first microcircuit, and ring electrodes around and electrically secured to the electrode receiving pads of the first and second microcircuits.

18 Claims, 56 Drawing Sheets

U.S. PATENT DOCUMENTS

| | | |
|---|---|---|
| 7,067,765 B2 | 6/2006 | Bauer et al. |
| 7,085,605 B2 | 8/2006 | Bluger et al. |
| 7,142,909 B2 | 11/2006 | Greenberg et al. |
| 7,240,416 B2 | 7/2007 | Milojevic et al. |
| 7,326,649 B2 | 2/2008 | Rodger et al. |
| 7,406,352 B2 | 7/2008 | Gibson |
| 7,587,248 B2 | 9/2009 | Risi et al. |
| 7,774,071 B2 | 8/2010 | Schuller |
| 7,970,481 B2 | 6/2011 | Milojevic et al. |
| 2003/0097165 A1 | 5/2003 | Krulevitch et al. |
| 2003/0236562 A1 | 12/2003 | Kuzma |
| 2004/0015221 A1 | 1/2004 | Kuzma |
| 2004/0020686 A1 | 2/2004 | Alfonso Perez et al. |
| 2004/0147825 A1 * | 7/2004 | Milojevic et al. ............ 600/372 |
| 2004/0147992 A1 | 7/2004 | Bluger et al. |
| 2004/0172118 A1 | 9/2004 | Gibson |
| 2004/0256146 A1 | 12/2004 | Frericks et al. |
| 2005/0016657 A1 | 1/2005 | Bluger |
| 2005/0107858 A1 | 5/2005 | Bluger |
| 2005/0256561 A1 | 11/2005 | Gantz et al. |
| 2006/0003090 A1 | 1/2006 | Rodger et al. |
| 2006/0089700 A1 | 4/2006 | Darley |
| 2006/0095105 A1 | 5/2006 | Jog et al. |
| 2006/0206185 A1 | 9/2006 | Schuller |
| 2006/0236532 A1 | 10/2006 | Schuller |
| 2006/0247754 A1 | 11/2006 | Greenberg et al. |
| 2006/0255293 A1 | 11/2006 | Tai et al. |
| 2006/0259112 A1 | 11/2006 | Greenberg et al. |
| 2007/0123963 A1 | 5/2007 | Krulevitch |
| 2007/0168004 A1 | 7/2007 | Walter |
| 2007/0293749 A1 | 12/2007 | Zhou et al. |
| 2008/0027525 A1 | 1/2008 | Frericks et al. |
| 2008/0044591 A1 | 2/2008 | Laude et al. |
| 2008/0140156 A1 | 6/2008 | Rodriguez et al. |
| 2008/0262584 A1 | 10/2008 | Bottomley et al. |
| 2009/0043358 A1 | 2/2009 | Dadd et al. |
| 2009/0143848 A1 | 6/2009 | Greenberg et al. |
| 2009/0165921 A1 | 7/2009 | Kaiser |
| 2009/0229739 A1 | 9/2009 | Schuller |
| 2010/0023102 A1 | 1/2010 | Spruit |
| 2010/0287762 A1 | 11/2010 | Milojevic et al. |
| 2010/0305673 A1 | 12/2010 | Jolly et al. |
| 2011/0098719 A1 | 4/2011 | Llinas et al. |
| 2011/0180305 A1 | 7/2011 | Johnson et al. |
| 2012/0004715 A1 | 1/2012 | Ramachandran et al. |

FOREIGN PATENT DOCUMENTS

| | | | |
|---|---|---|---|
| EP | 0002068 A2 | 5/1979 | |
| EP | 0007157 A2 | 1/1980 | |
| EP | 0007157 A3 | 8/1980 | |
| EP | 1574181 A1 | 9/2005 | |
| EP | 0888701 B1 | 10/2007 | |
| EP | 2046443 A1 | 4/2009 | |
| EP | 2066397 B1 | 2/2010 | |
| EP | 1587454 B1 | 4/2010 | |
| EP | 1574181 B1 | 10/2010 | |
| EP | 2286871 A2 | 2/2011 | |
| EP | 2298408 A2 | 3/2011 | |
| EP | 1651305 B1 | 8/2011 | |
| WO | 9706760 A1 | 2/1997 | |
| WO | 9728668 A1 | 8/1997 | |
| WO | 02078575 A1 | 10/2002 | |
| WO | 02089907 A1 | 11/2002 | |
| WO | 03017329 A2 | 2/2003 | |
| WO | 03017329 A3 | 2/2003 | |
| WO | 03049638 A2 | 6/2003 | |
| WO | 03049638 A3 | 6/2003 | |
| WO | 03090848 A1 | 11/2003 | |
| WO | 2004035133 A1 | 4/2004 | |
| WO | 2004054474 A1 | 7/2004 | |
| WO | 2004064687 A1 | 8/2004 | |
| WO | 2005004978 A1 | 1/2005 | |
| WO | 2006000031 A1 | 1/2006 | |
| WO | 2007065216 A2 | 6/2007 | |
| WO | 2007065216 A3 | 6/2007 | |
| WO | 2008011721 A1 | 1/2008 | |
| WO | 2008031144 A1 | 3/2008 | |
| WO | 2009062114 A2 | 5/2009 | |
| WO | 2009062114 A3 | 5/2009 | |
| WO | 2009065127 A1 | 5/2009 | |
| WO | 2009065171 A1 | 5/2009 | |
| WO | 2010055421 A1 | 5/2010 | |
| WO | 2010079875 A1 | 7/2010 | |
| WO | 2010138567 A2 | 12/2010 | |
| WO | 2012003295 A1 | 1/2012 | |
| WO | 2012003297 A1 | 1/2012 | |

OTHER PUBLICATIONS

Henle et al, Scaling Limitations of Laser-Fabricated Nerve Electrode Arrays; 30th Annual International IEEE EMBS Conference; Aug. 20-24, 2008; pp. 4208-4211; Vancouver, British Columbia, Canada.

Schuettler et al, Fabrication of Implantable Microelectrode Arrays by Laser Cutting of Silicone Rubber and Platinum Foil, Institute of Physics Publishing; Journal of Neural Engineering; Feb. 22, 2005, pp. S121-S128; United Kingdom.

Schuettler et al, Fabricating microelectrode arrays by laser-cutting of platinum foil and silicone rubber, 9th Annual conference of the International FES Society, Sep. 2004, pp. 1-3, Bournemouth, UK.

* cited by examiner

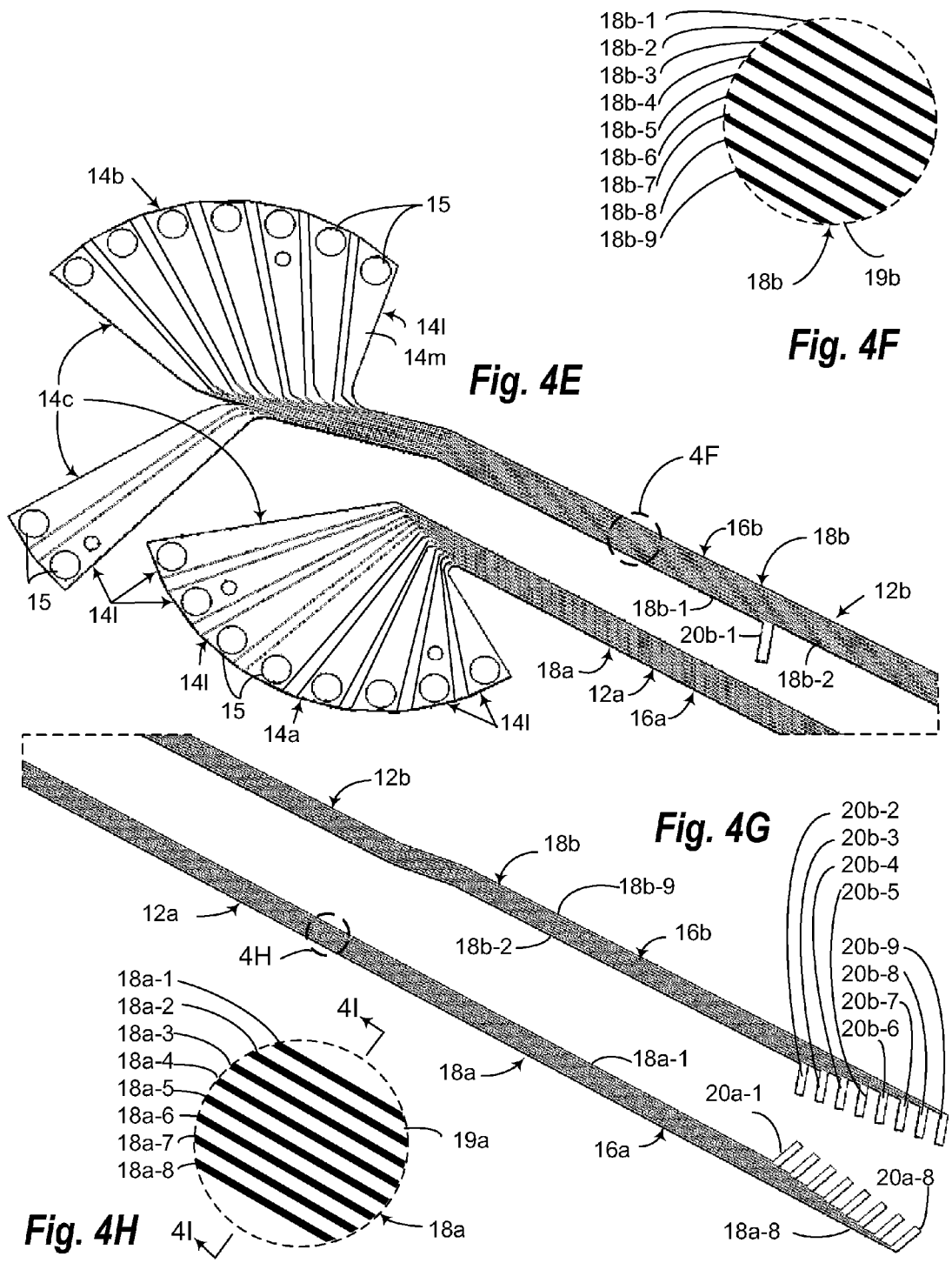

MICROCIRCUIT COCHLEAR ELECTRODE ARRAY AND METHOD OF MANUFACTURE

INCORPORATION BY REFERENCE

U.S. patent application Ser. No. 12/338,758, filed Dec. 18, 2008, and U.S. Provisional Patent Application Ser. No. 61/023,389, filed Jan. 24, 2008, are incorporated herein by reference in their entireties.

BACKGROUND OF INVENTION

Current procedures for manufacturing cochlear electrodes involve operator intervention throughout the manufacturing process wherein the electrodes are manually formed and handled. This results in relatively slow processing of the electrodes and subjects the electrodes to undesired mechanical stresses and breakage.

It is an object of the present invention to provide a more compact and robust cochlear electrode design and a more rapid process of manufacture that reduces operator intervention, reduces material waste and rework of the electrodes, and increases the throughput and efficiency of electrode manufacture.

SUMMARY OF INVENTION

The present invention is directed to microcircuit cochlear electrode arrays and processes for manufacturing the electrode arrays. In describing the electrode arrays and their processes of manufacture, the terms "ring electrode" and "overmolding" will be employed. As used herein, the term "ring electrode" is intended to include both circumferentially closed and circumferentially open conductive rings dimensioned to receive and be supported by and electrically connected to the electrode receiving pads on the exposed outer surface of flat, helically wrapped multiconductor tail portions of the electrode arrays. Also, as used herein, the term "overmolded" as applied to the ring electrodes is intended to encompass all known molding processes and procedures employed in applying a suitable polymeric material to cochlear electrodes to support and/or isolate them, including, without limitation, the masking of portions of such electrodes followed by a removal of the masking material to expose portions of the electrode after applying the polymeric material, the use of molding equipment including internal features that block the flow of the polymeric material to portions of the electrode leaving the electrode with exposed portions, and the use of polymeric material removal apparatus such as lasers to remove some of the polymeric material to expose portions of the electrode.

Basically, the cochlear electrode arrays of the present invention comprise first and second flat microcircuits each having associated head and tail portions. Each tail portion contains a plurality of laterally spaced longitudinally extending electrical conductors of progressively longer length covered with an insulating material and each having an exposed electrode receiving pad extending forward at an acute angle from an end portion of its associated electrical conductor. The head portions of the microcircuits each contain laterally spaced and exposed circuit attachment pads each electrically connected to a different one of the electrical conductors contained in its associated tail portion. The tail portion of the first flat microcircuit is helically wrapped on a longitudinal axis in a first direction (e.g. clockwise) with its electrode receiving pads spaced longitudinally and extending around the insulation covering the electrical conductors of the first microcircuit. Thus arranged, the electrode receiving pads of the first microcircuit define a first series of longitudinally spaced exposed electrode receiving pads. A forwardmost pad of the first series is adjacent a forward end of the helically wrapped tail portion of the first microcircuit with the remainder of the pads comprising the first series being longitudinally spaced rearward from the forwardmost pad. The tail portion of the second flat microcircuit also is helically wrapped but in a direction opposite to the first direction (e.g. counterclockwise) and is helically wrapped over the helically wrapped tail portion of the first microcircuit with its longitudinally spaced electrode receiving pads extending around the insulation covering the electrical conductors of the second microcircuit. Wrapping the first and second microcircuits in different directions counterbalances the forces within the lead. Thus arranged, the electrode receiving pads of the second microcircuit define a second series of longitudinally spaced exposed electrode receiving pads, a forwardmost pad of the second series being located adjacent the rearmost electrode receiving pad of the first series and a remainder of the electrode receiving pads of the second series being spaced longitudinally rearward from the forwardmost pad. Also, a rearmost electrode receiving pad of second flat microcircuit is longitudinally separated rearward from the second series of pads to define a reference or ground electrode receiving pad for the cochlear electrode array. Finally, the cochlear electrode array of the present invention comprises ring electrodes located on and electrically connected to each of the longitudinally spaced electrode receiving pads of the tail portions of the first and second microcircuits and the helically wrapped tail portions of the first and second microcircuits are overmolded with a suitable polymeric insulating material.

In a first preferred embodiment of the cochlear electrode array of the present invention, a forwardmost end portion of the helically wrapped tail portions of the cochlear electrode array is shaped in a "J" configuration prior to its final overmolding. In a second preferred embodiment of the cochlear electrode array of the present invention, the forwardmost end portion of the helically wrapped tail portions of the cochlear electrode array is shaped as an inward spiral having a laterally offset stylet-receiving lumen prior to its final overmolding. As described herein, the spiral may be planar; alternatively, as one skilled in the art would appreciate, the spiral may be a three-dimensional helix.

Basically, the process for manufacturing the microcircuit cochlear electrode arrays comprise the steps of securing and supporting a nonconductive film substrate, attaching a metallic ribbon to a surface of the substrate and machining first and second flat multiconductor microcircuits from the ribbon, each including an associated head portion and tail portion. Each tail portion is machined to contain a plurality of laterally spaced longitudinally extending electrical conductors of progressively longer length, each having an exposed flat electrode receiving pad extending laterally outward at a forward acute angle from an end portion of its associated electrical conductor. Each head portion is machined to contain spaced, exposed circuit attachment pads, each connected to a different one of the electrical conductors of its associated tail portion. The flat microcircuits are laminated between the substrate and an insulating cover preferably comprising a second nonconductive substrate. The laminated microcircuits are then excised from the film substrates with the attachment pads of the head portions exposed and bottom surfaces of the electrode receiving pads of the tail portions exposed as a first and a second series of separate longitudinally spaced laterally extending exposed ring electrode receiving pads. The head portions of the excised laminated microcircuits are then positioned adjacent each other and the tail portion of a first one of the excised microcircuits is helically wrapped on a longitudinal axis in a first direction (e.g. clockwise) with its exposed electrode receiving pads extending around its insulating cover as a first series of separate longitudinally spaced ring electrode receiving pads. The tail portion of a second one the excised microcircuits is then helically wrapped in an opposite direction (e.g. counterclockwise) on and along the helically wrapped tail portion of the first microcircuit with its exposed electrode receiving pads extending around its insulating cover as a second series of separate longitudinally spaced electrode receiving pads immediately adjacent the first series of electrode receiving pads. Finally, ring electrodes are mounted on and electrically connected to each of the exposed electrode receiving pads and the helically wrapped tail portions are overmolded with a suitable polymeric material readying the microcircuit electrode array for cochlear implant.

In the processes for forming both the first and second preferred embodiments of the cochlear electrode array of the present invention, (i.e. the J-style cochlear electrode array and spiral-style cochlear electrode array), a rearmost electrode receiving pad of the second microcircuit and the ring electrode positioned on and electrically connected thereto are spaced rearward of the second series of electrode receiving pads to define a reference or ground electrode for the associated cochlear electrode array. In the formation of the J-style cochlear electrode array, the manufacturing process is basically as previously described. In the formation of the spiral-style cochlear electrode array, however, a slightly modified process is employed to include the formation of a laterally spaced stylet lumen in the helically wrapped forward end portion of the cochlear electrode array. Basically, that process comprises two separate forward helical wrappings of the tail portions of the first and second flat microcircuits. The first separate helical wrapping comprises an initial helical wrapping of a portion of the tail portion of the first microcircuit adjacent its associated head portion. That initial helical wrapping is in the first direction (e.g. clockwise) on and around a first longitudinal axis and is immediately followed by an initial helical wrapping of the tail portion of the second microcircuit adjacent its head portion in an opposite direction (e.g. counterclockwise) on and around the initially wrapped tail portion of the first microcircuit. Such forward initial wrappings of the tail portions of the first and second microcircuits continue to a location forward of where the reference electrode receiving pad of the second microcircuit will be wrapped around the initially wrapped portion of the first microcircuit and rearward of the second series of electrode receiving pads of the tail portion of the second microcircuit. Once such initial wrappings of the tail portions of the first and second microcircuits have been completed, the reference ring electrode is mounted on and electrically connected to the exposed outer surface of the reference electrode receiving pad and the initially wrapped tail portions of the first and second microcircuits are overmolded with a suitable polymeric material. The second separate forward helical wrapping is then instituted comprising (i) a forward helical wrapping of the remainder of the tail portion of the first microcircuit in the first direction on and along a second longitudinal axis laterally spaced and offset from the first longitudinal axis with its laterally extending exposed electrode receiving pads extending around the insulating cover thereof to form the first series of longitudinally spaced exposed ring electrode receiving pads and (ii) a helical wrapping of the remainder of the tail portion of the second microcircuit in the second direction on and around the helically wrapped remainder of the first microcircuit with its laterally extending exposed electrode receiving pads extending around the insulating cover thereof to form the second series of longitudinally spaced ring electrode receiving pads. By laterally offsetting the helical wrapping of the remainders of the tail portions of the first and second microcircuits from the initial wrapping of the tail portions a longitudinally extending internal stylet lumen is formed within the helically wrapped remainders which with the helically wrapped remainders is shaped in the form of an inward spiral and overmolded to define the second preferred embodiment, or spiral-style cochlear electrode array, of the present invention.

BRIEF DESCRIPTION OF ACCOMPANYING DRAWINGS

FIGS. 2A-8H show the initial steps for manufacturing leads having either a J-shaped electrode array or a spiral-shaped electrode array.

FIGS. 2A-2E show the securing and support of a first nonconductive substrate pursuant to step 1 of the process of FIG. 1;

FIG. 2A shows a film substrate vacuum support apparatus utilized in the process steps of securing and supporting nonconductive film substrates;

FIG. 2B shows an open rectangular frame comprising a bottom carrier for supporting a nonconductive film substrate over the vacuum support apparatus of FIG. 2A;

FIG. 2C shows a length of nonconductive film substrate having a removable backing extending from a roll adjacent the vacuum support apparatus of FIG. 2A over the frame comprising the bottom carrier of FIG. 2B;

FIG. 2D shows an open rectangular frame comprising a top carrier over the length of film substrate after it has been lowered onto the lower frame on the film substrate vacuum support apparatus;

FIG. 2E shows the length of film substrate secured between the lower and upper frames of the carrier on the film substrate vacuum support apparatus with excess film removed and a metallic ribbon placed on an upper surface of the film substrate;

FIGS. 2F-FIG. 3C depict the securing of the metallic ribbon to the upper surface of the film substrate pursuant to step 2 of the process of FIG. 1;

FIG. 2F shows the carrier for the film substrate and metallic ribbon removed from the film substrate vacuum support apparatus of FIG. 2E;

FIG. 3C shows the carrier removed from the laminating press with the metallic ribbon bonded to the upper surface of the film substrate;

FIGS. 4A-4I depict the machining of first and second flat multi-conductor microcircuits pursuant to step 3 of the process of FIG. 1, each microcircuit having associated head and tail portions formed from the metallic ribbon secured to the upper surface of the film substrate;

FIG. 4A shows the carrier of FIG. 3C over a vacuum chuck for laser machining of the metallic ribbon;

FIG. 4B shows the carrier on the vacuum chuck of FIG. 4A;

Figure 1:
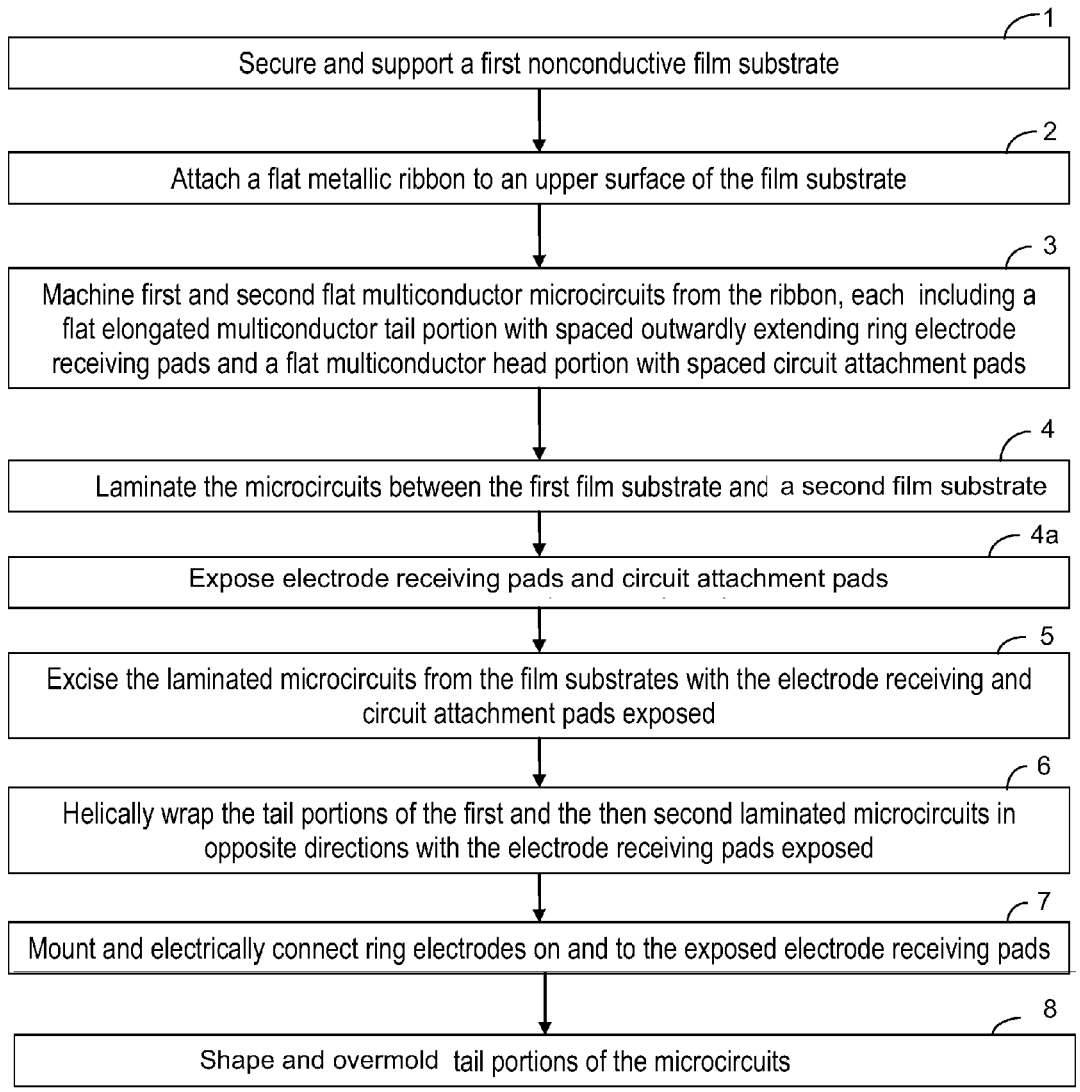
FIG. 1 is a flow chart of the basic steps central to the manufacturing processes of the present invention.
Figure 3A:
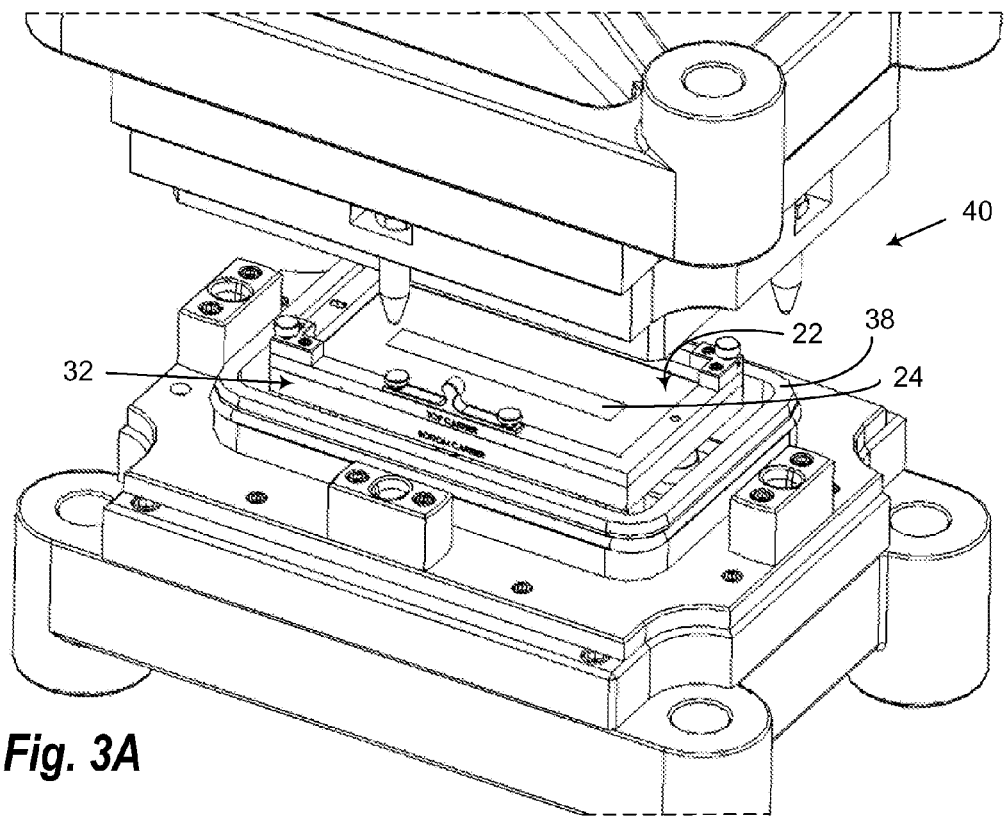
FIG. 3A shows the carrier, film substrate, and metallic ribbon of FIG. 2E on a lower open platen of a laminating press.
Figure 4A:
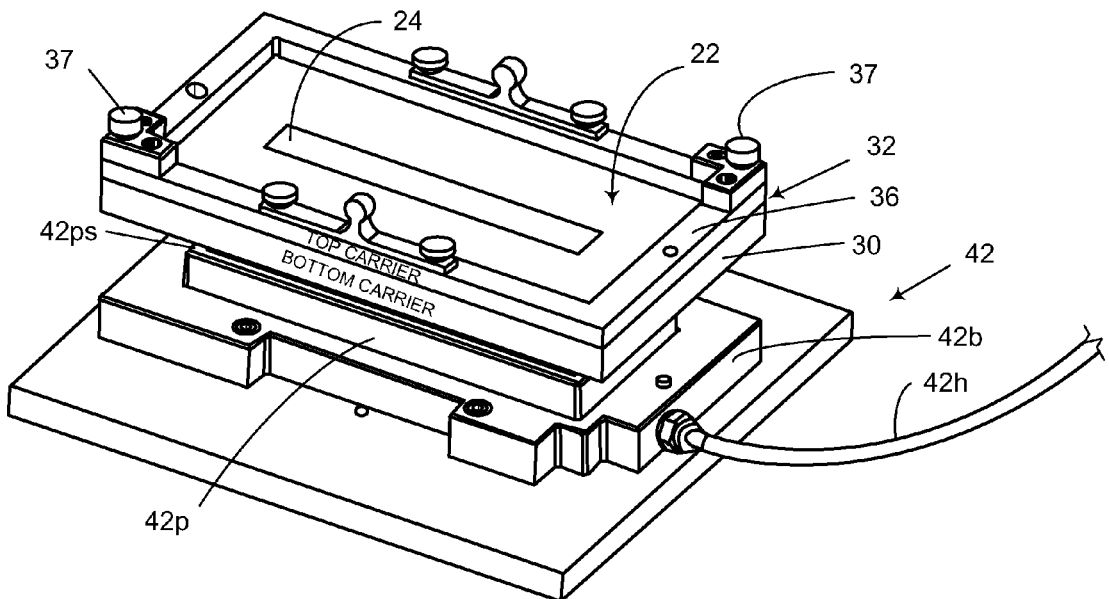
Figure 4B:
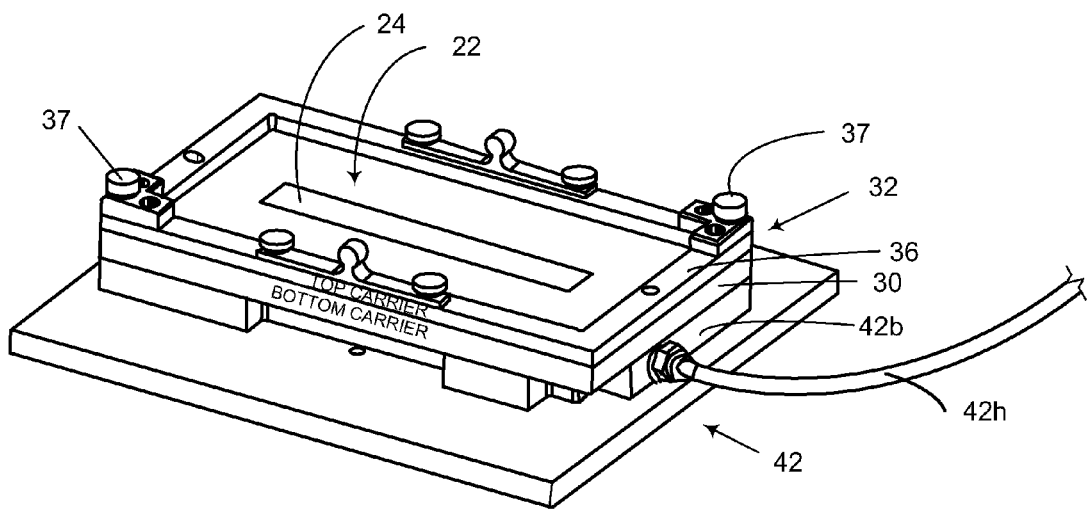
Figure 4C:
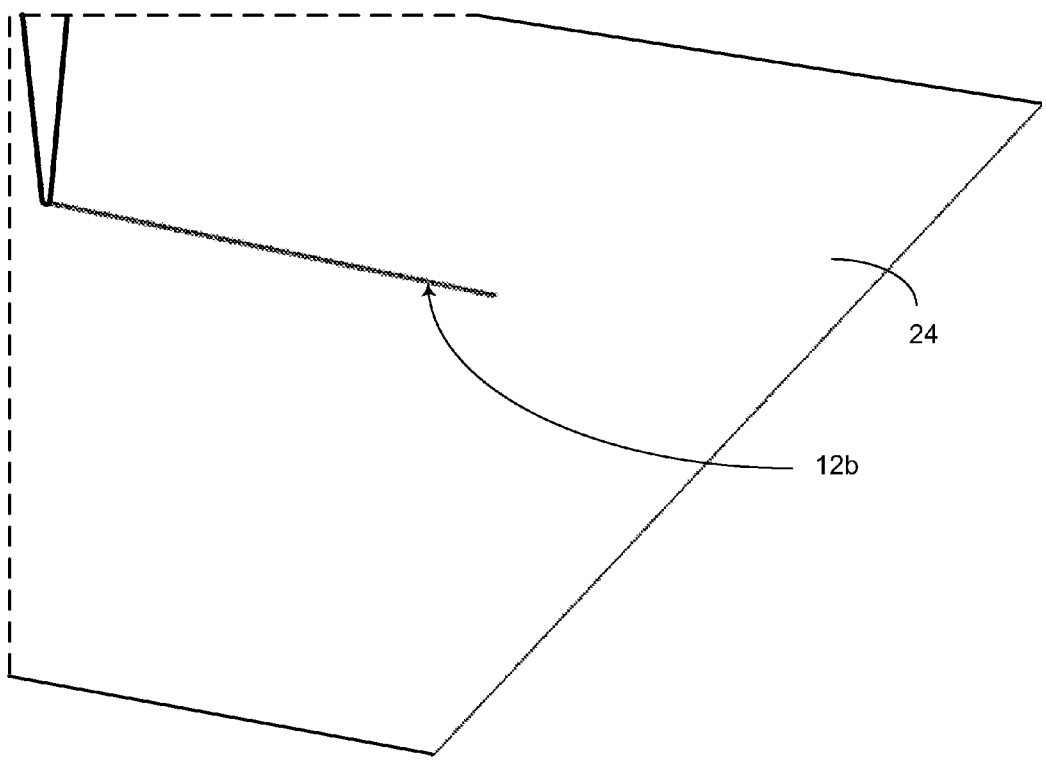
Figure 4D:
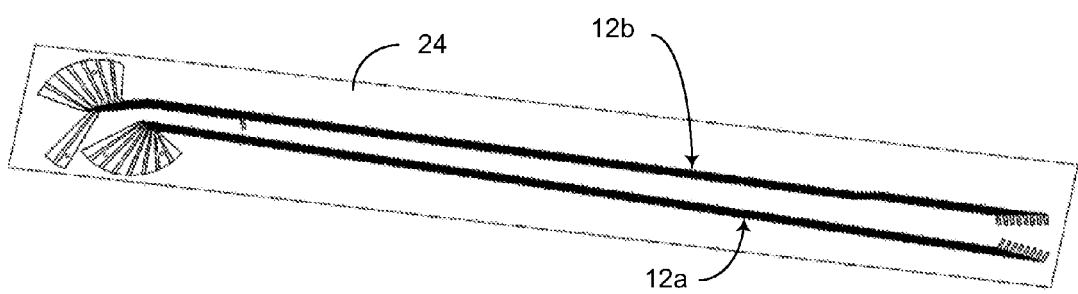
Figure 4L:
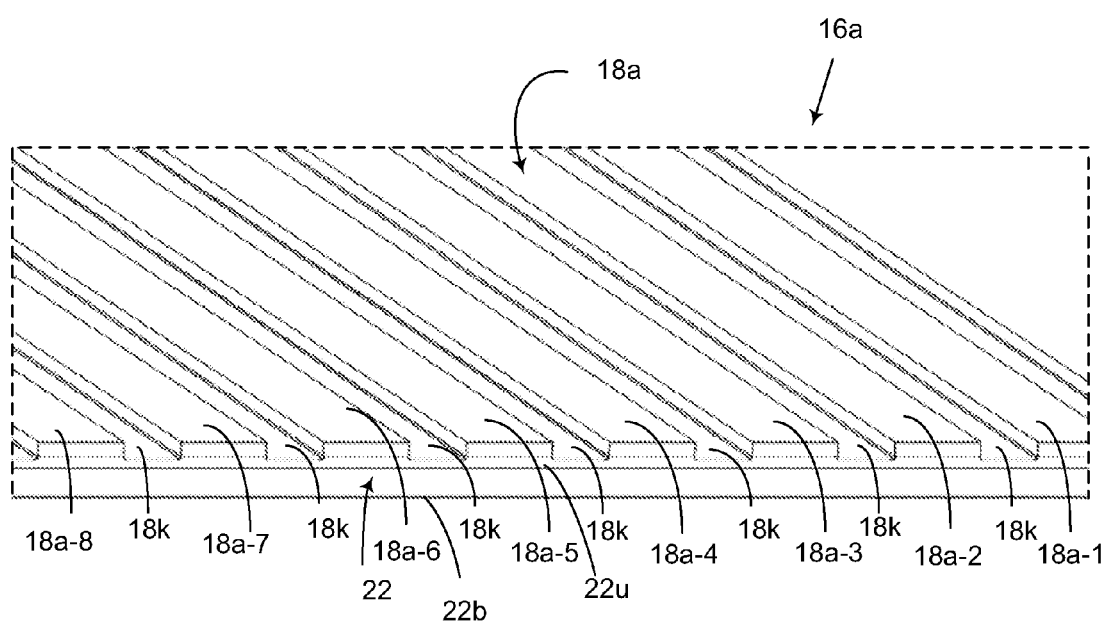
Figure 5A:
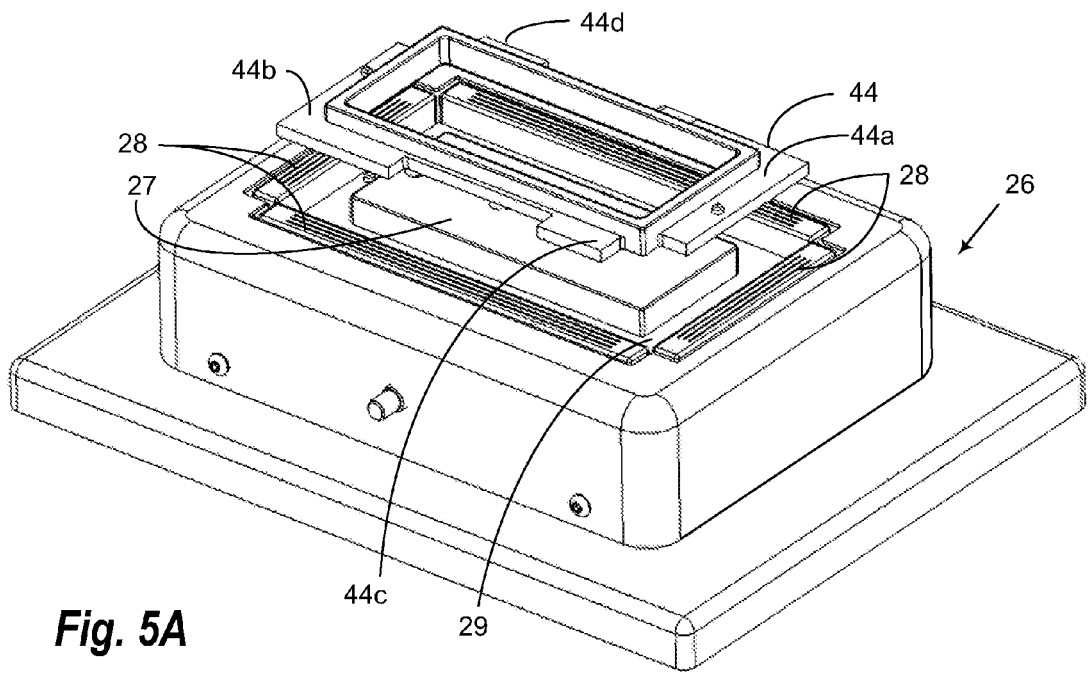
Figure 5B:
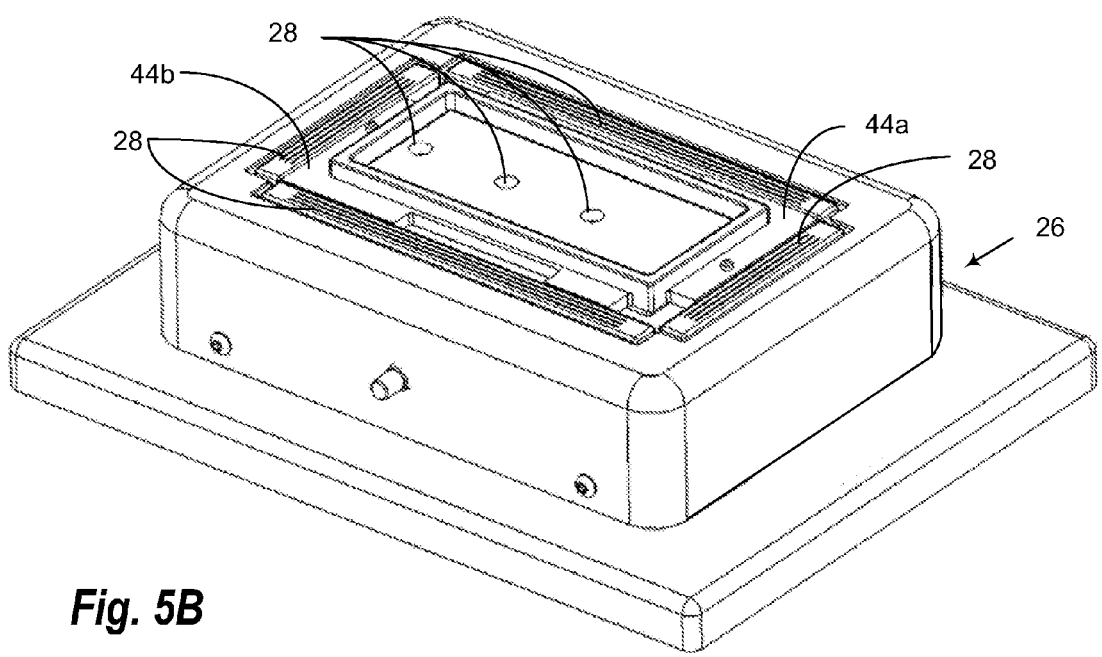
Figure 5C:
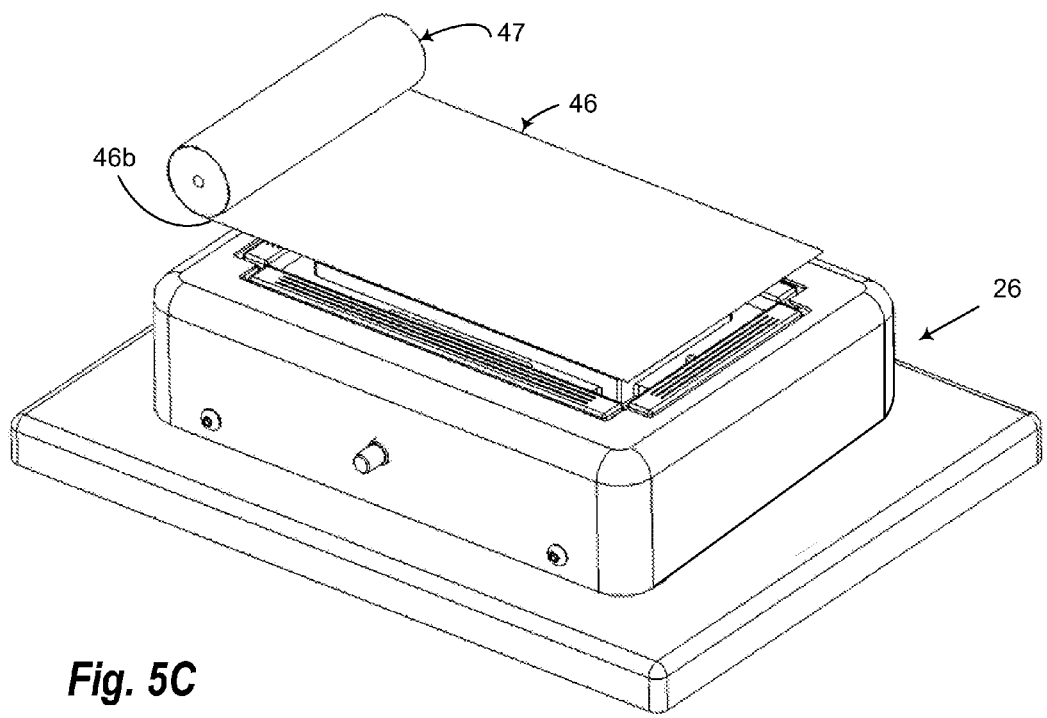
Figure 5D:
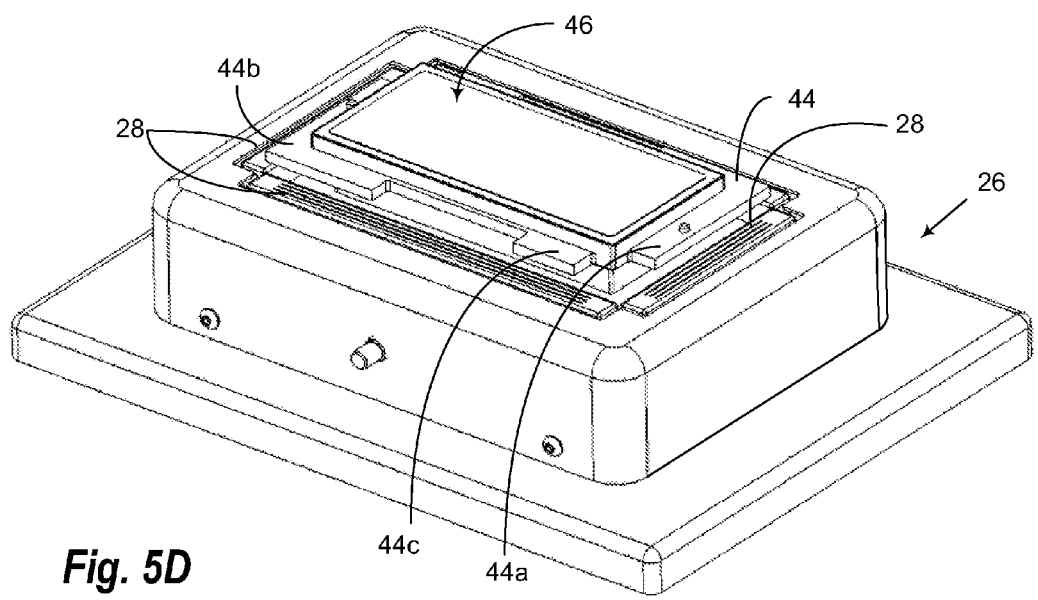
Figure 5E:
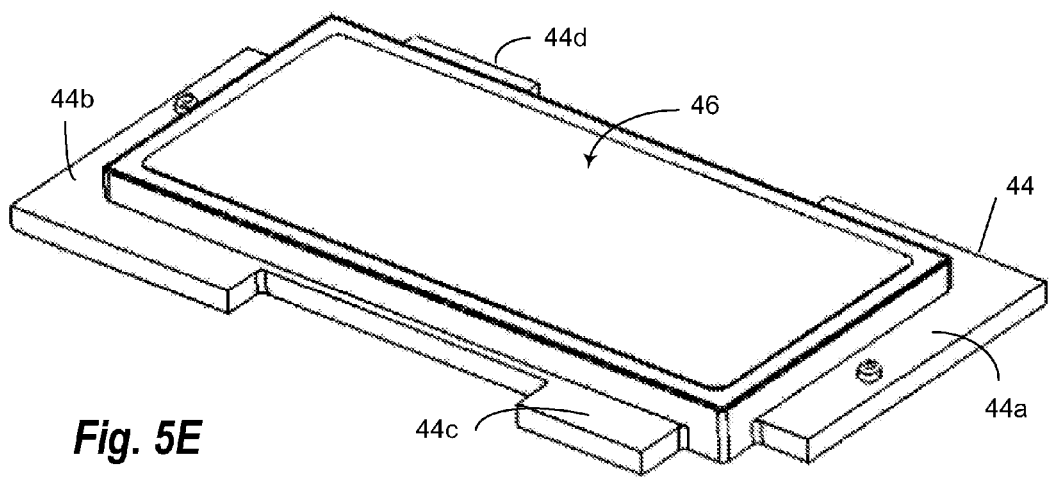
Figure 5F:
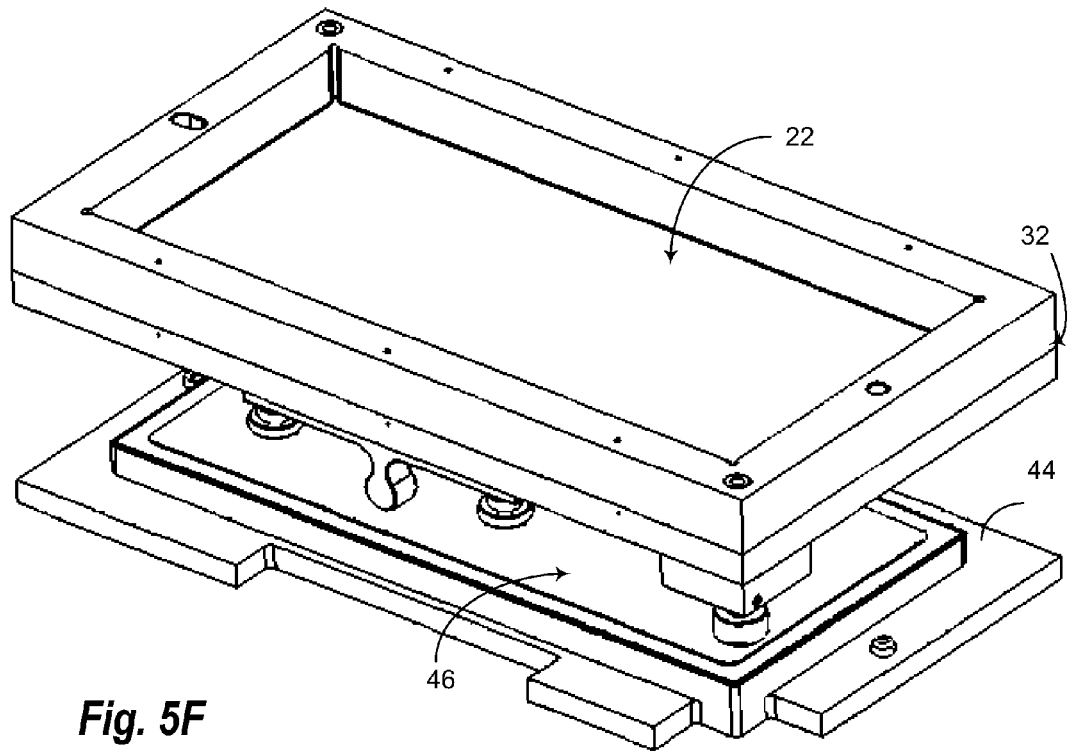
Figure 5G:
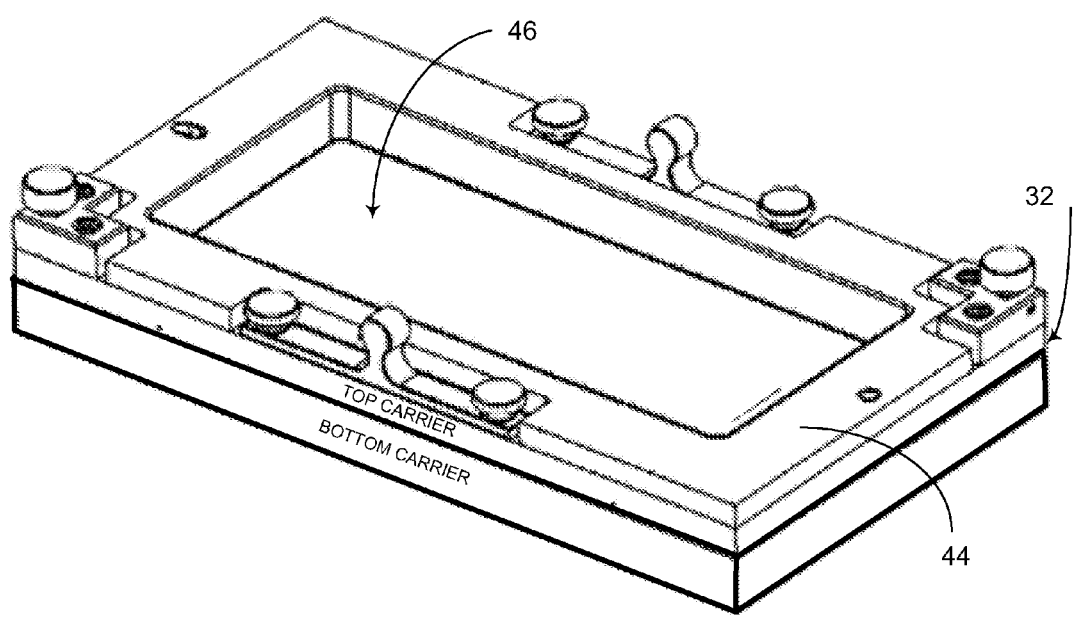
Figure 6A:
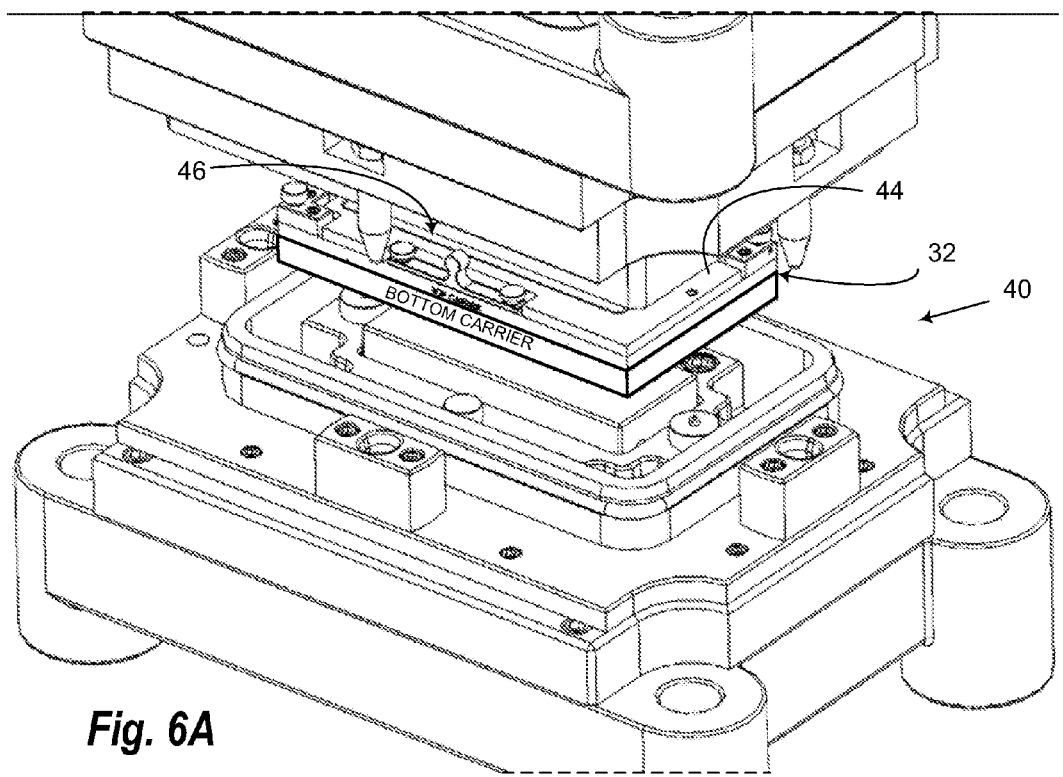
Figure 6B:
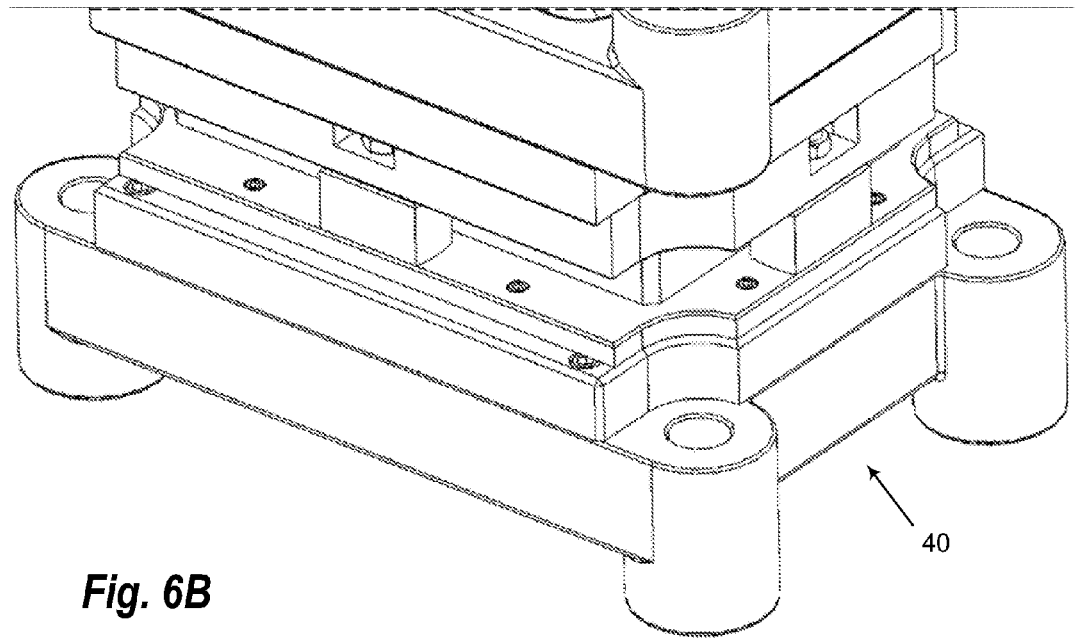
Figure 6C:
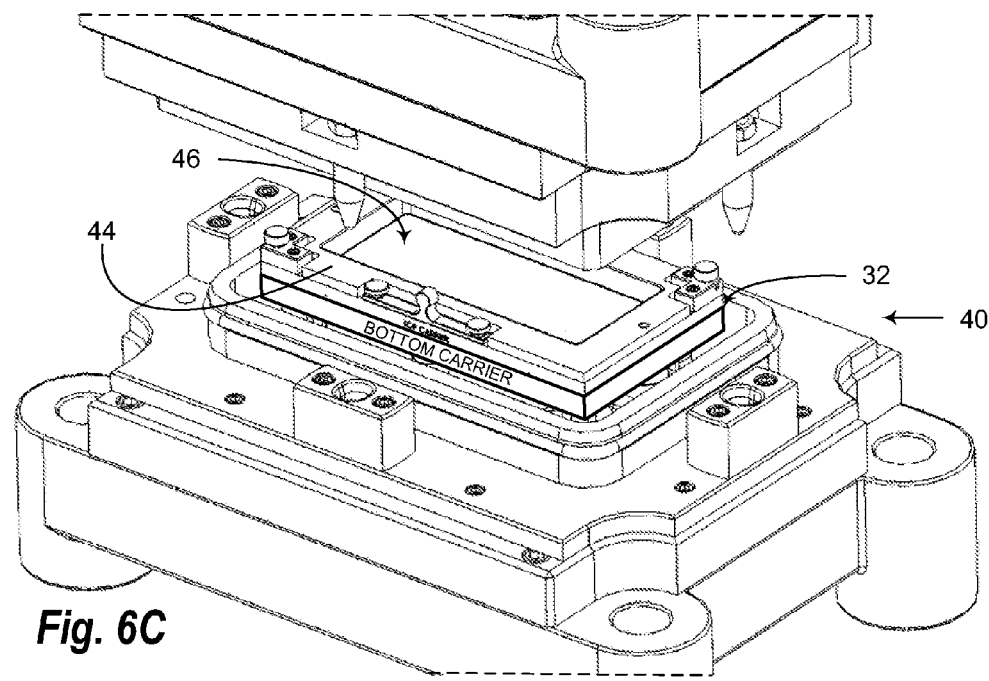
Figure 6D:
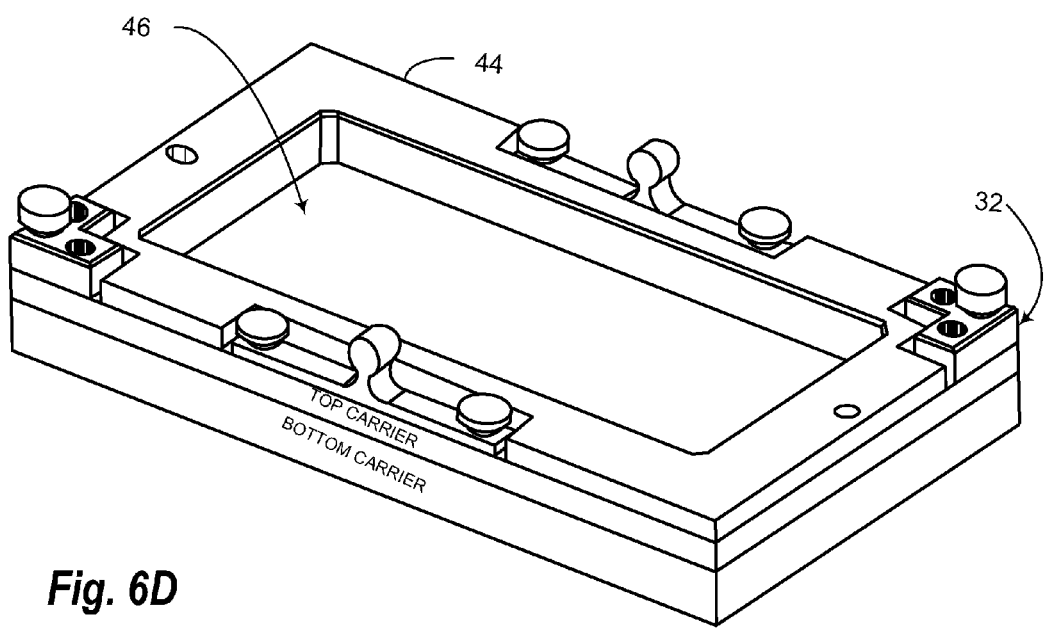
Figure 7A:
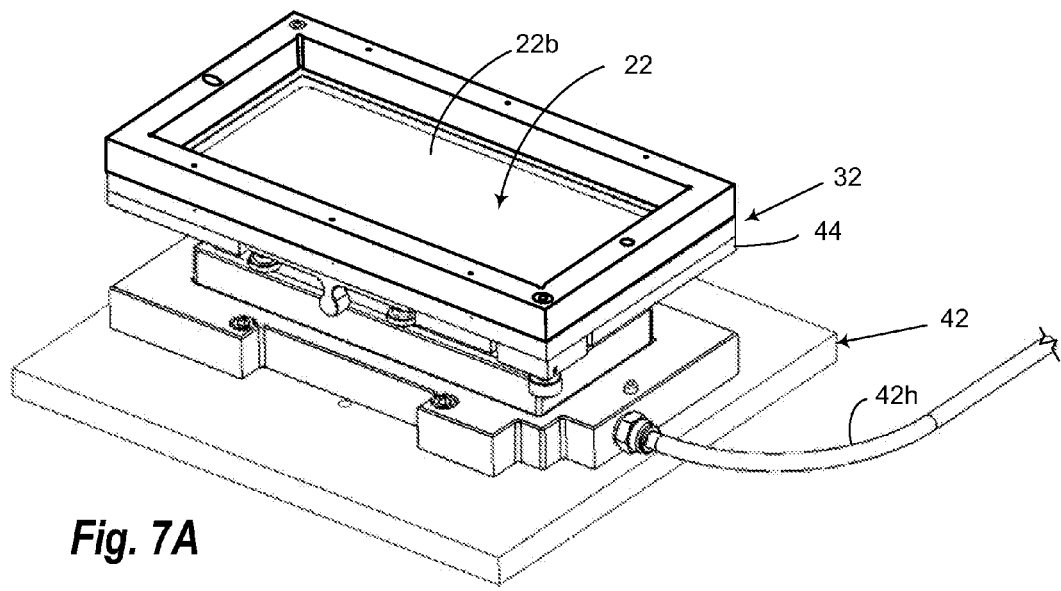
Figure 7B:
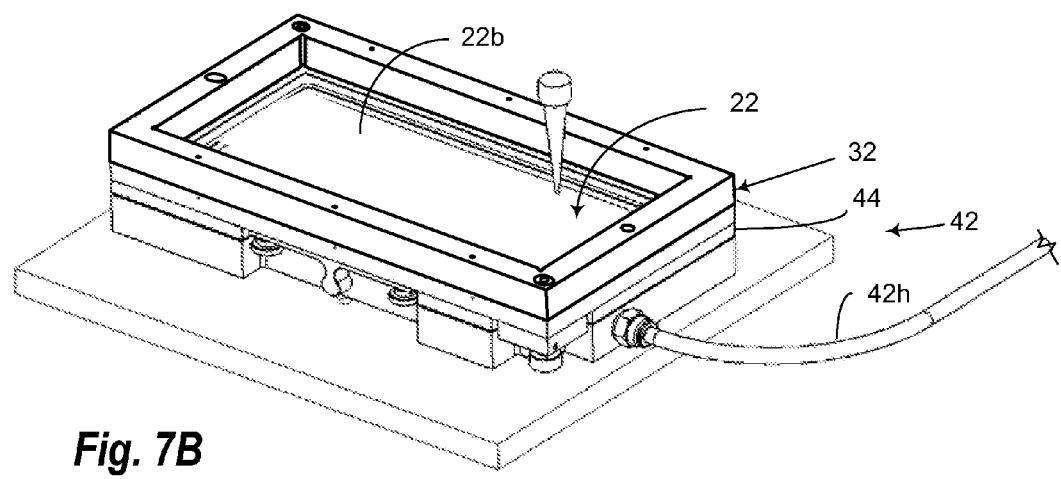
Figure 7C:
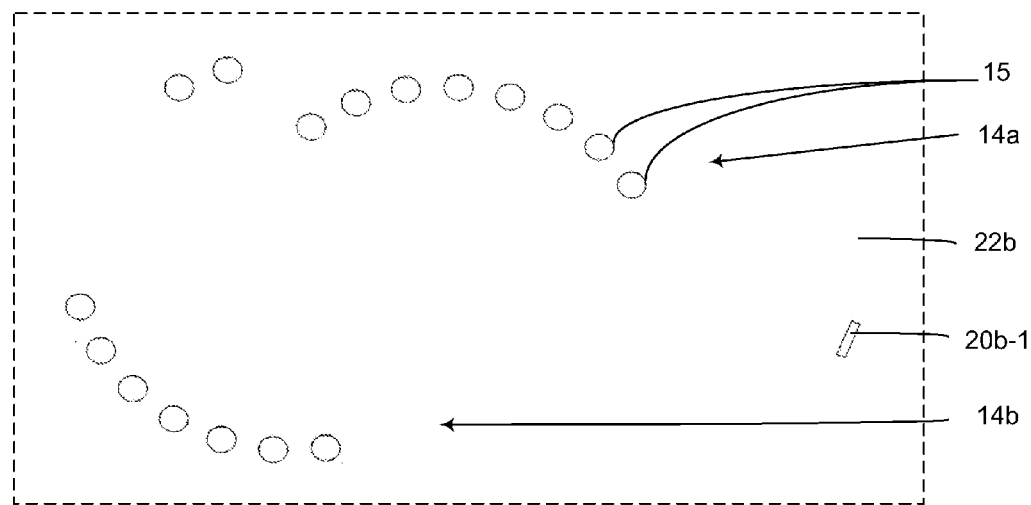
Figure 7D:
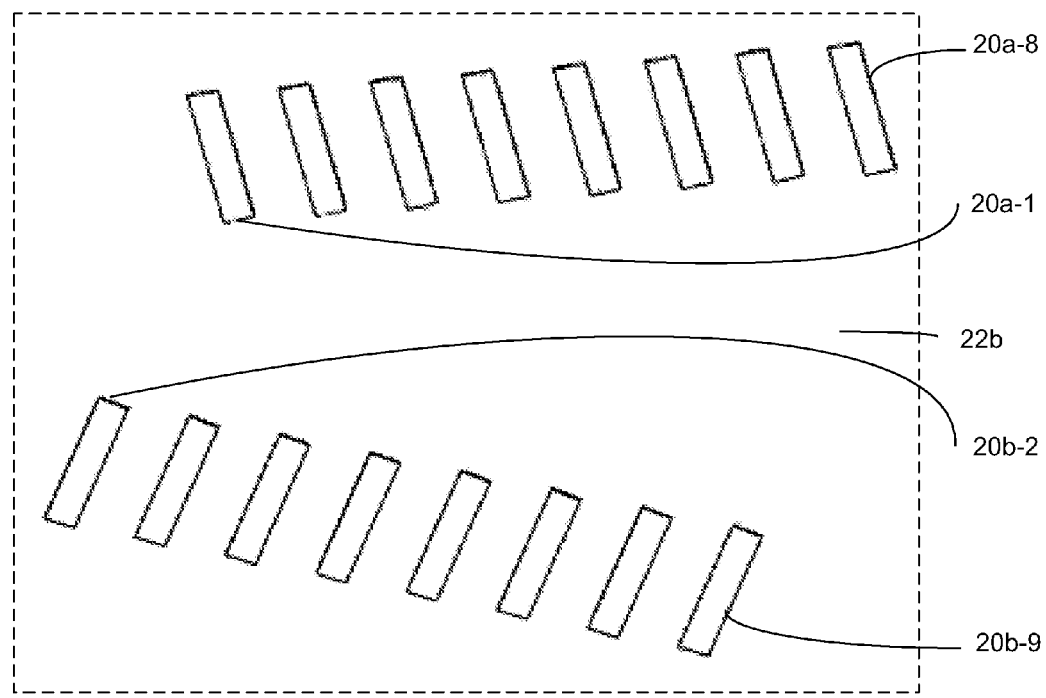
Figure 7E:
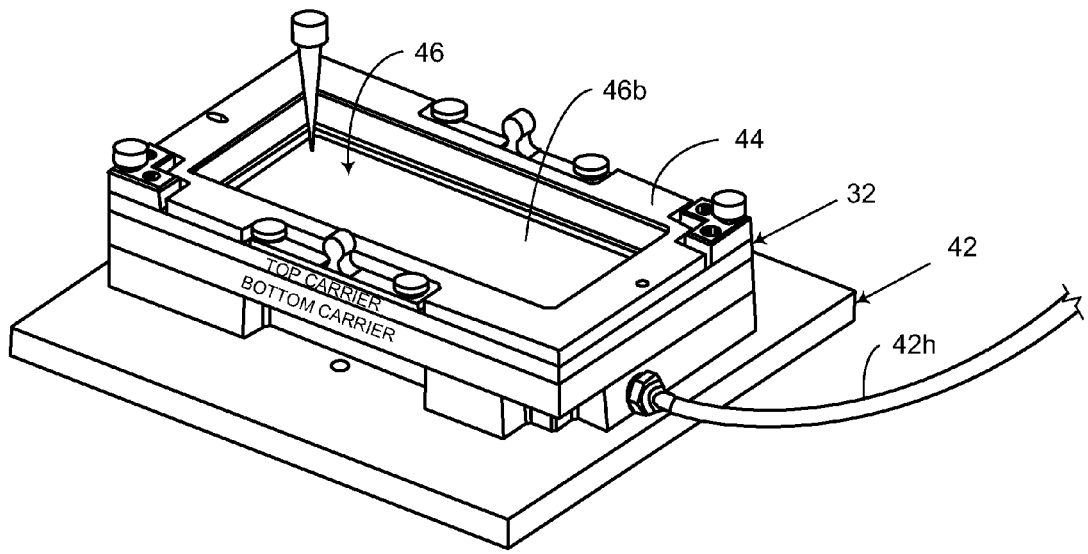
Figure 7F:
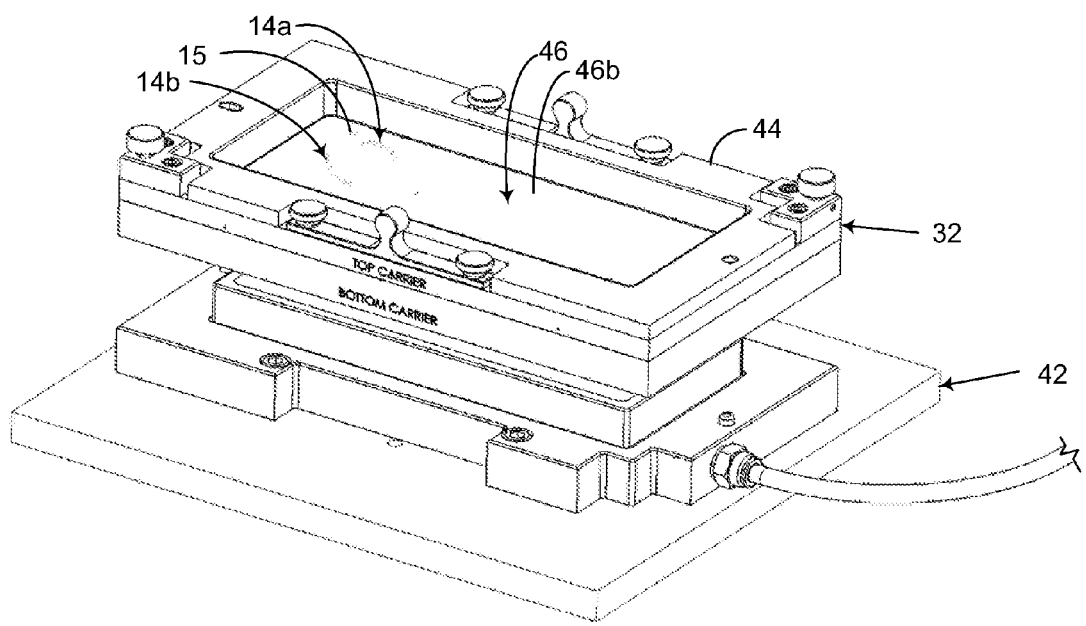
Figure 7G:
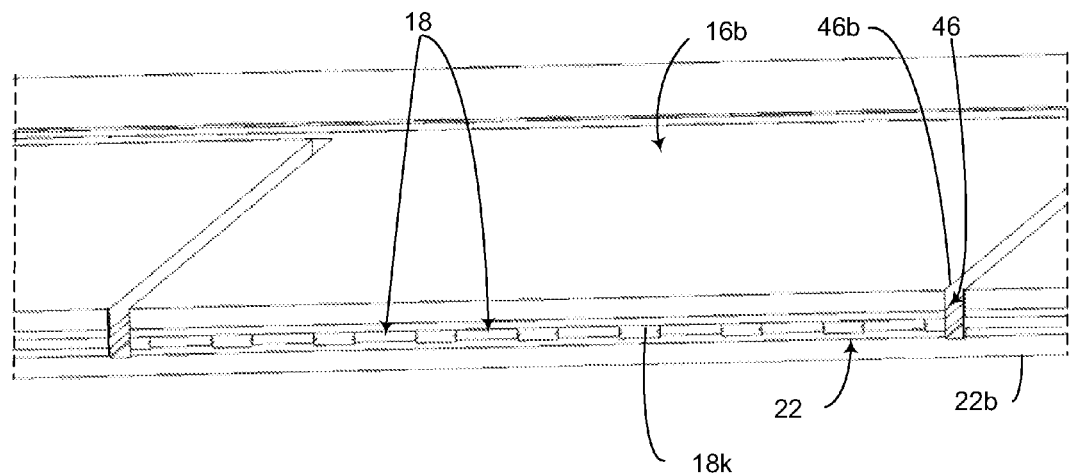
Figure 7H:
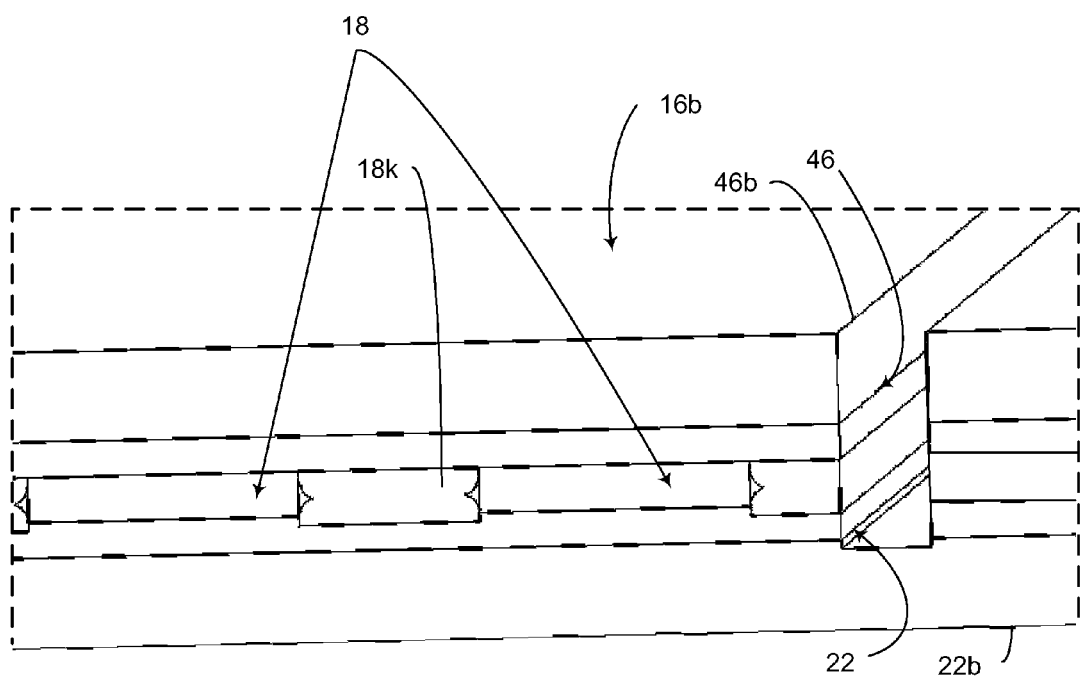
Figure 8A:
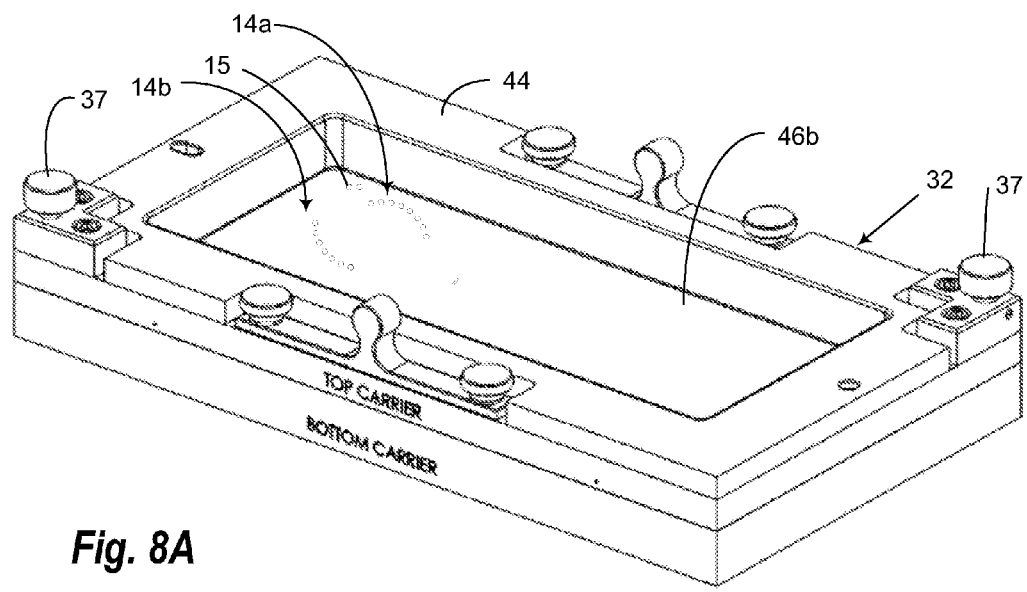
Figure 8B:
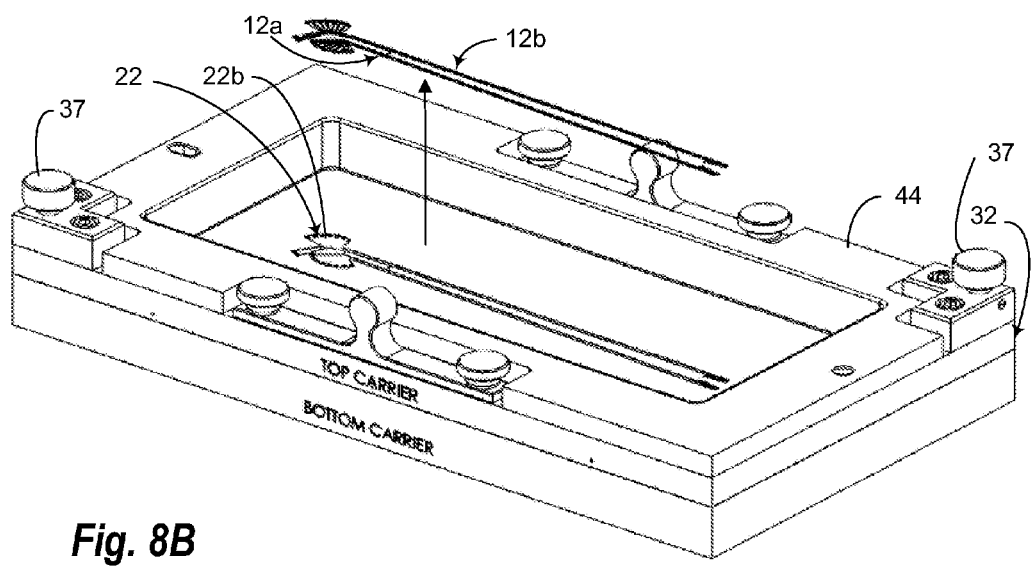
Figure 8C:
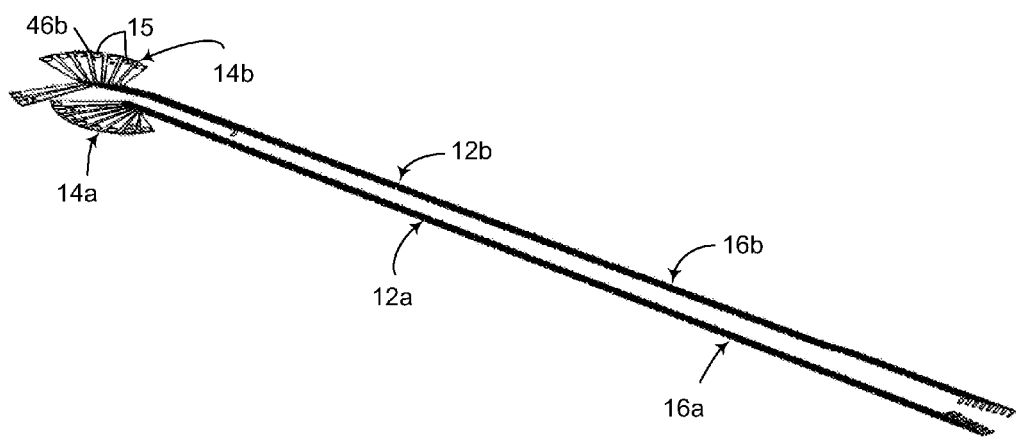
Figure 8D:
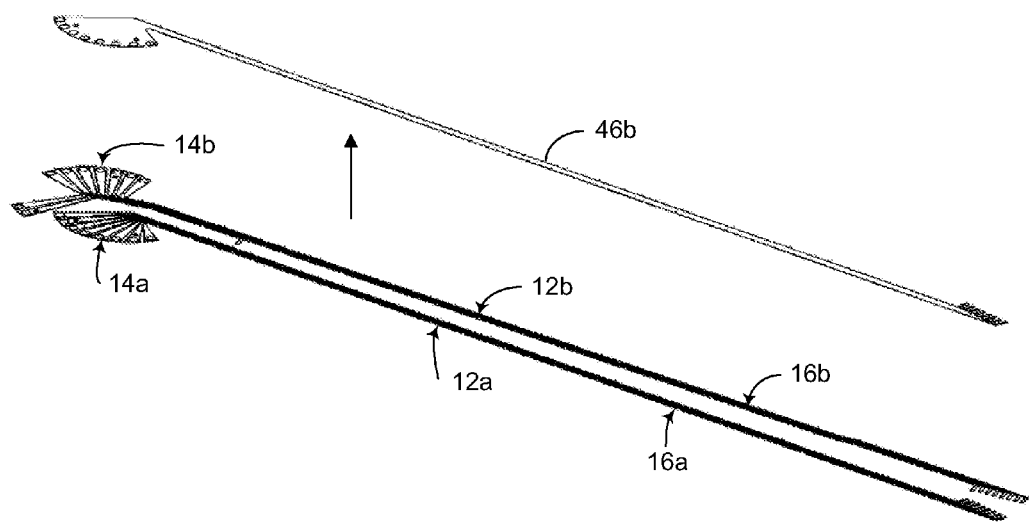
Figure 8E:
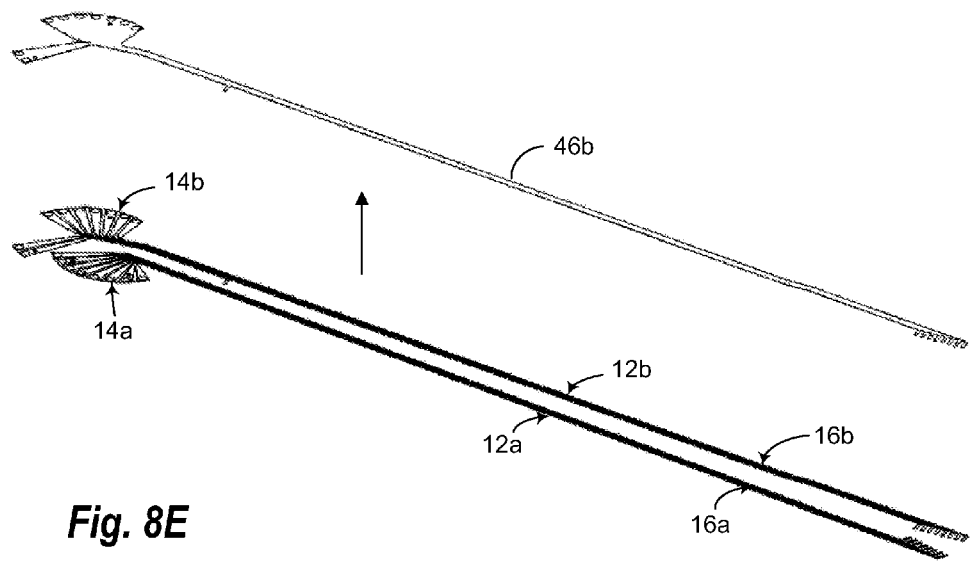
Figure 8F:
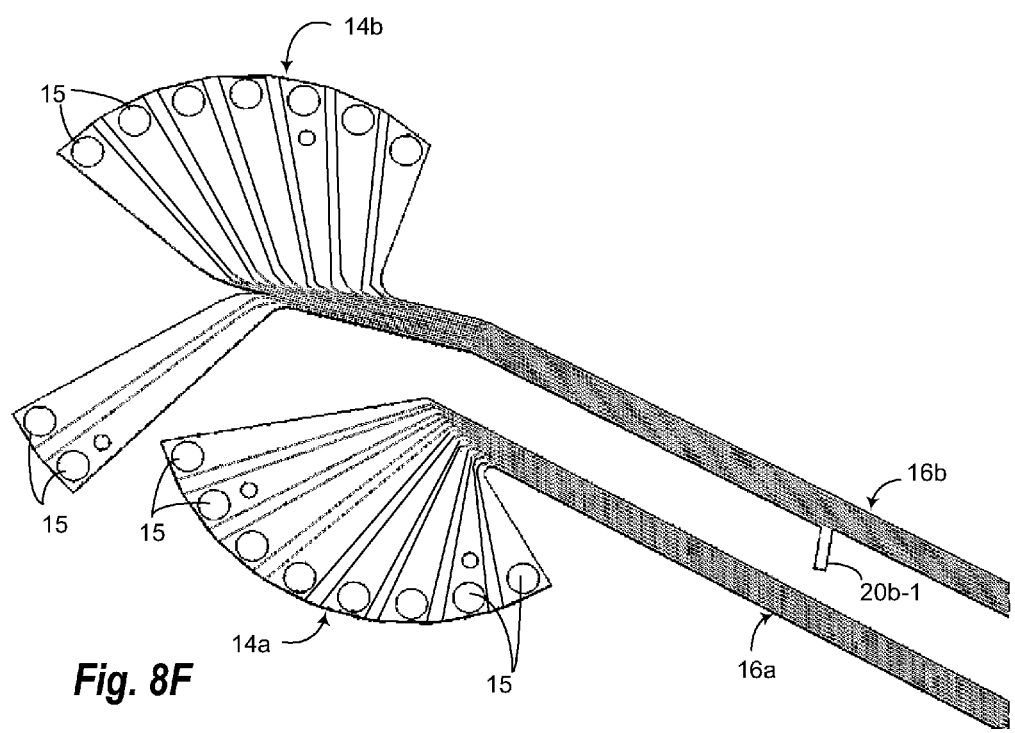
Figure 8G:
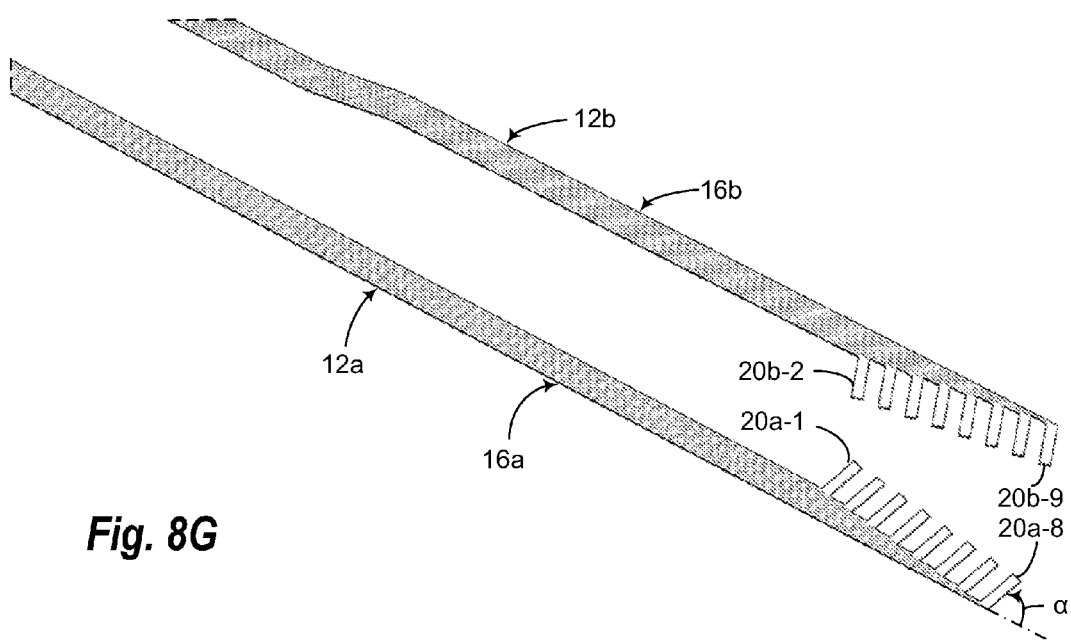
Figure 8H:
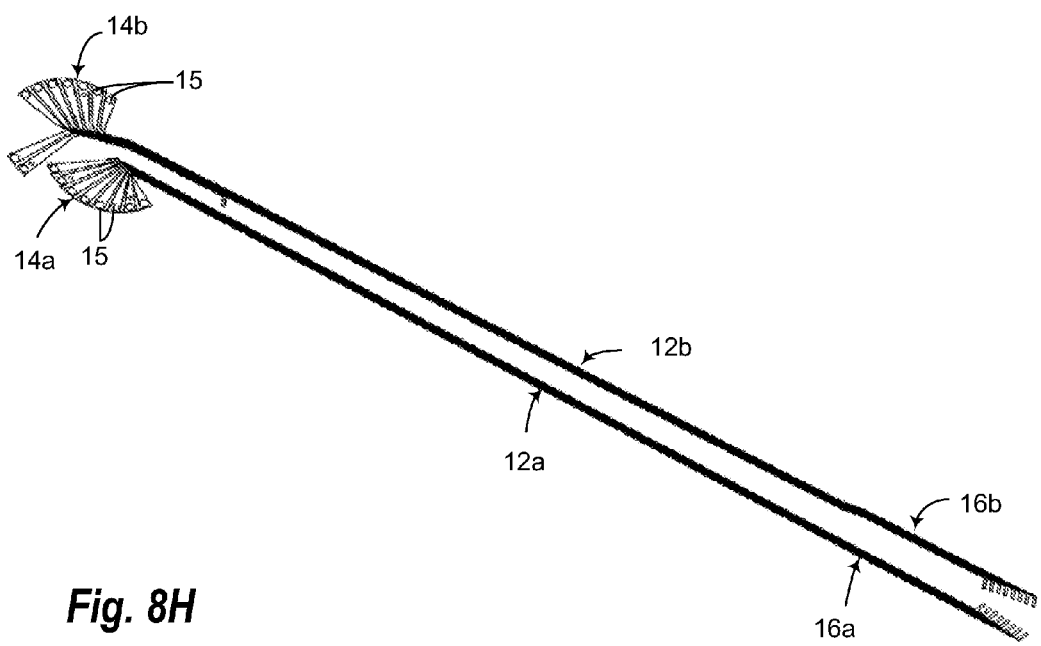
Figure 9A:
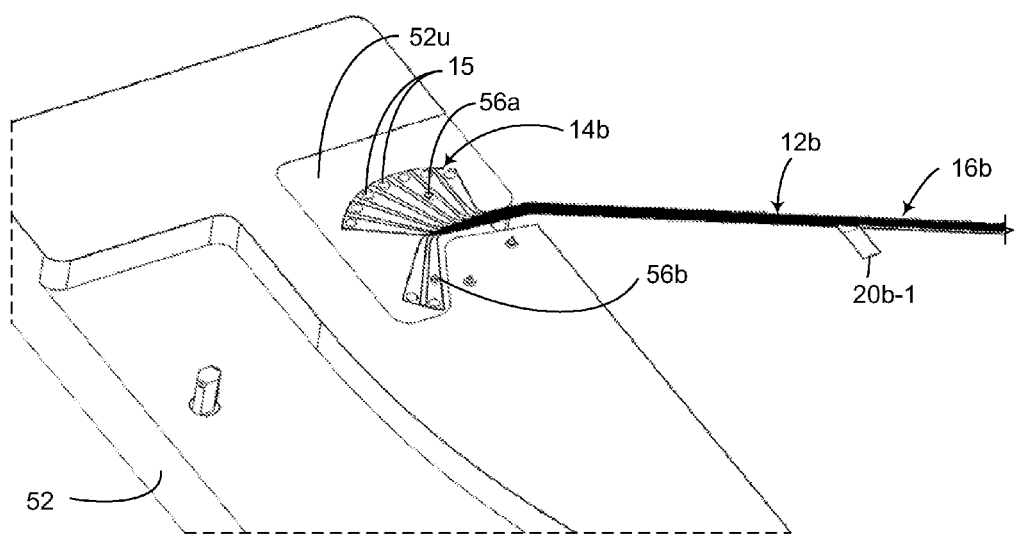
Figure 9B:
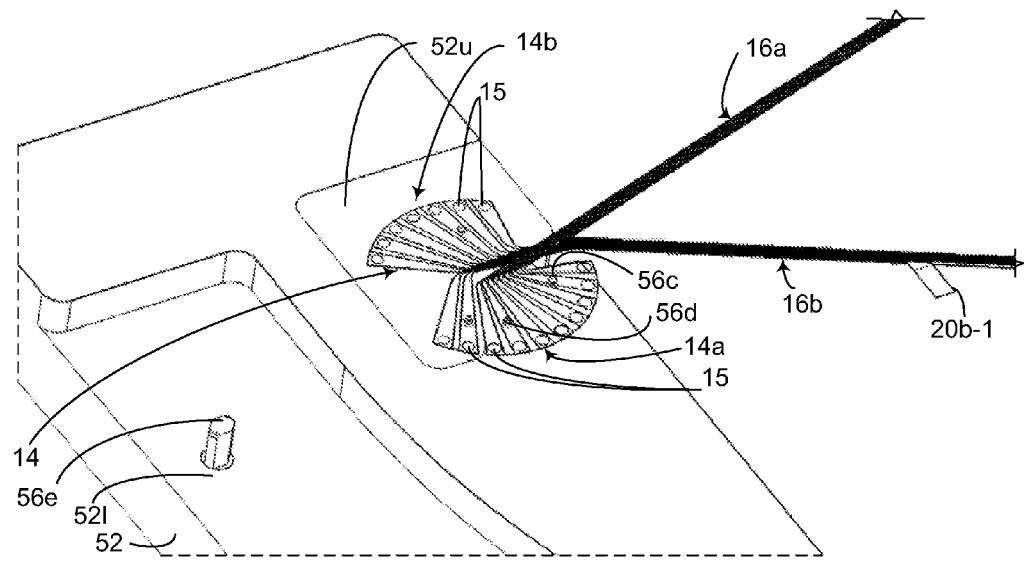
Figure 9C:
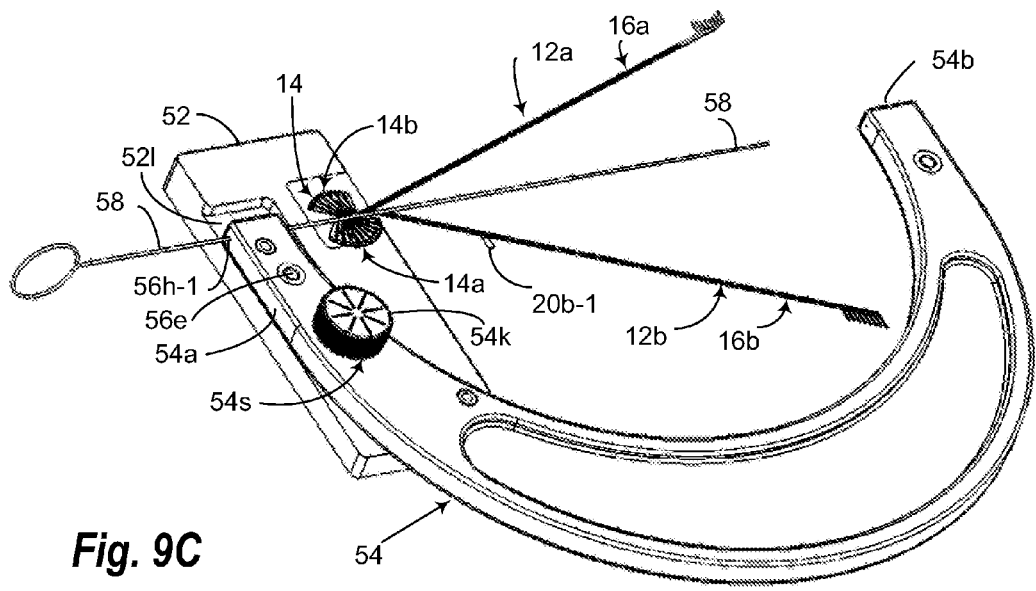
Figure 9D:
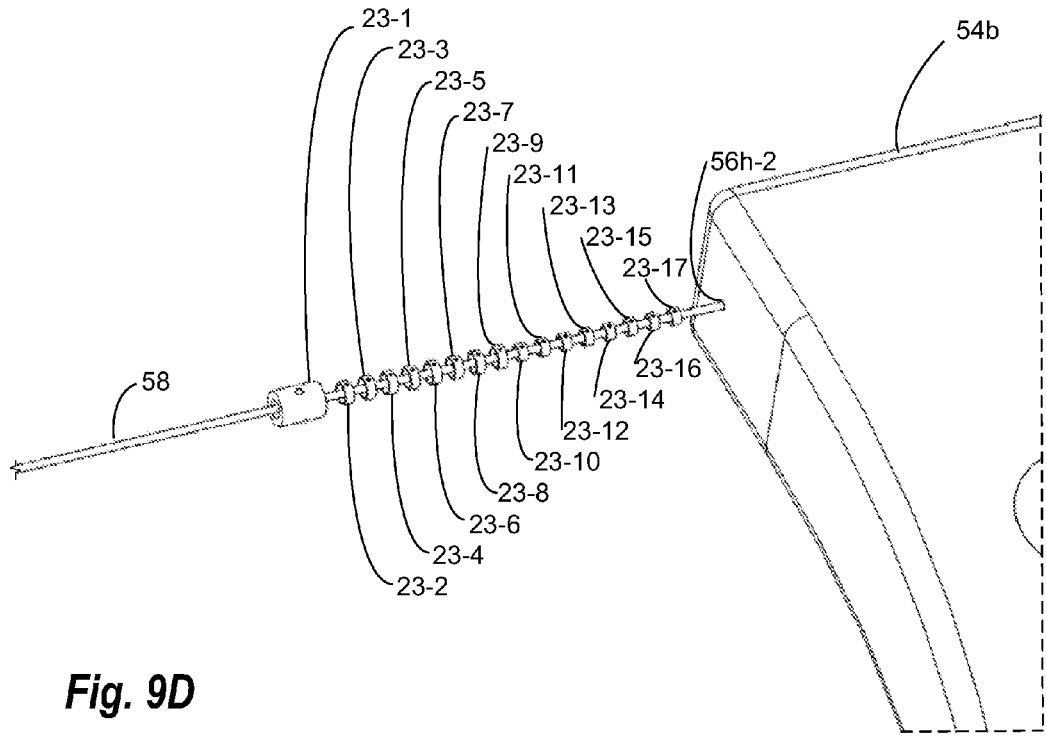
Figure 9E:
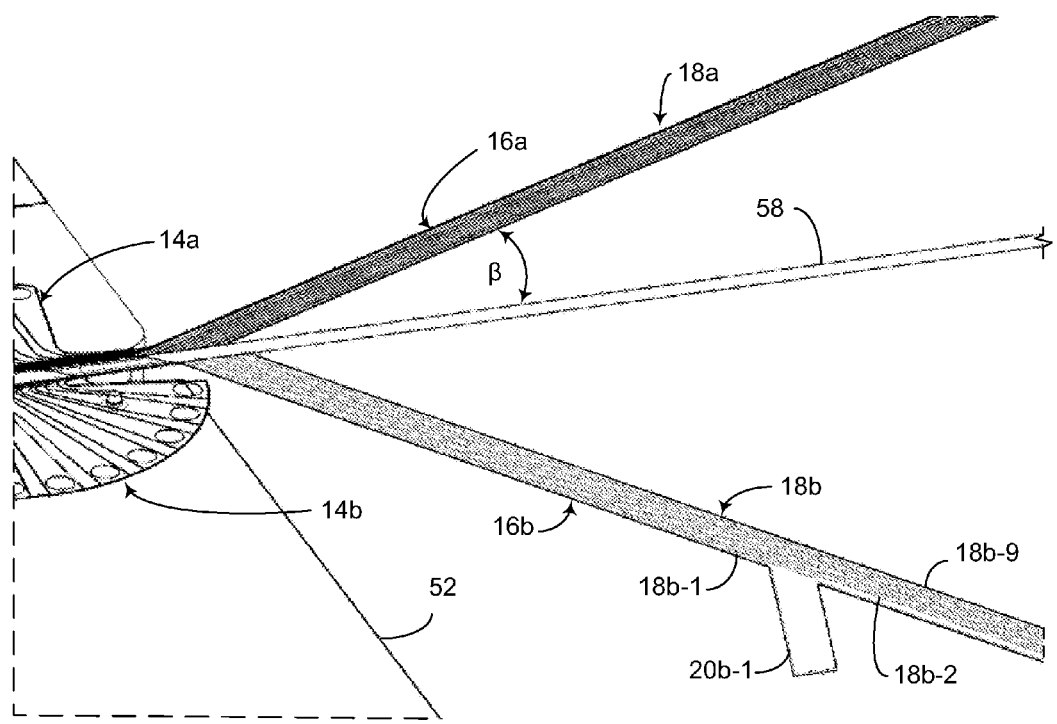
Figure 9F:
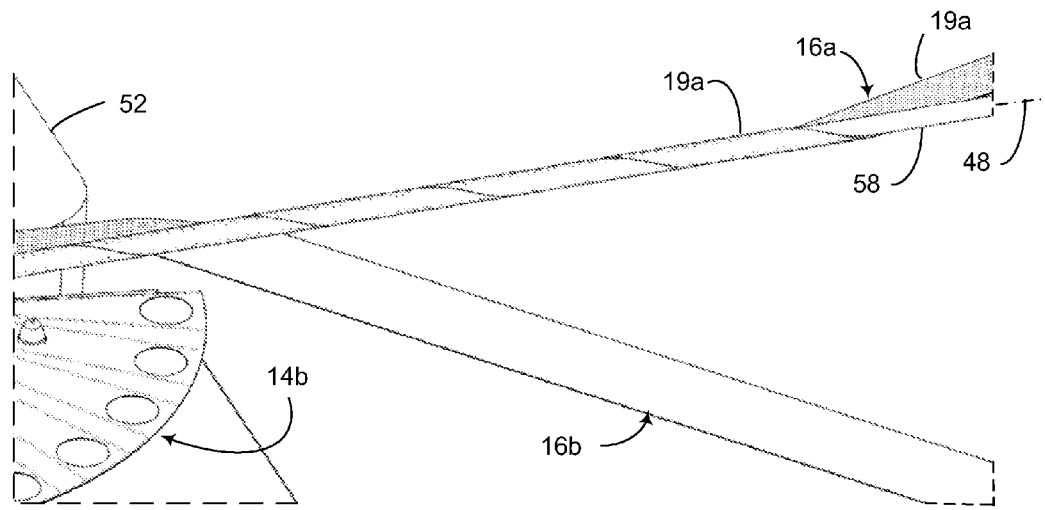
Figure 9G:
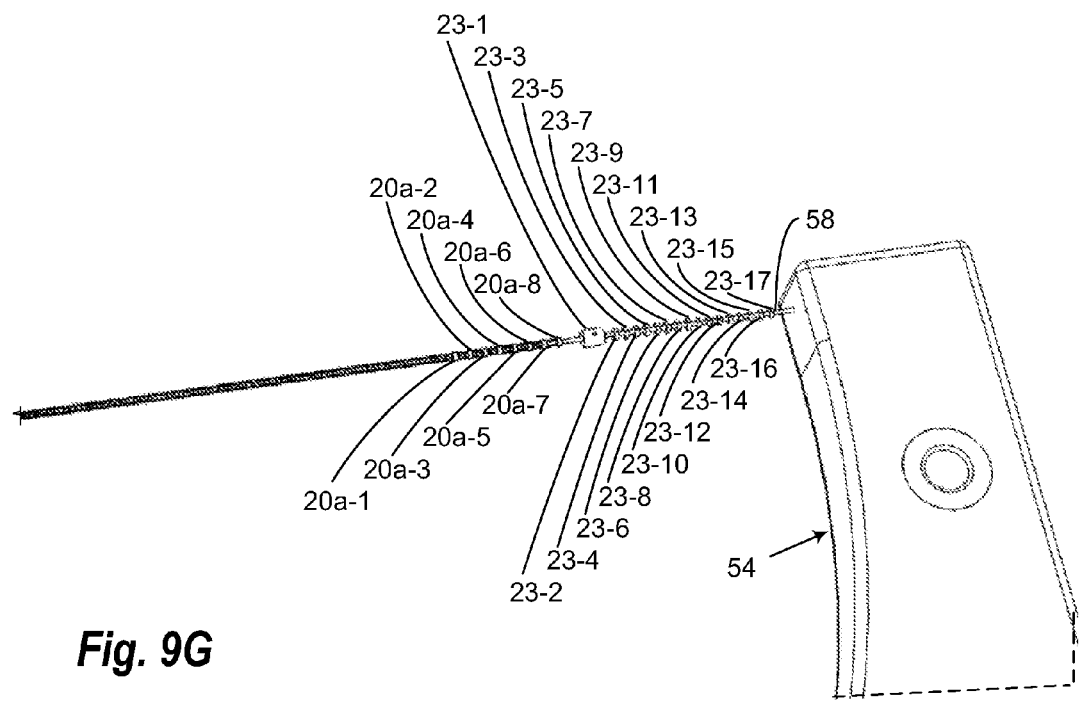
Figure 9H:
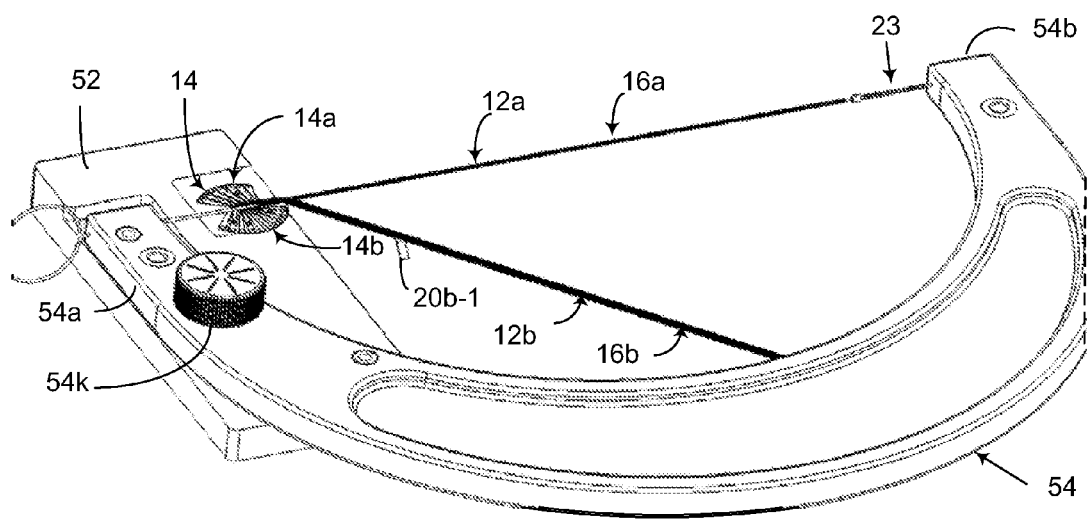
Figure 9I:
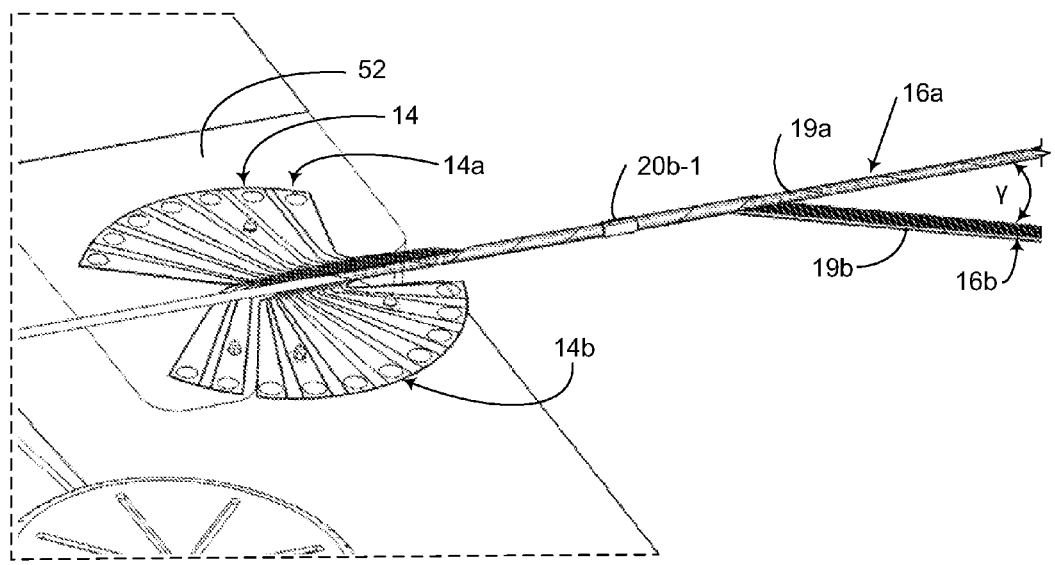
Figure 9J:
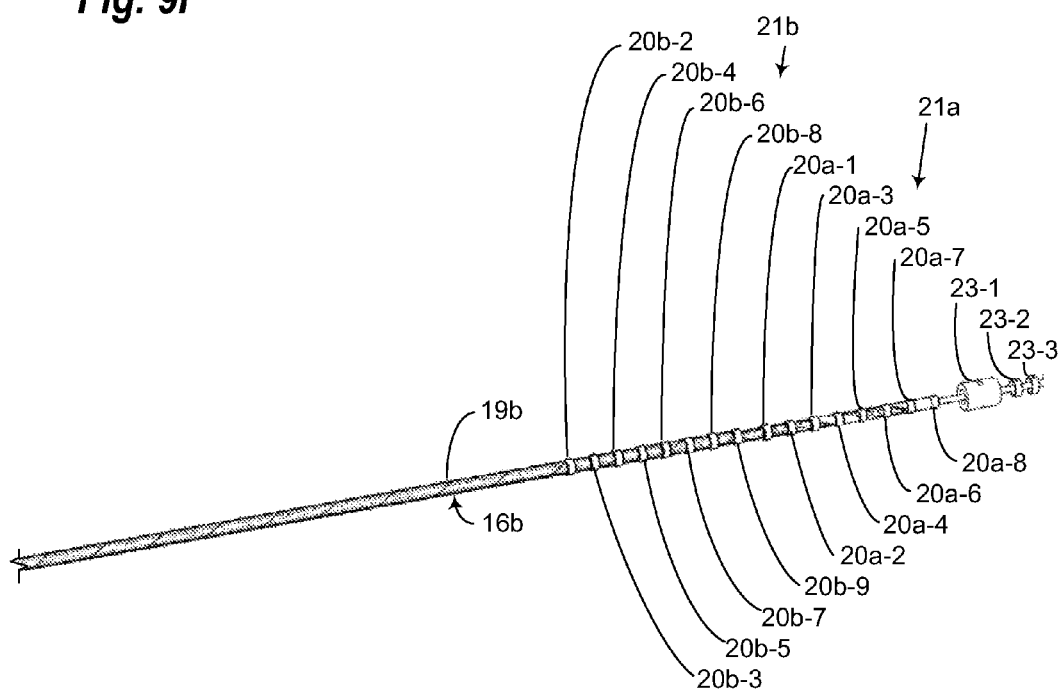
Figure 10A:
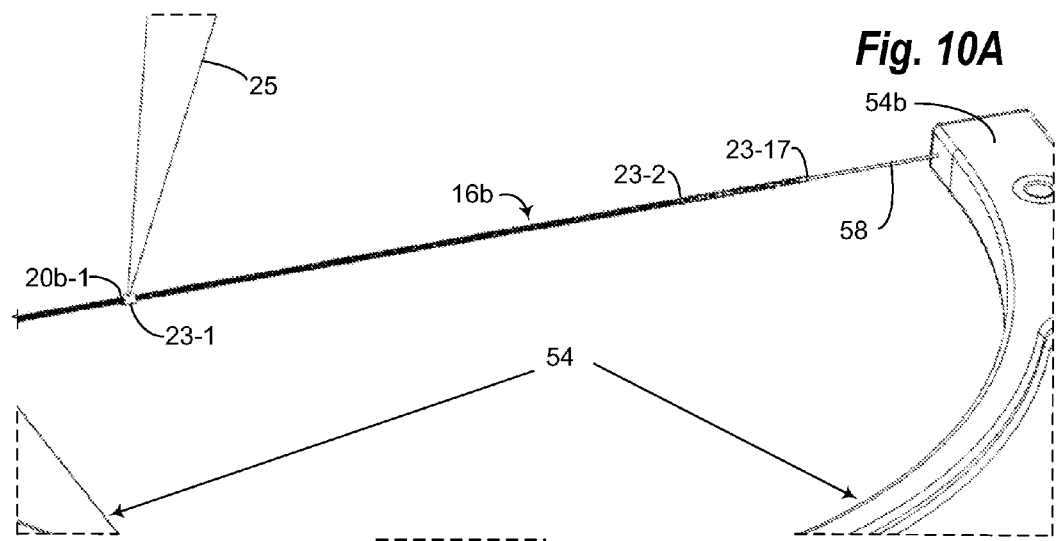
Figure 10B:
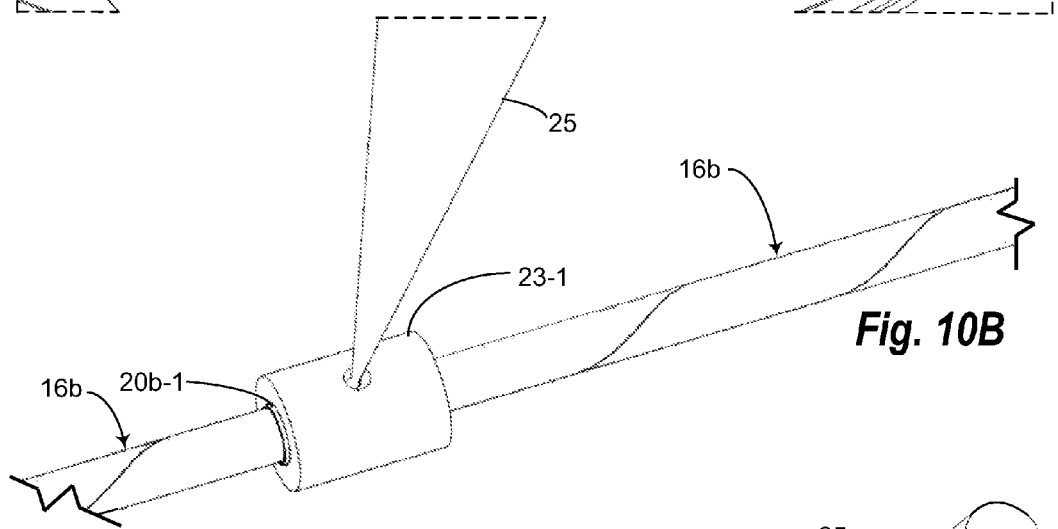
Figure 10C:
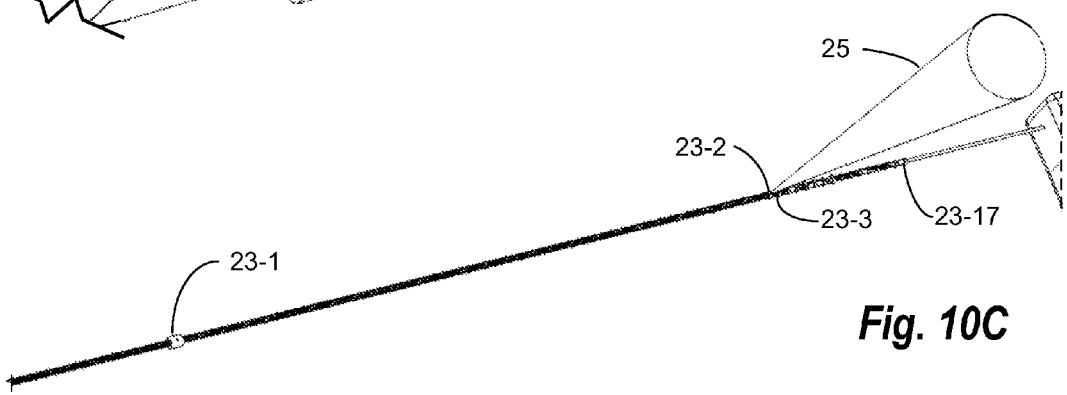
Figure 11A:
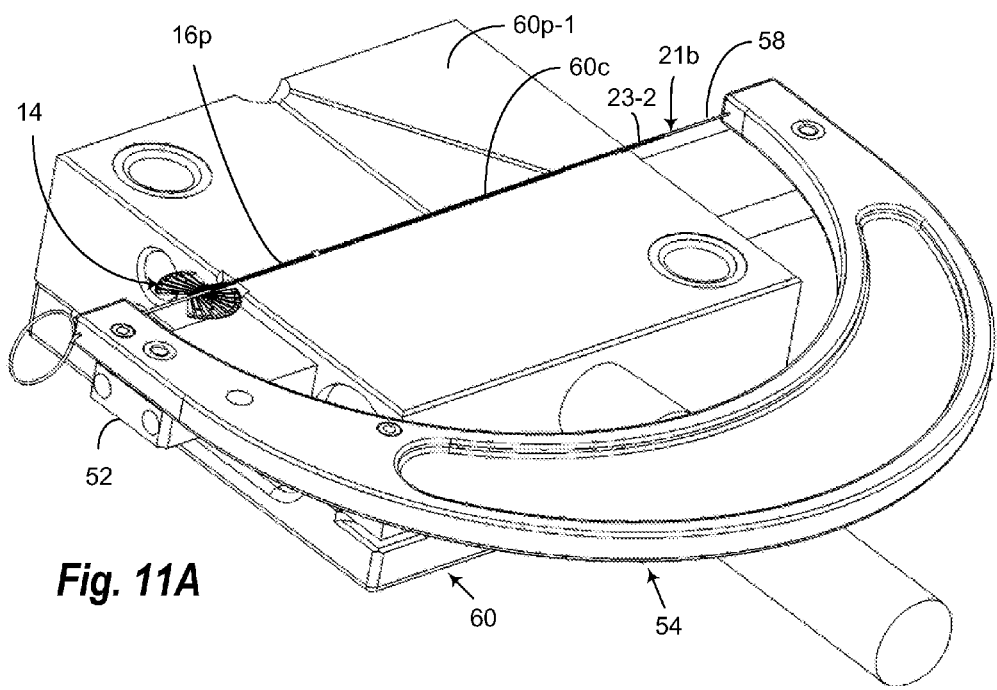
Figure 11B:
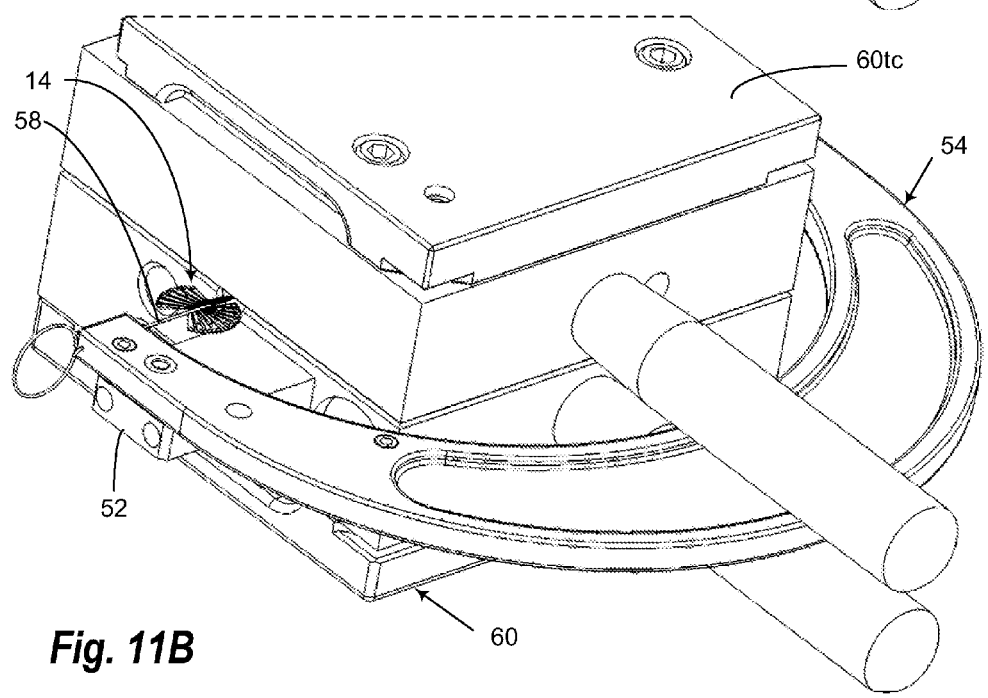
Figure 11C:
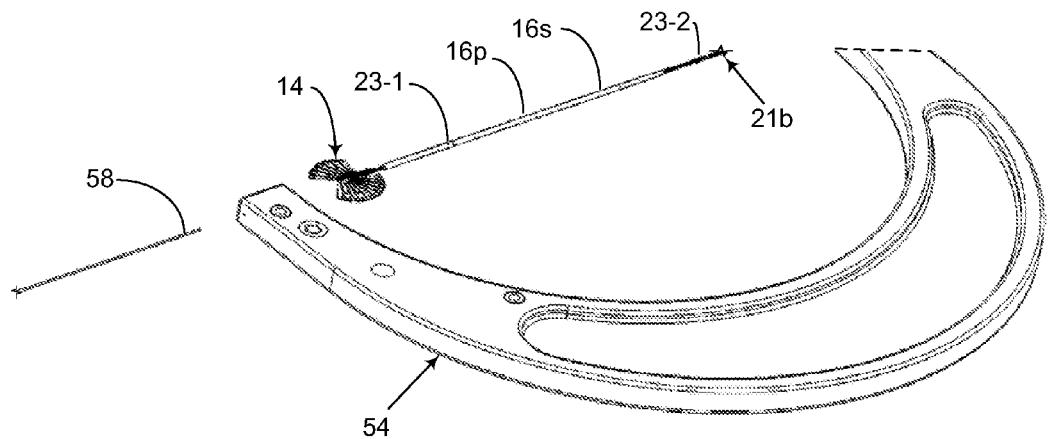
Figure 11D:
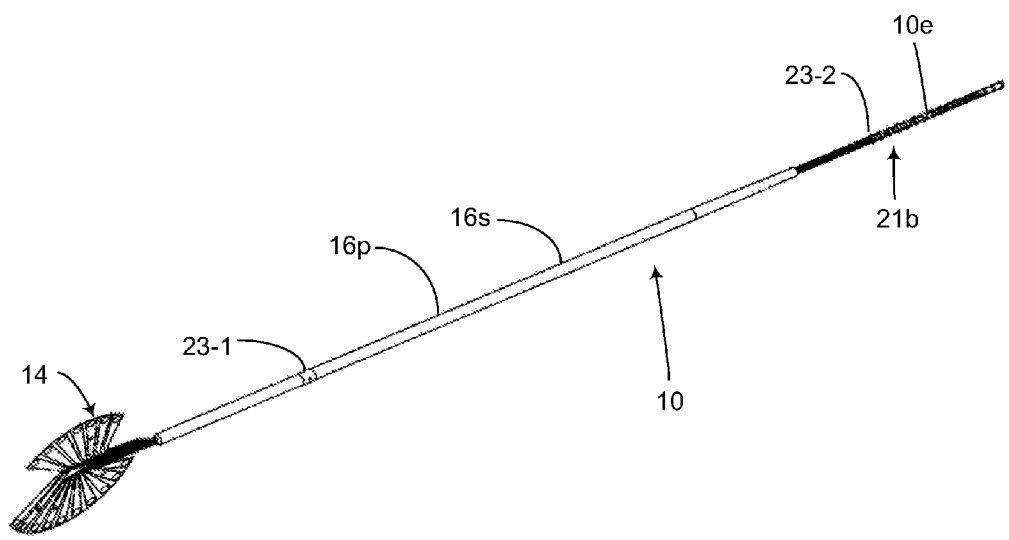
Figure 11E:
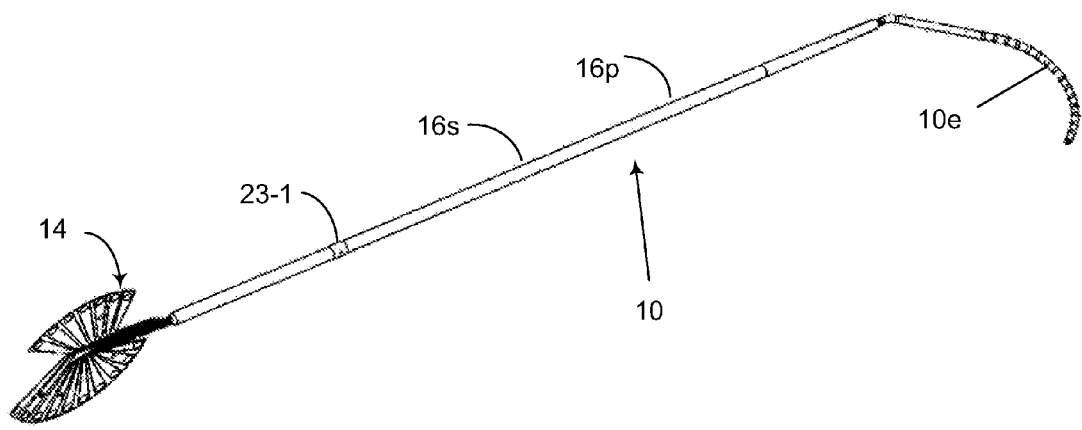
Figure 11F:
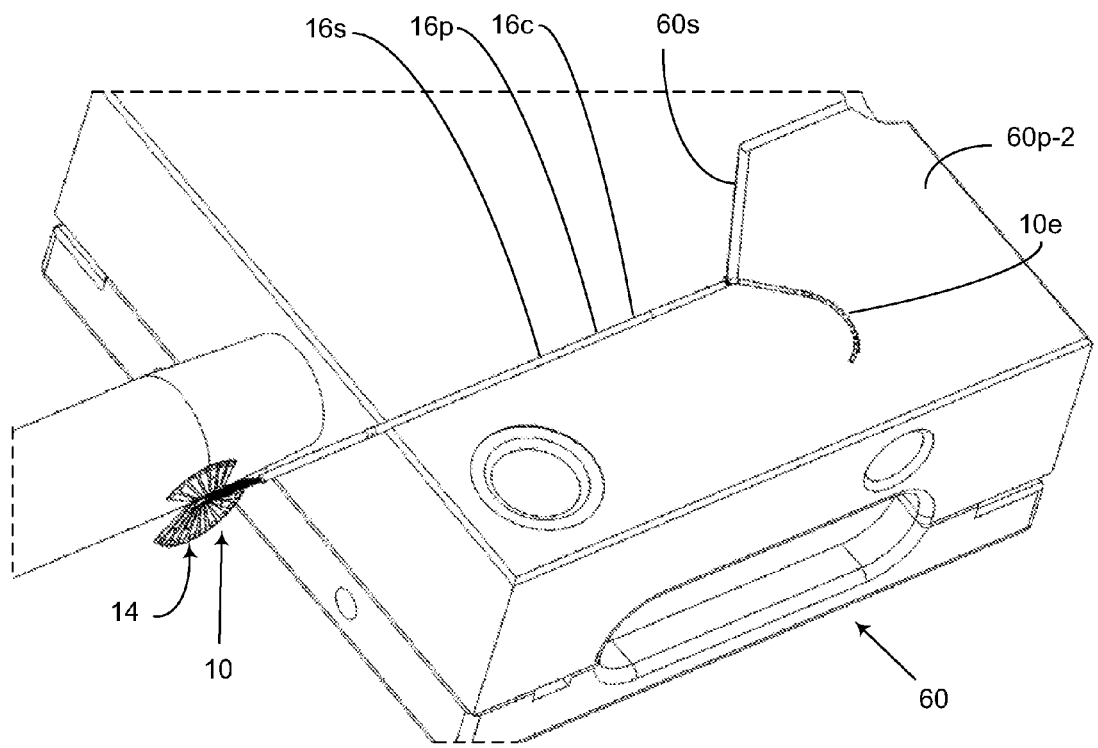
Figure 11G:
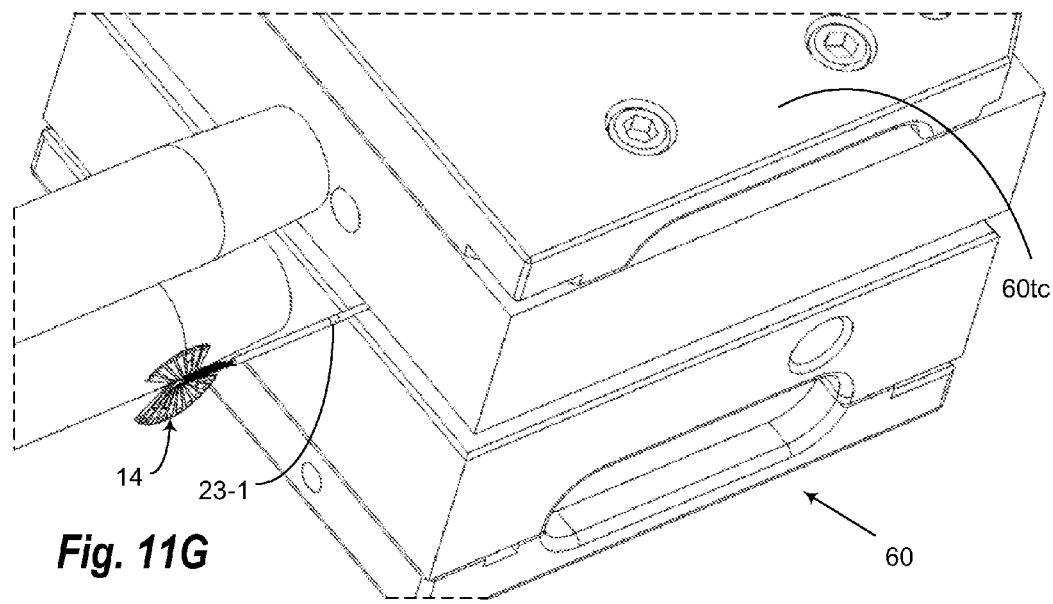
Figure 11H:
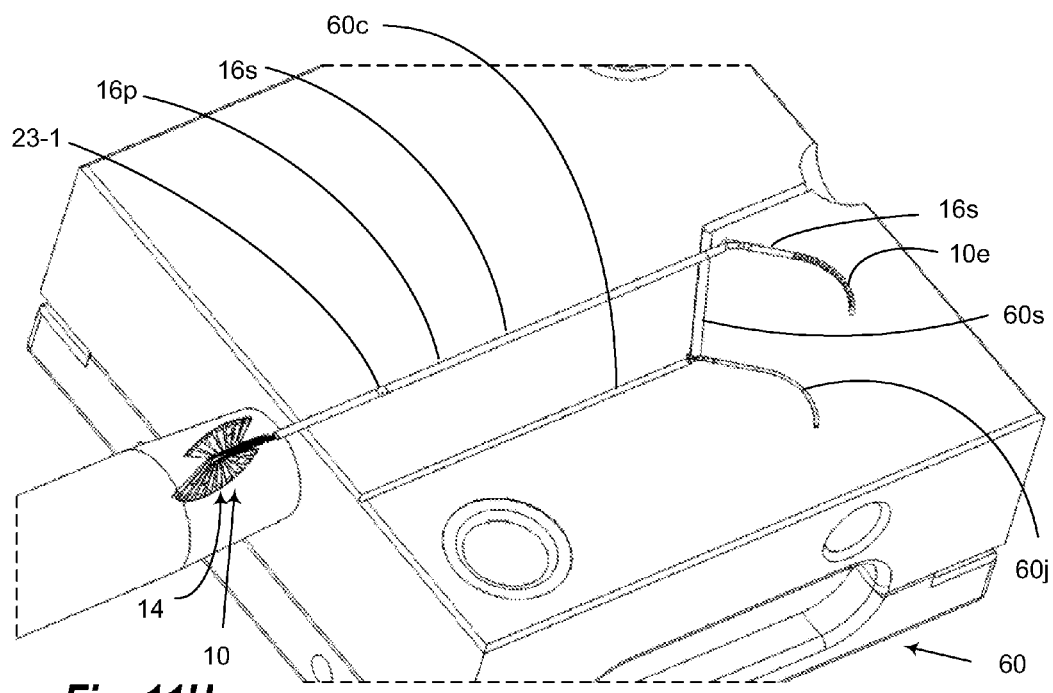
Figure 11I:
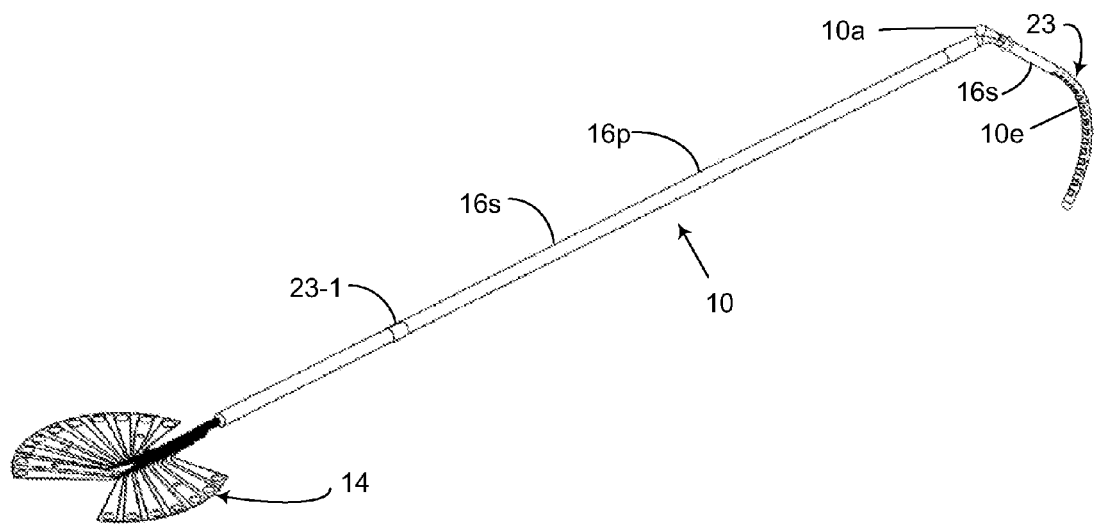
Figure 11J:
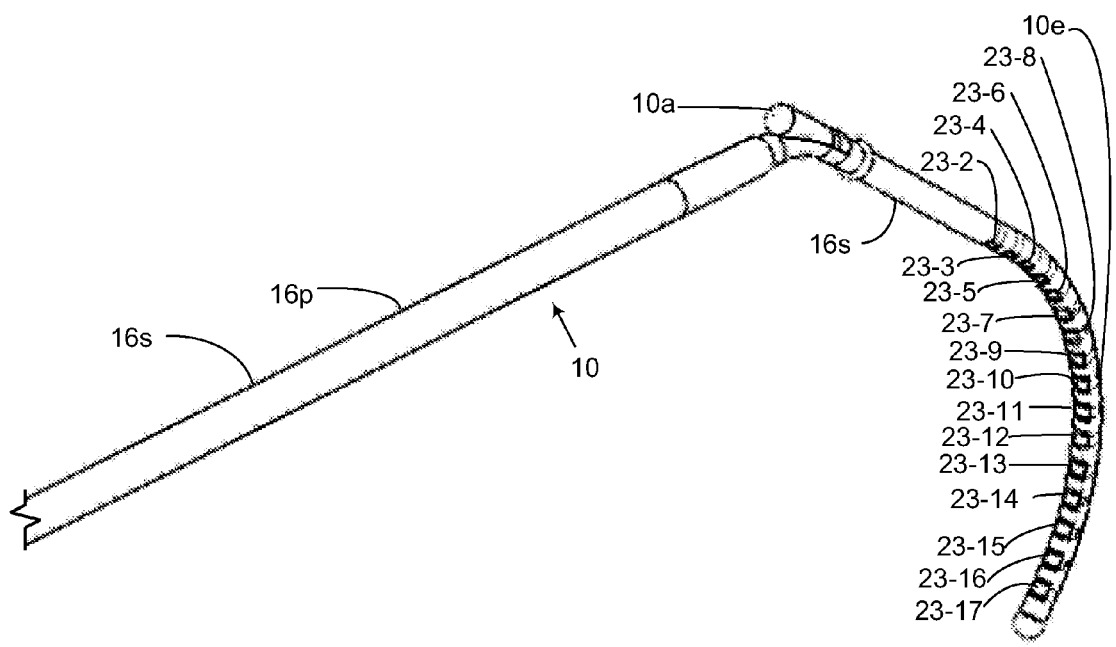
Figure 12A:
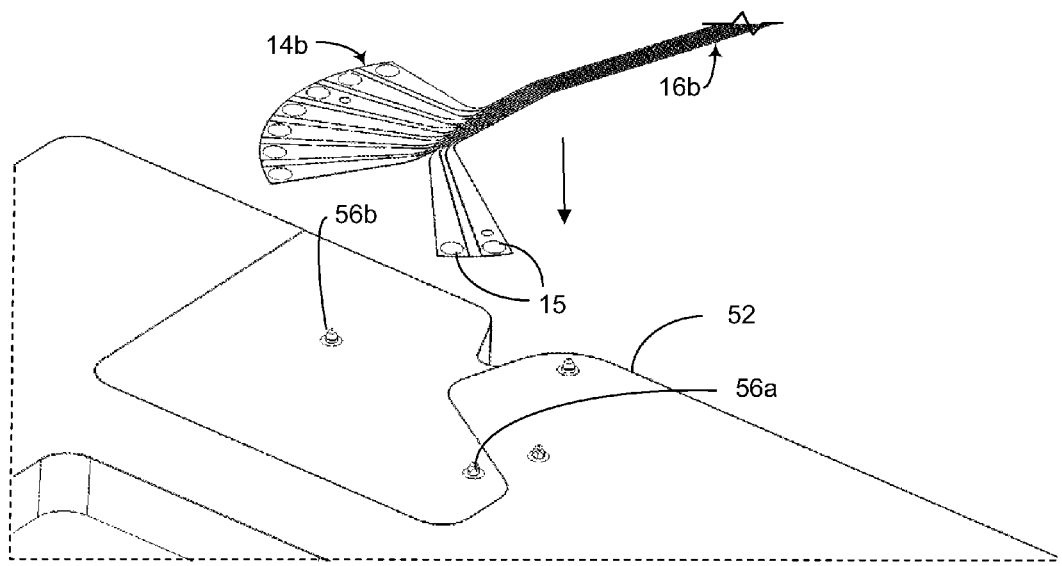
Figure 12B:
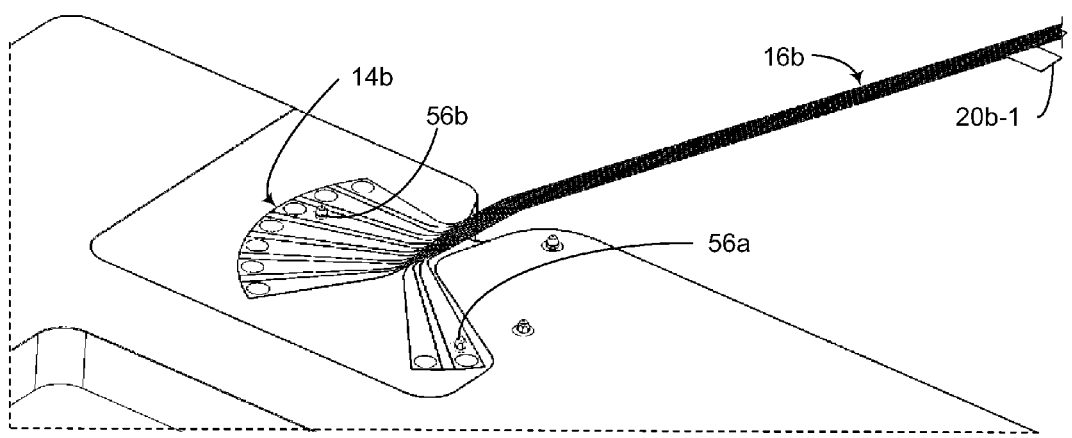
Figure 13A:
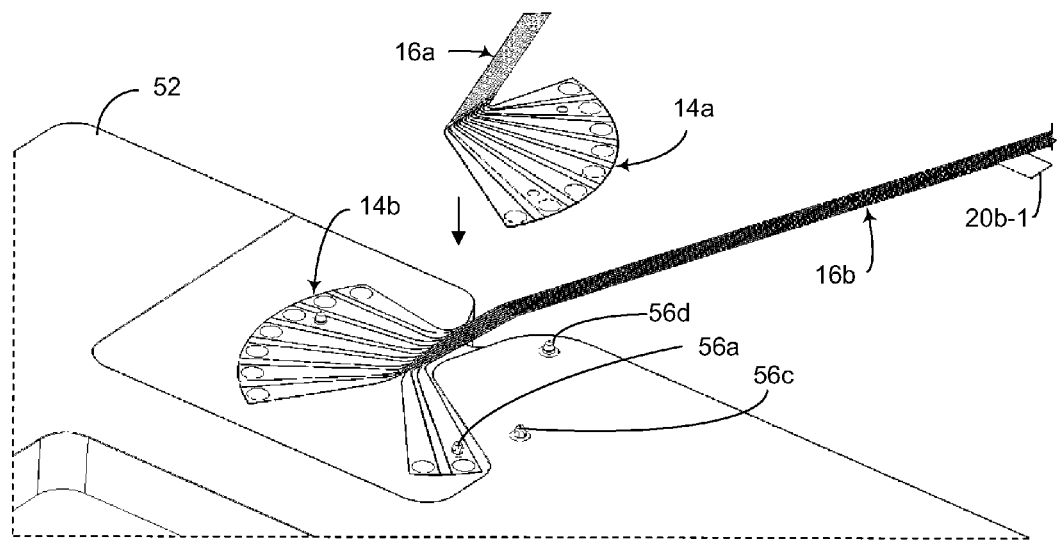
Figure 13B:
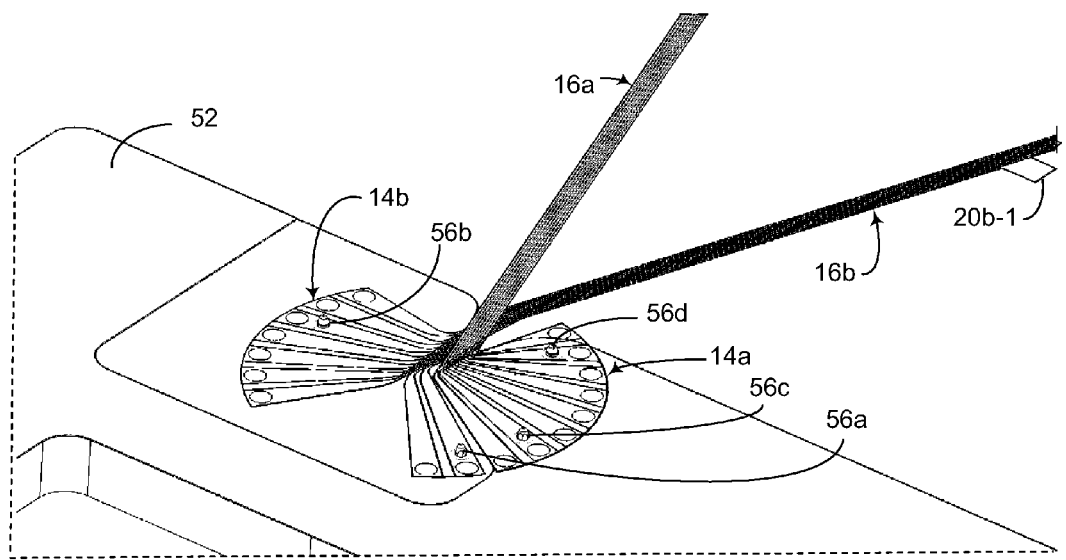
Figure 13C:
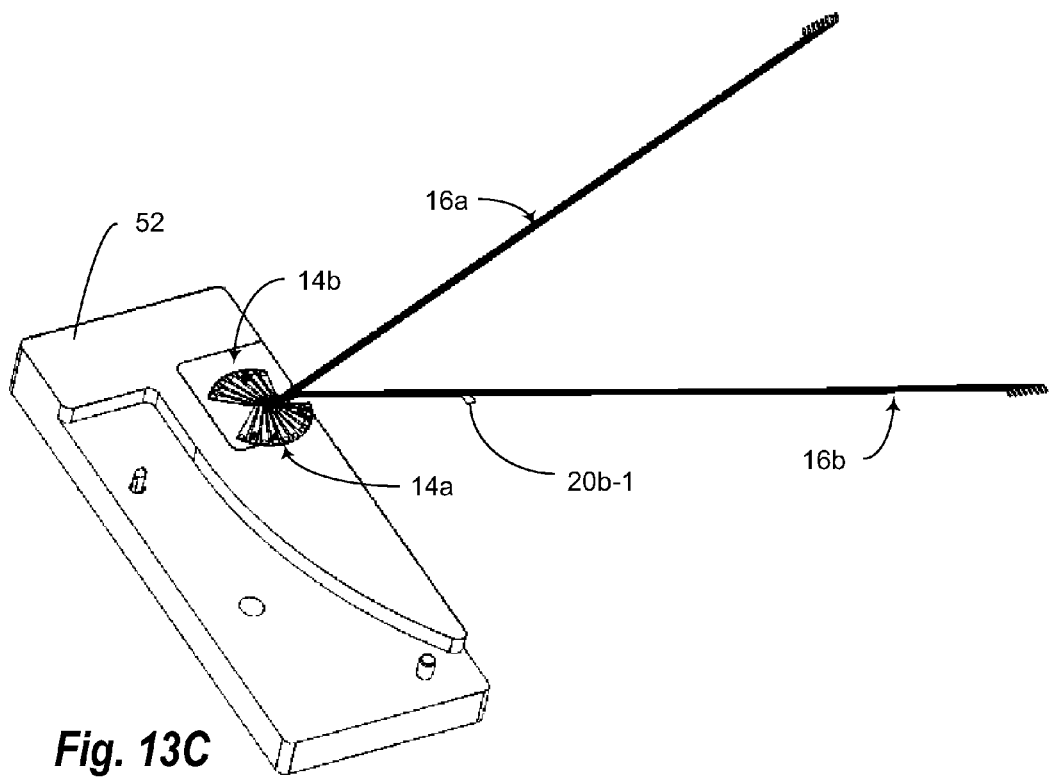
Figure 14A:
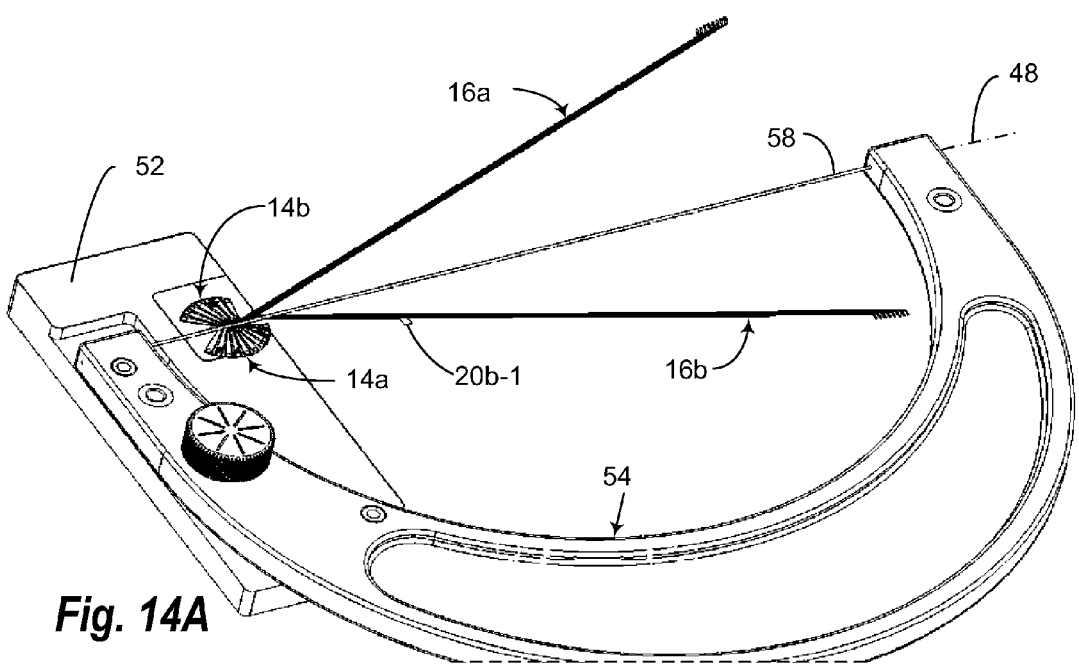
Figure 14B:
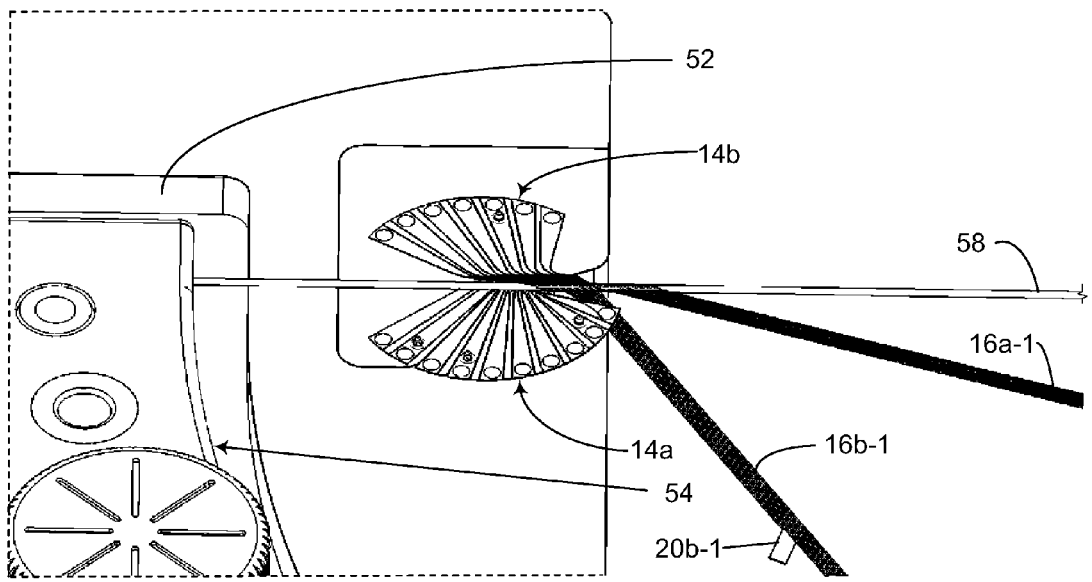
Figure 14C:
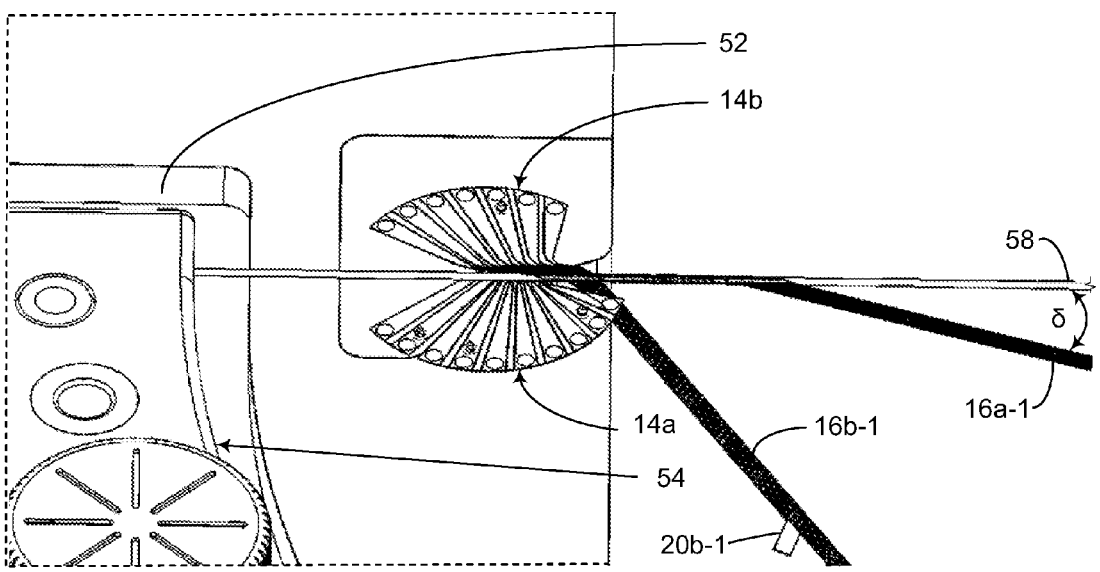
Figure 15A:
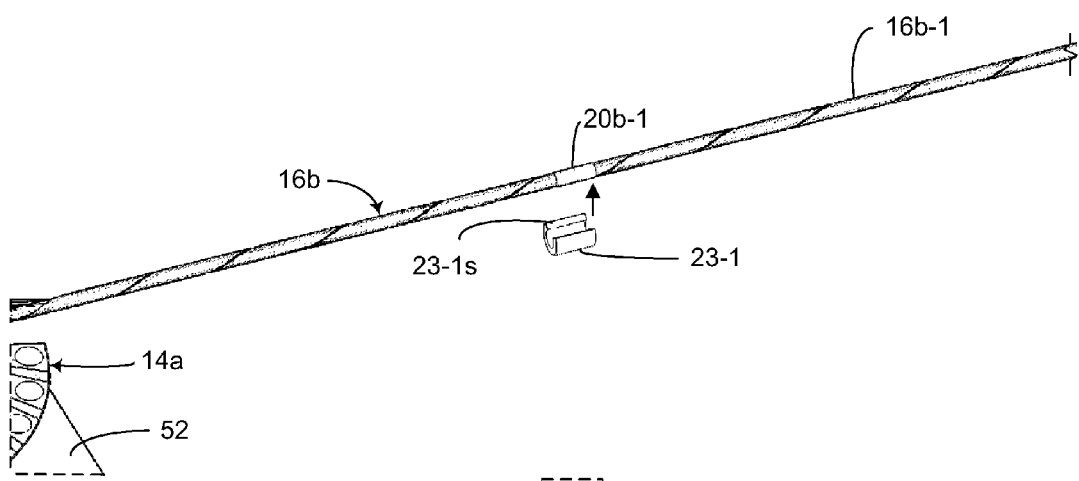
Figure 15B:
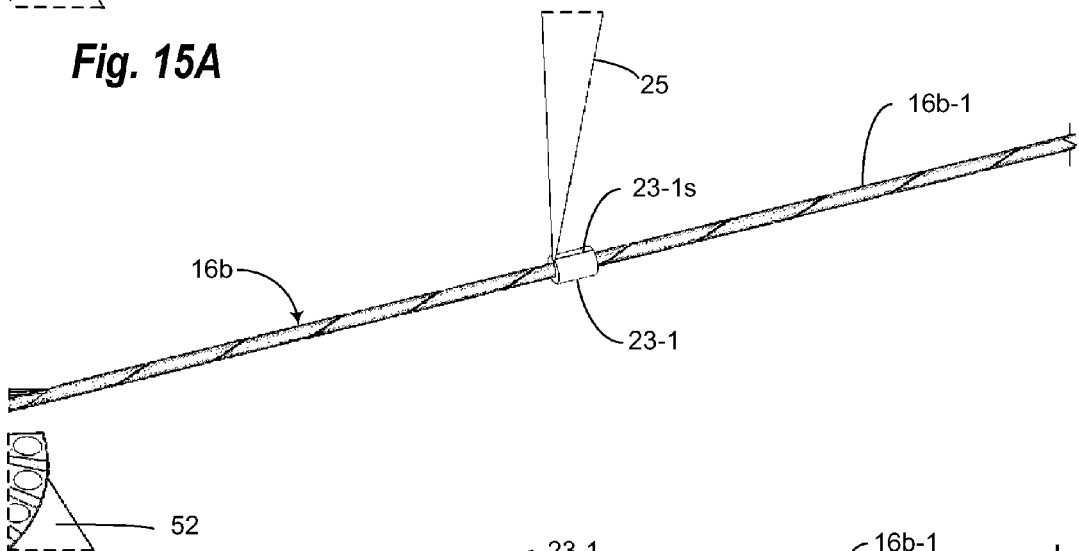
Figure 15C:
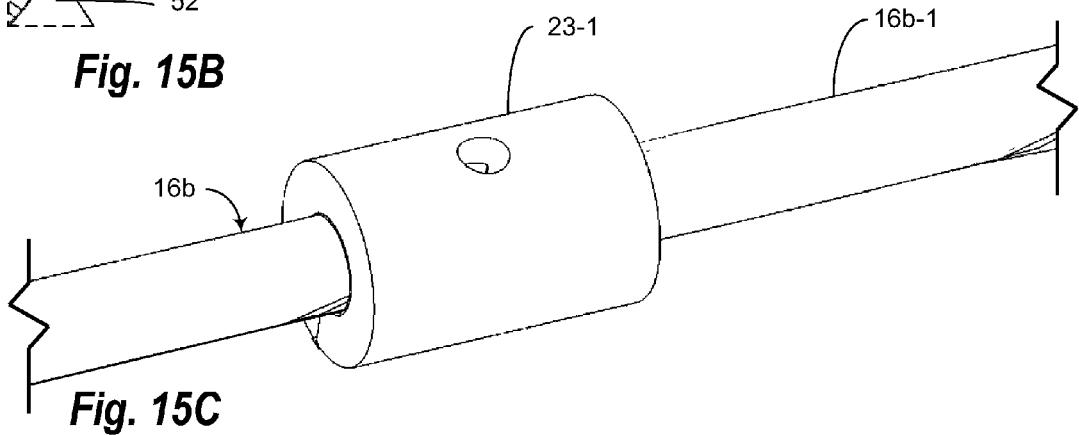
Figure 16A:
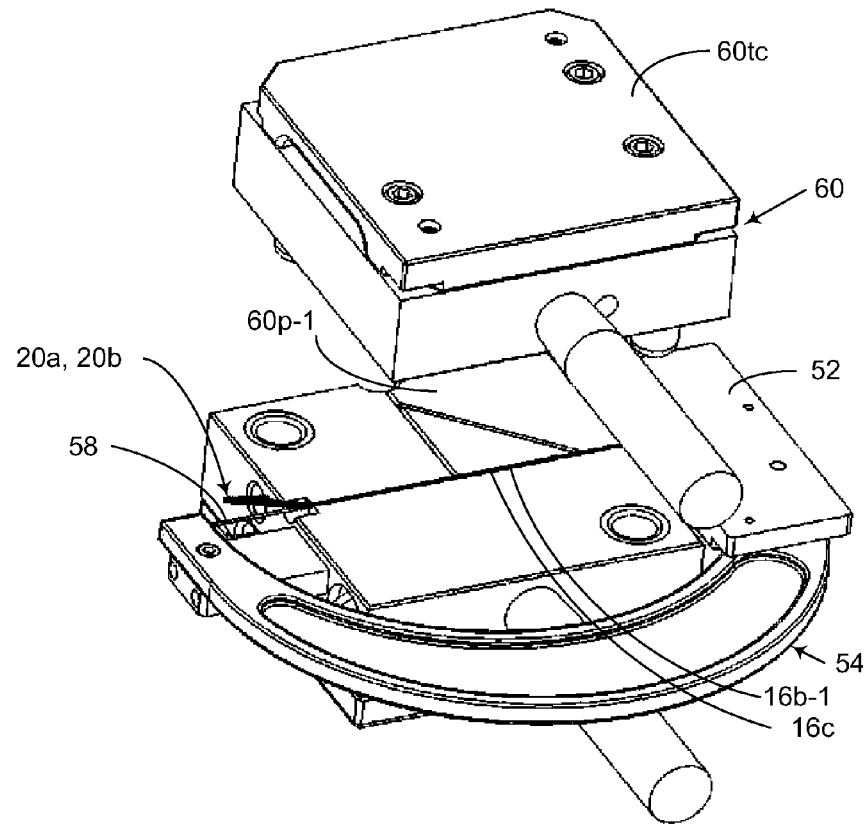
Figure 16B:
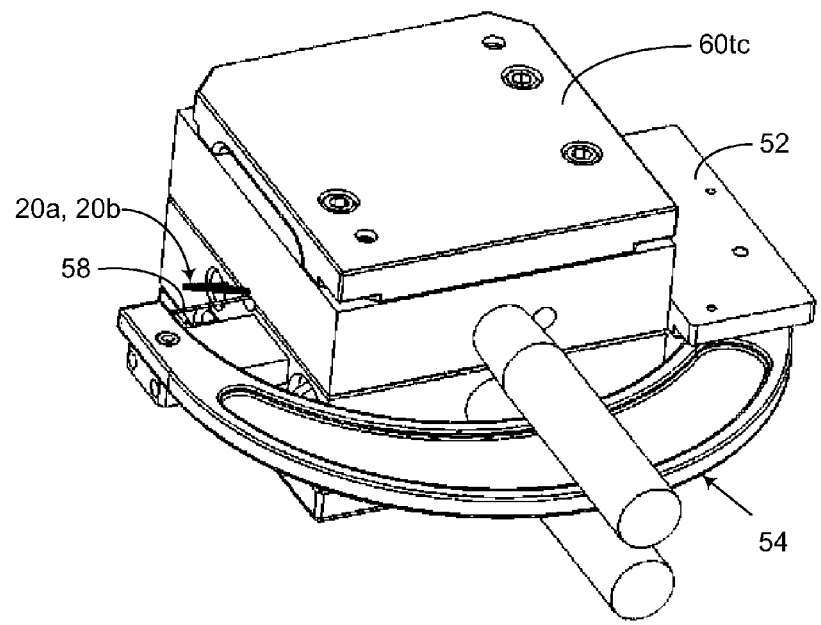
Figure 17A:
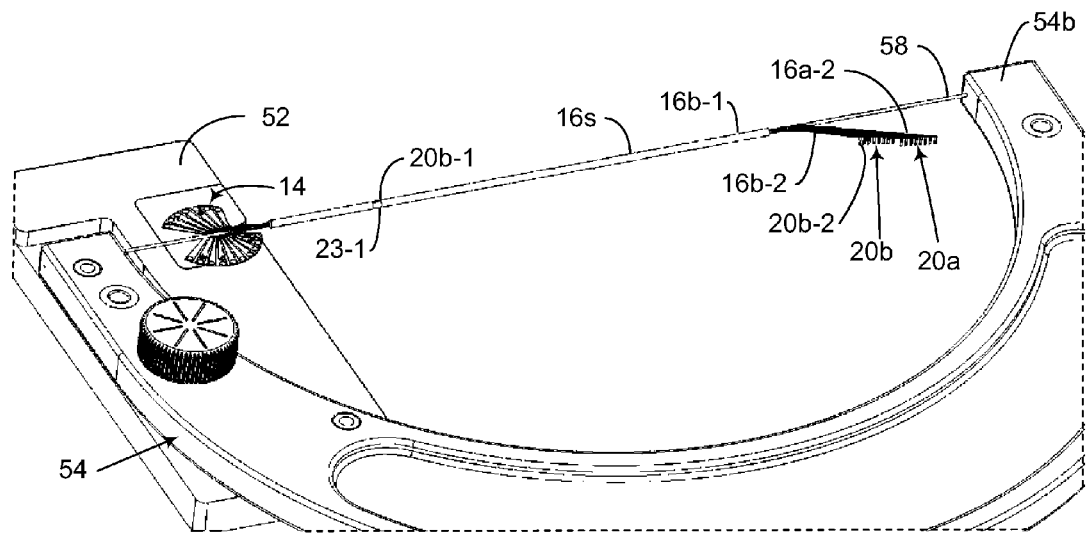
Figure 17B:
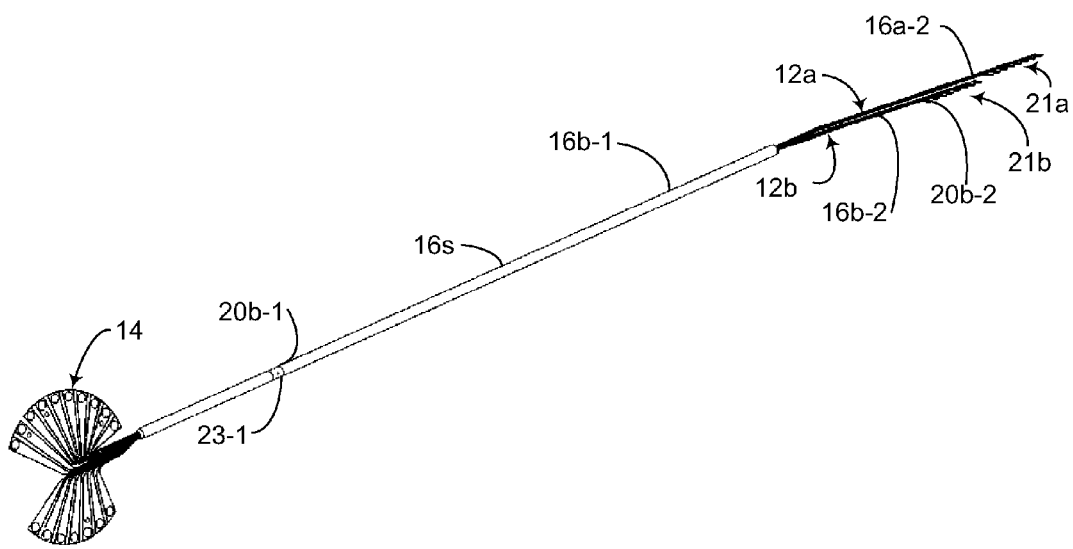
Figure 17C:
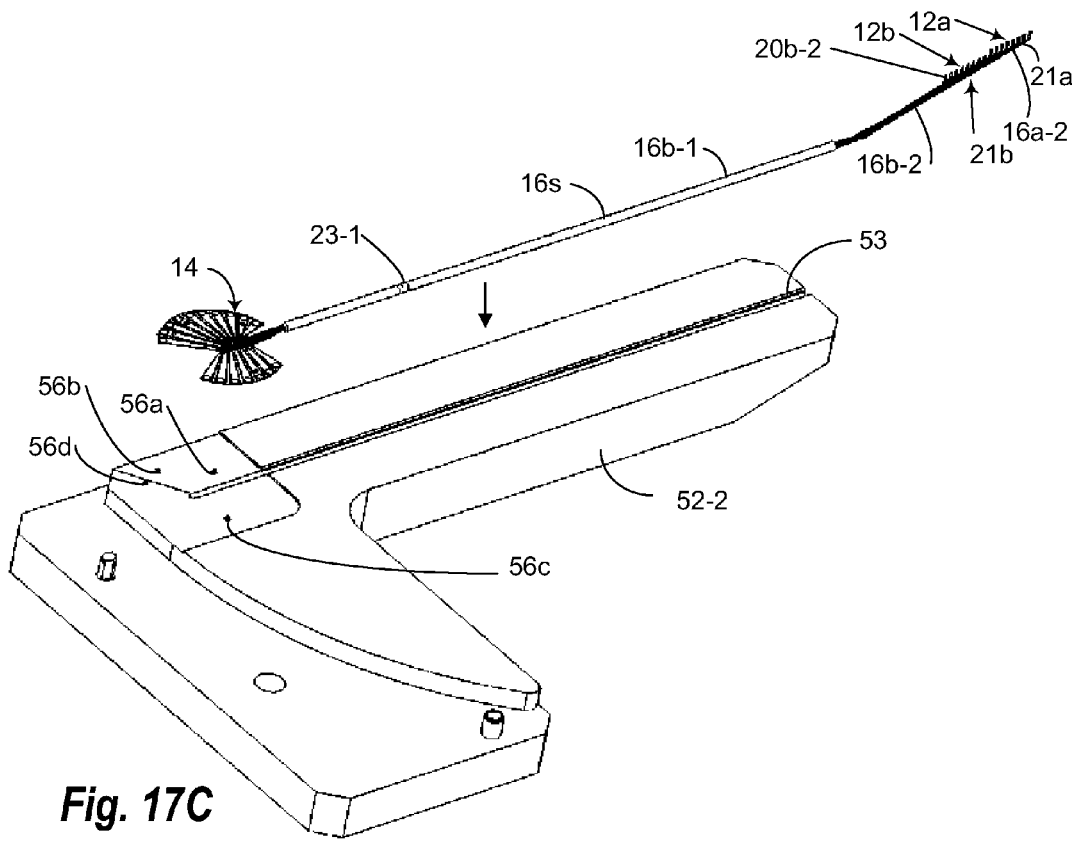
Figure 17D:
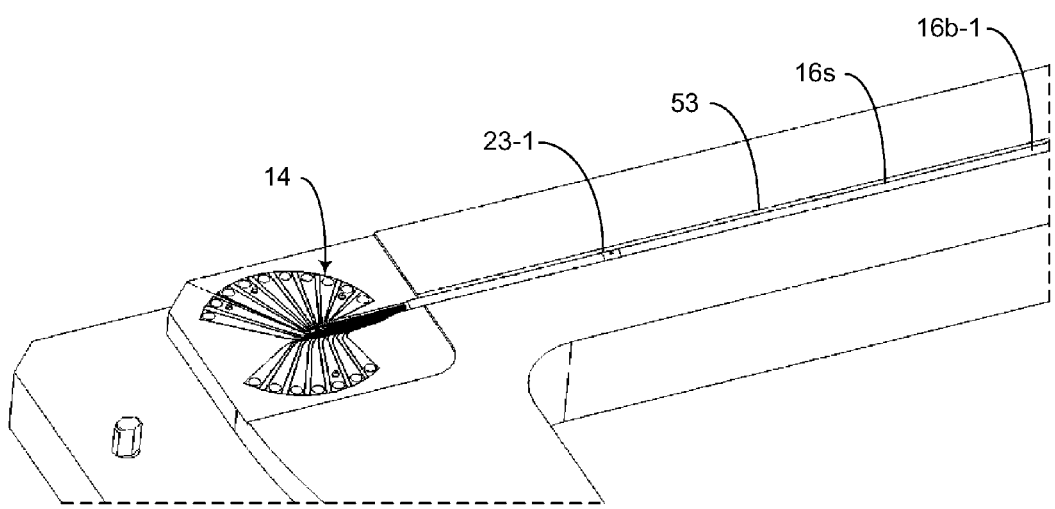
Figure 17E:
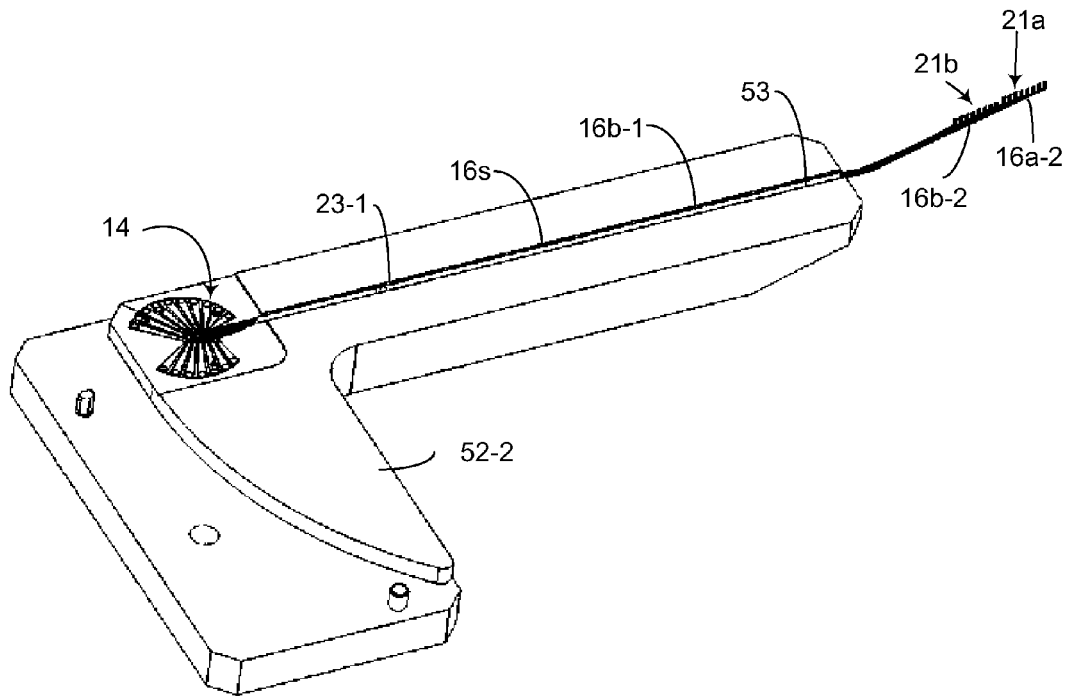
Figure 17F:
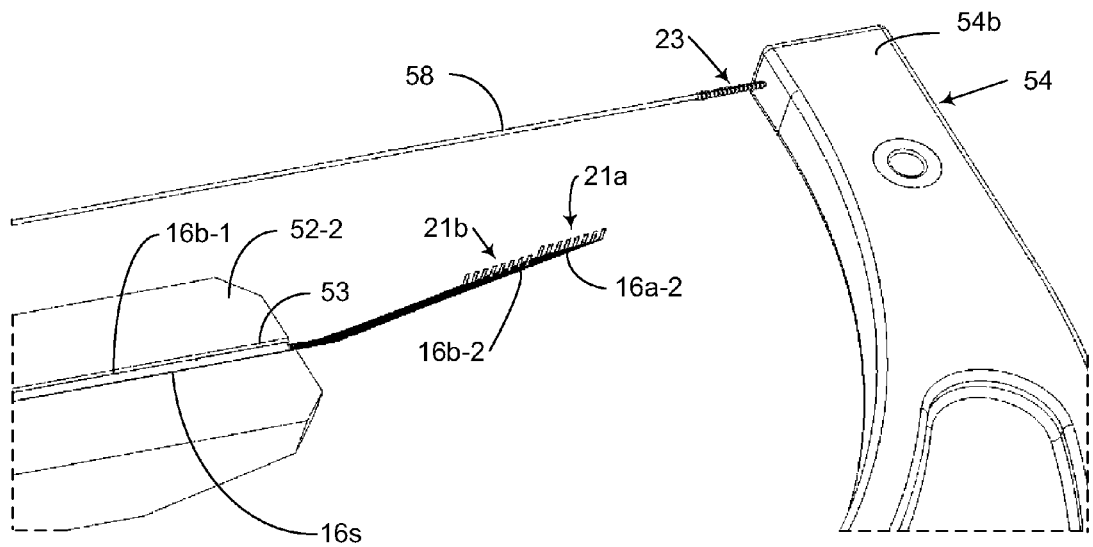
Figure 17G:
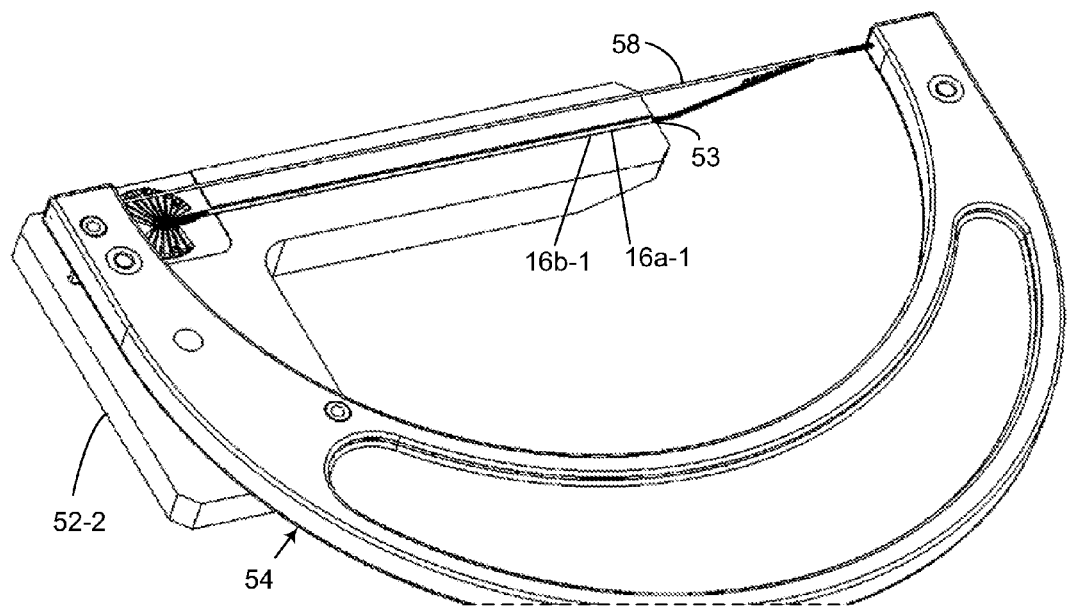
Figure 17H:
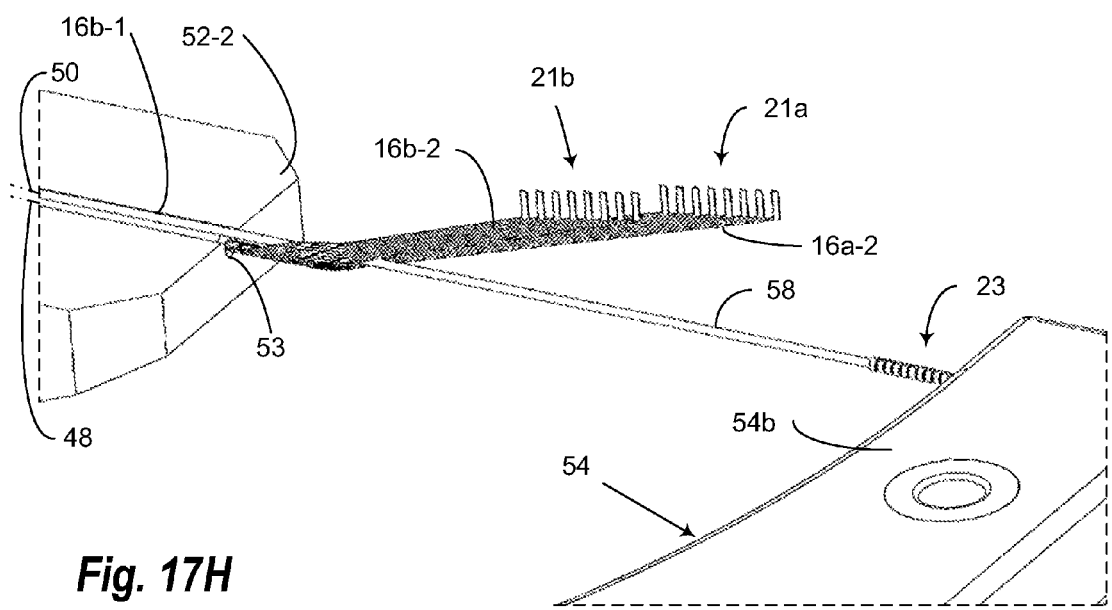
Figure 17I:
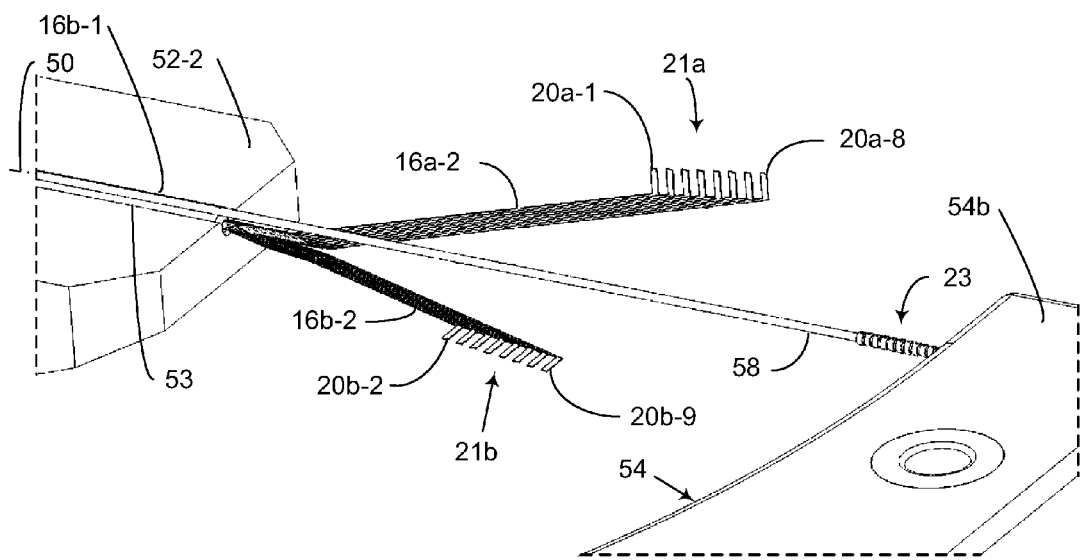
Figure 17J:
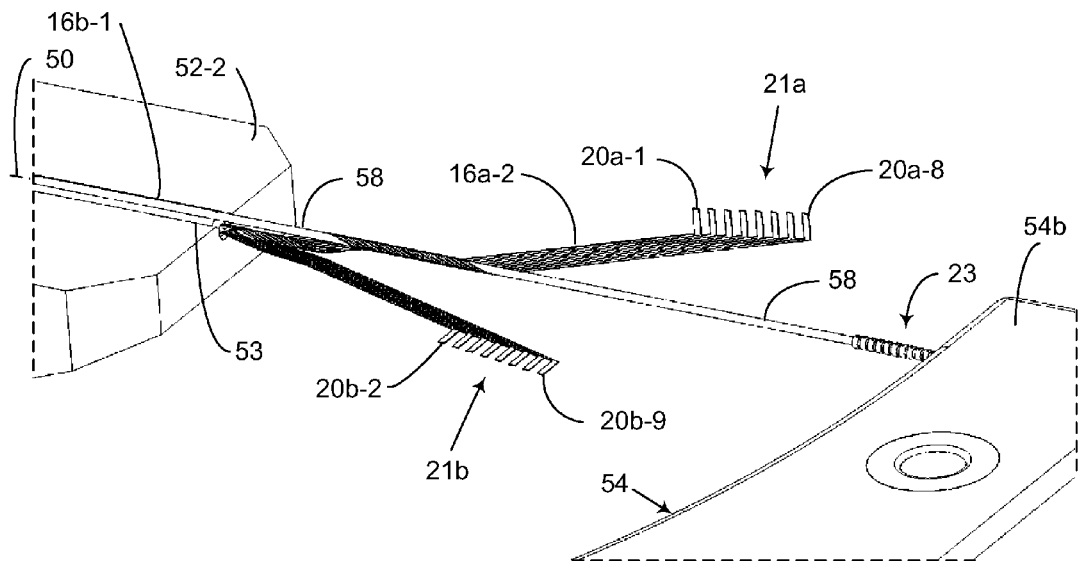
Figure 17K:
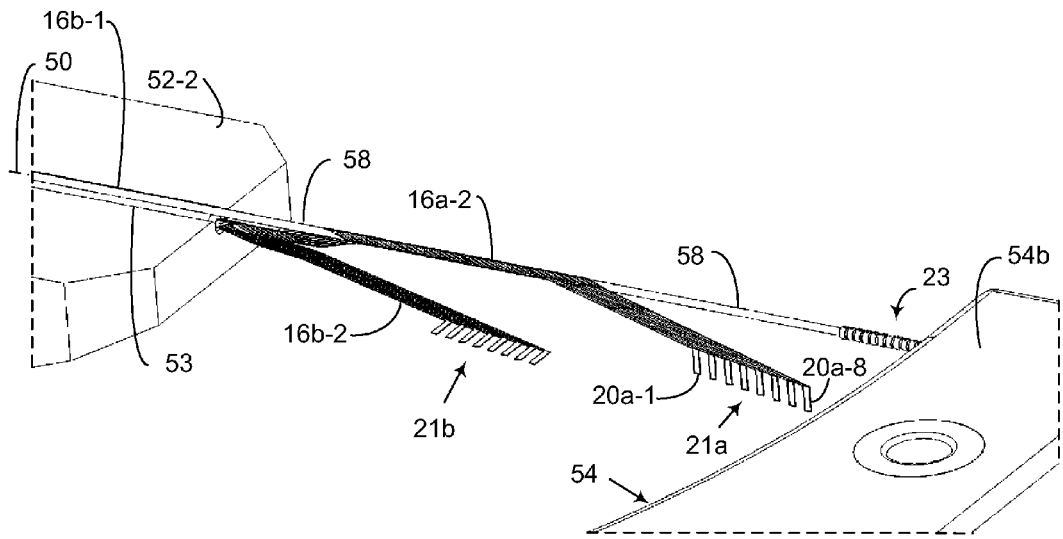
Figure 17L:
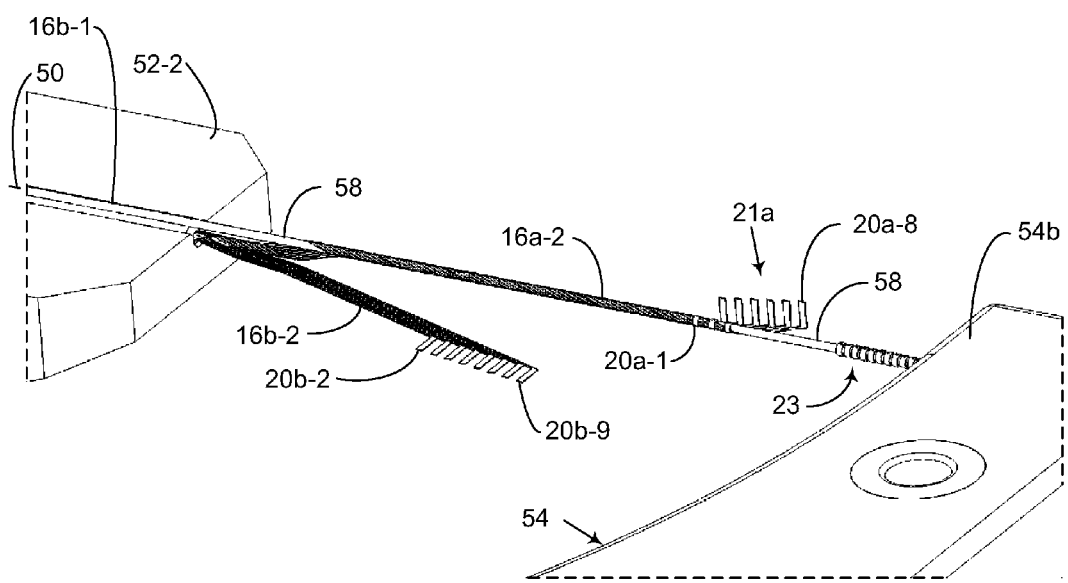
Figure 17M:
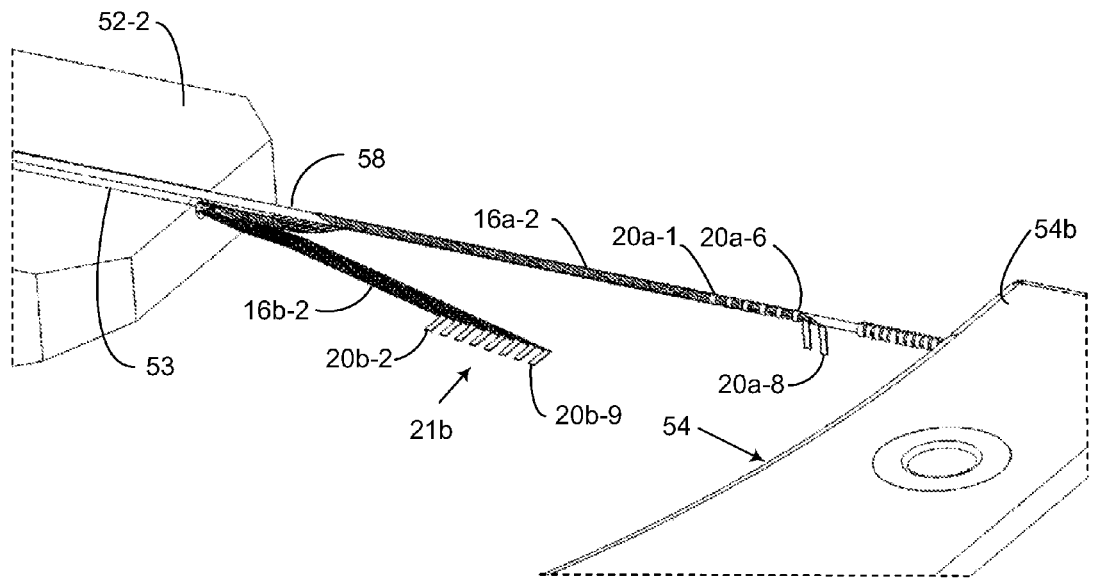
Figure 17N:
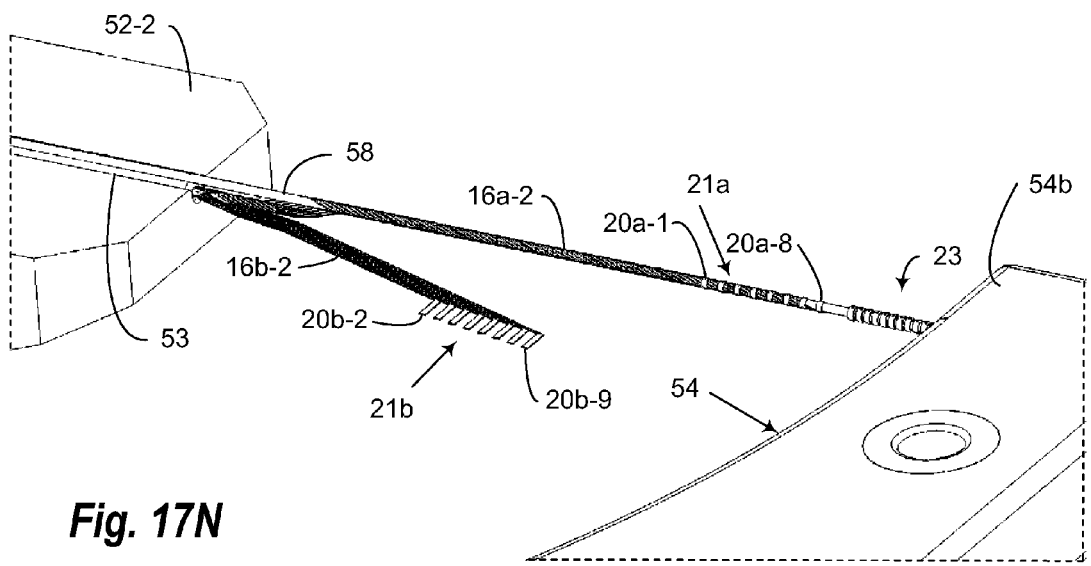
Figure 17O:
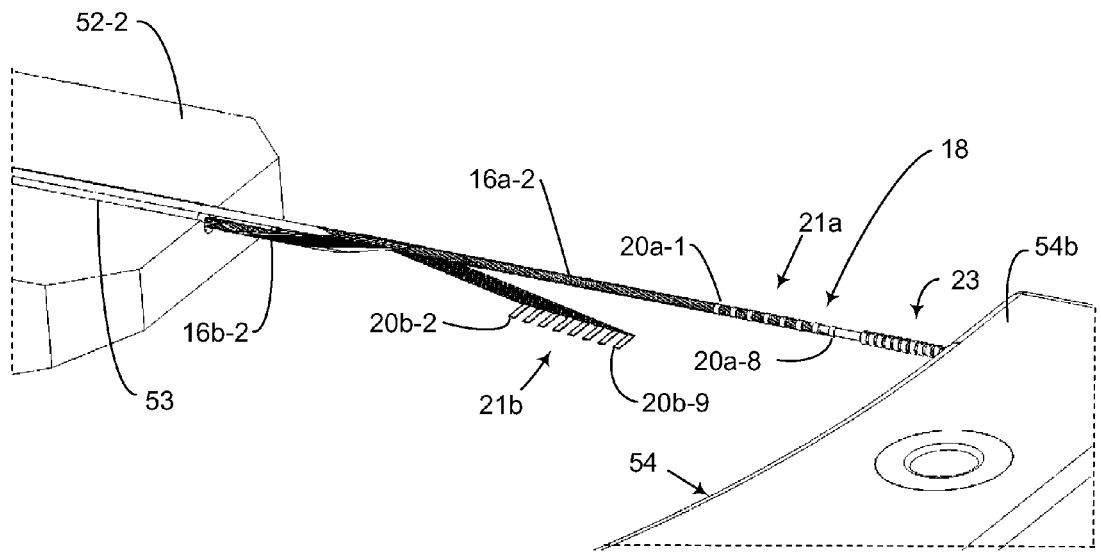
Figure 17P:
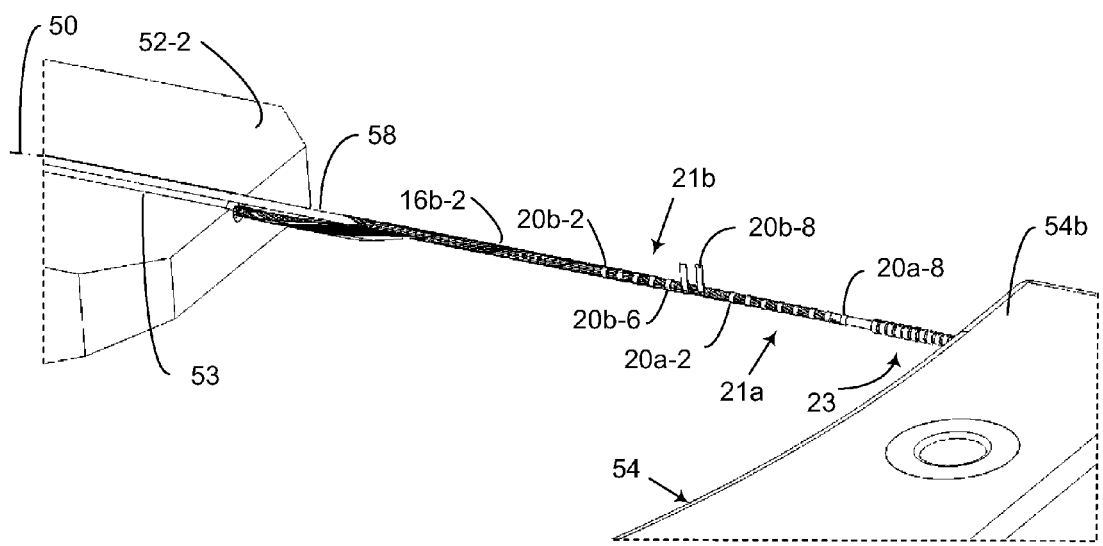
Figure 17Q:
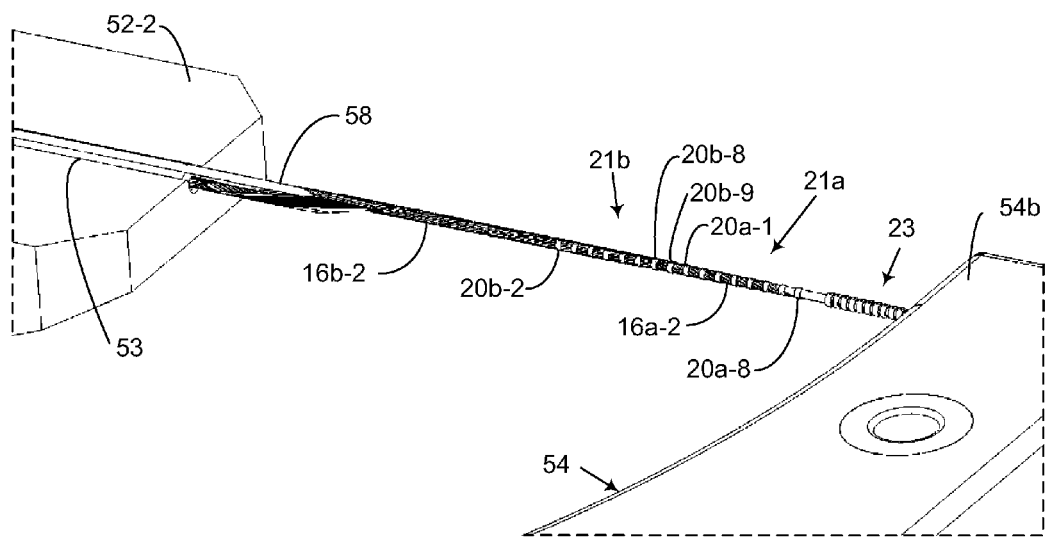
Figure 17R:
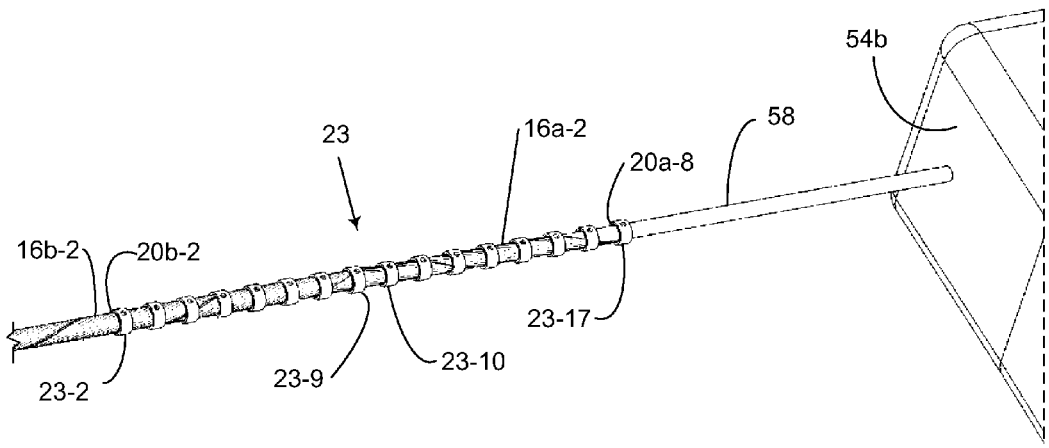
Figure 18A:
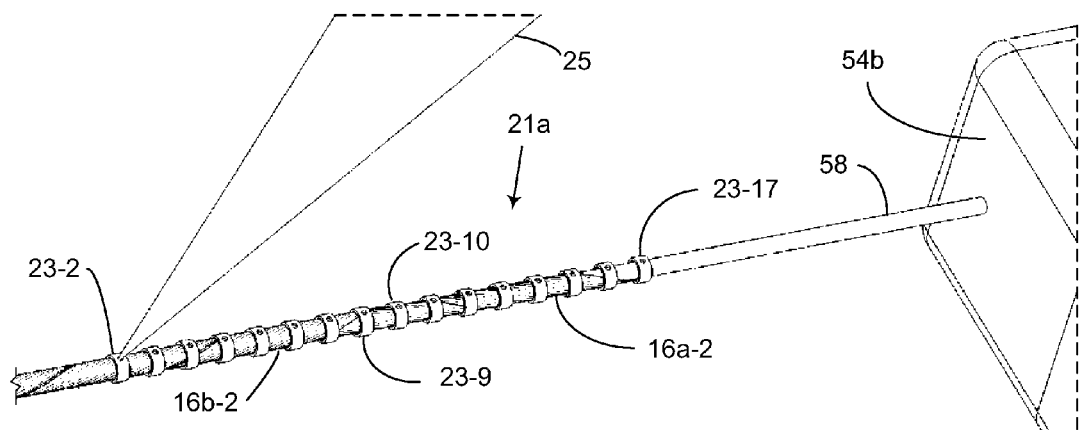
Figure 18B:
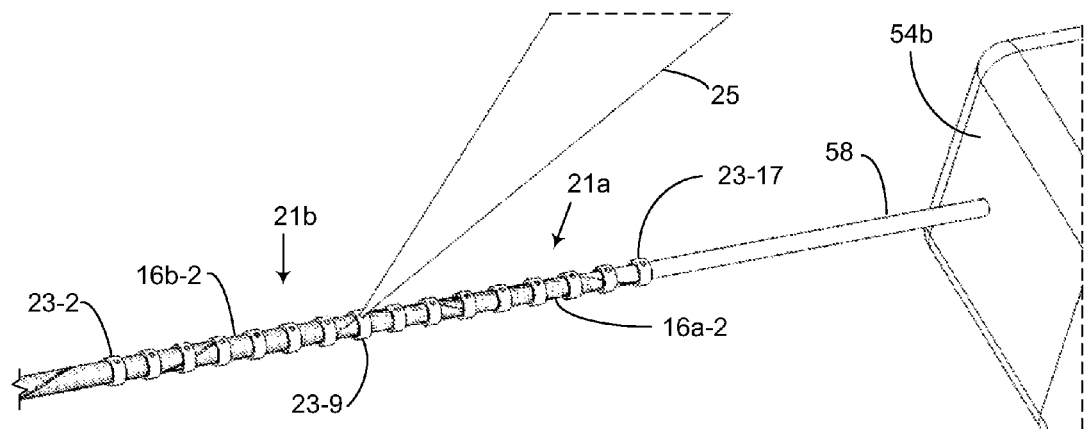
Figure 19A:
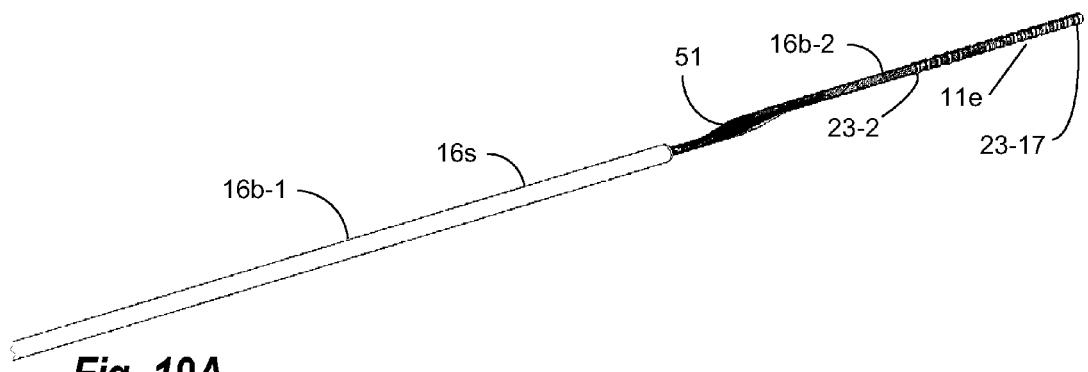
Figure 19B:
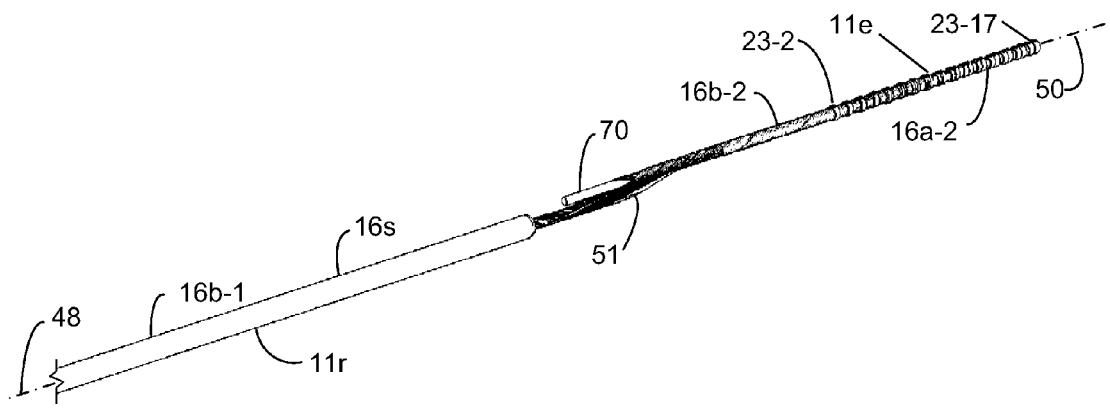
Figure 19C:
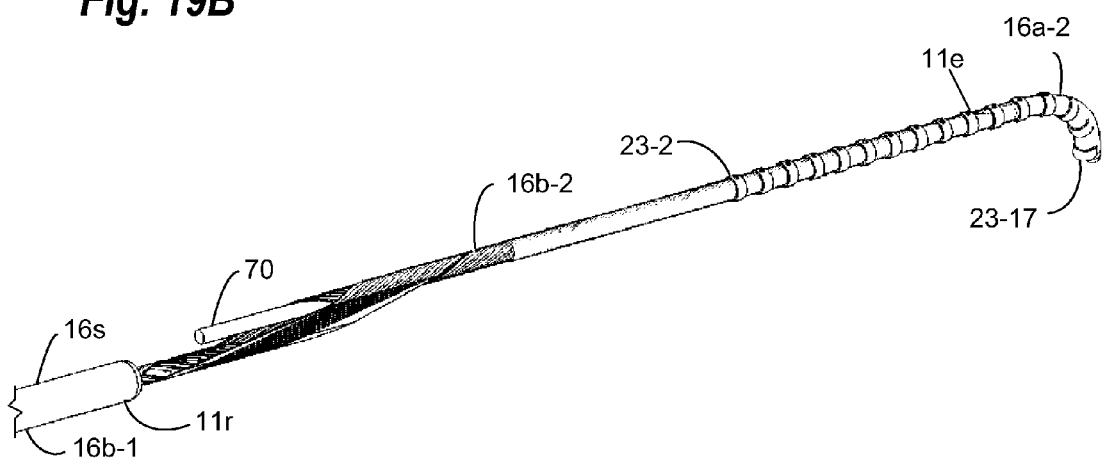
Figure 19D:
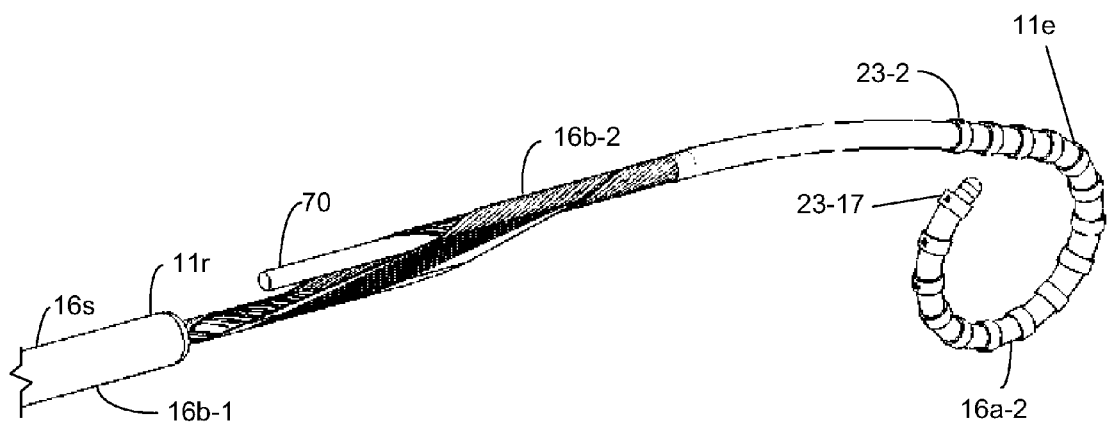
Figure 20A:
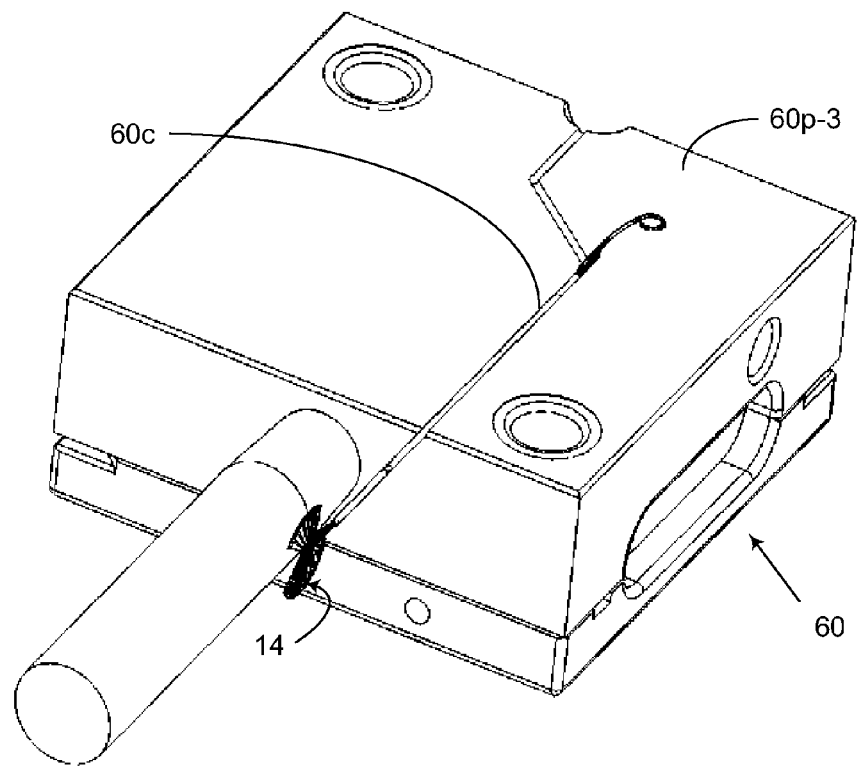
Figure 20B:
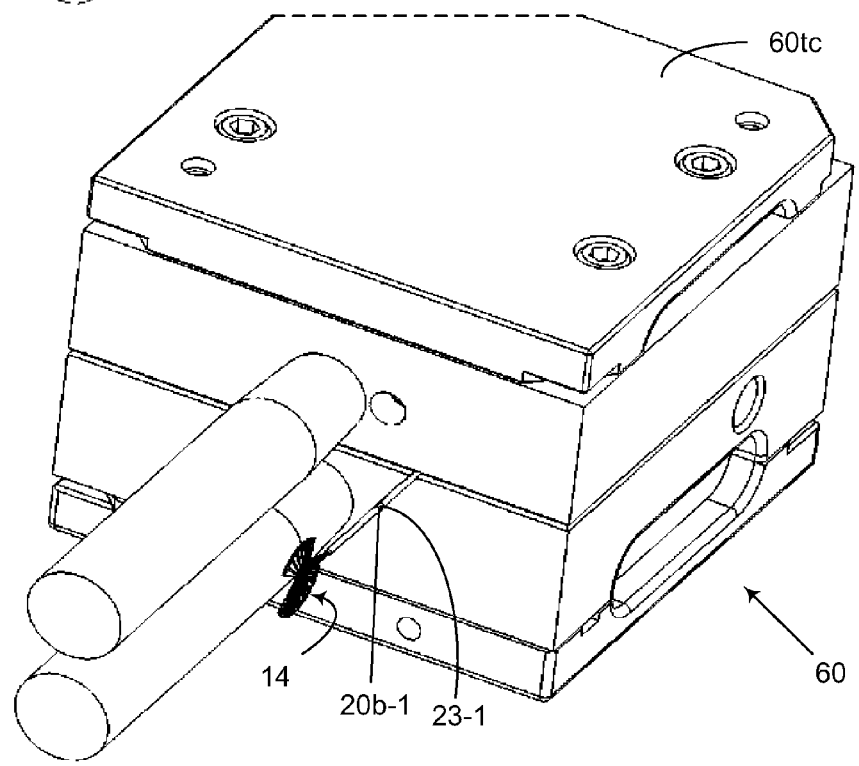
Figure 20C:
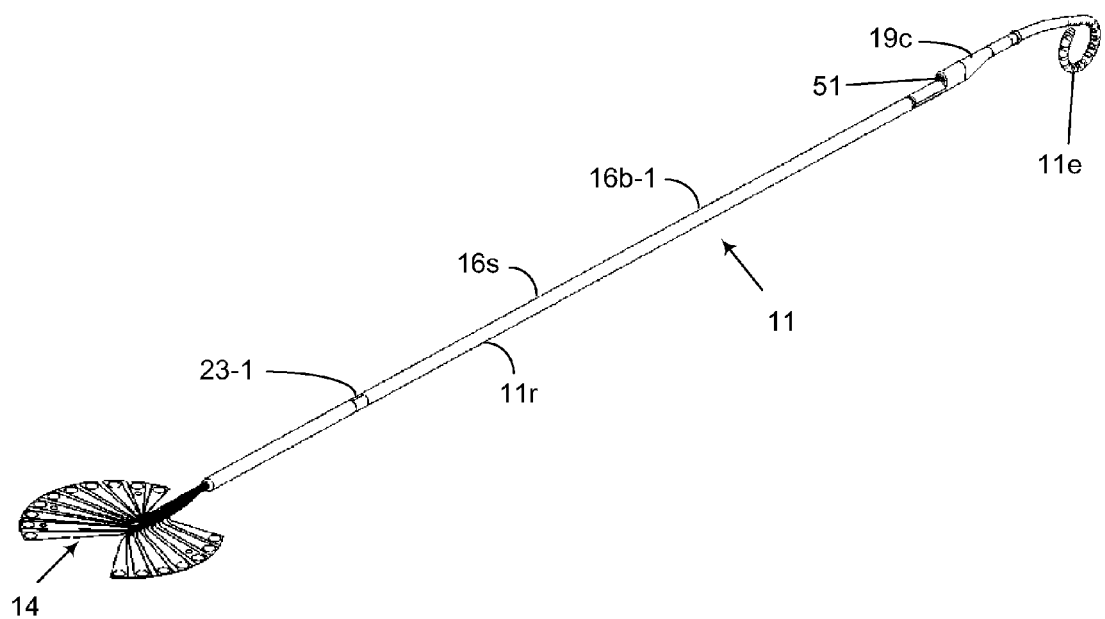
Figure 20D:
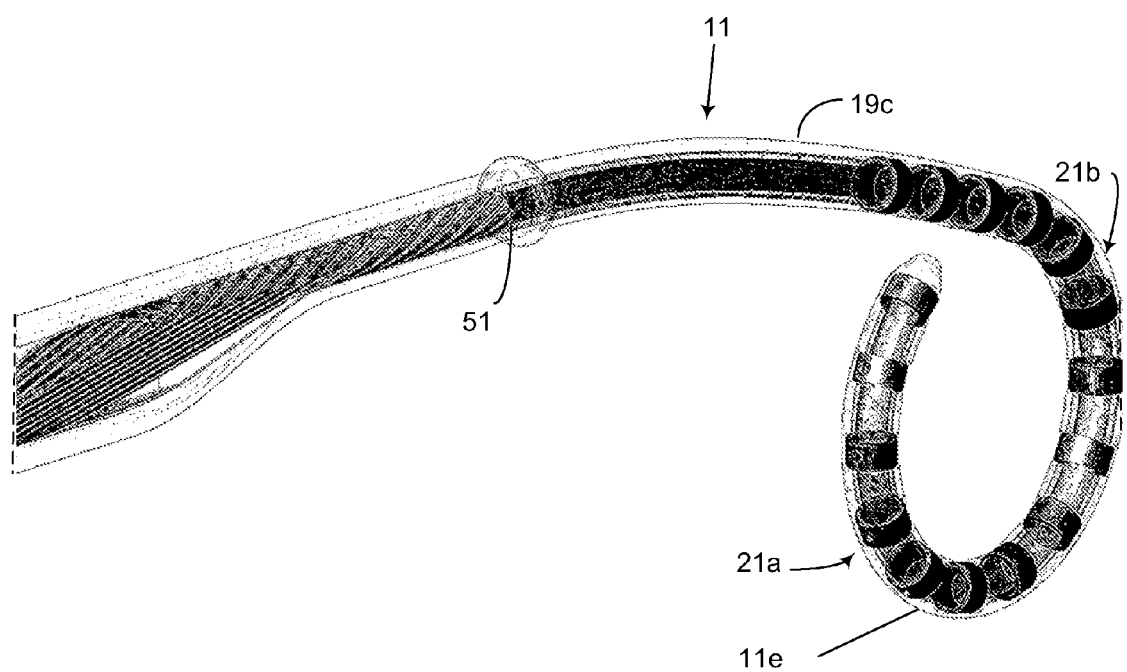

FIG. 4C diagrammatically depicts the laser cutting of first and second flat multi-conductor microcircuits from the metallic ribbon;

FIG. 4D depicts the outline of the first and second microcircuits laser machined within the metallic ribbon each including a head portion comprising a flat multi-conductor fan-shaped head portion with spaced exposed circuit attachment pads and a flat elongated multi-conductor tail portion with longitudinally-spaced, laterally-extending ring electrode receiving pads;

FIG. 4E is an enlarged view of the head portions and adjacent tail portions of the first and second microcircuits;

FIG. 4F shows nine laterally spaced longitudinally extending conductors machined in the tail portion of the second flat microcircuit within the circle 4F in FIG. 4E;

FIG. 4G is an enlarged view of forward ends of the tail portions of the first and second microcircuits;

FIG. 4H shows eight laterally spaced longitudinally extending conductors machined in the tail portion of the first flat microcircuit within the circle 4H in FIG. 4G;

FIG. 4I is an enlarged cross-sectional perspective of the eight conductors shown in FIG. 4H along the line 4I-4I depicting the internal construction of the tail portions after the laser machining thereof from the metallic ribbon secured to the film substrate;

FIGS. 5A-5G and 6A-6D depict the lamination of the first and second microcircuits between the first film substrate and a second film substrate pursuant to step 4 of the process of FIG. 1;

FIG. 5A shows the film vacuum support apparatus of FIG. 2 with an open rectangular top filler frame above the support apparatus;

FIG. 5B shows the top filler frame on the support apparatus;

FIG. 5C shows the second film substrate extending from a roll, over and above the top filler frame;

FIG. 5D shows the second film substrate on a top of the film support apparatus;

FIG. 5E shows excess film trimmed from the second film substrate and the substrate seated on the top filler frame and removed from the film support apparatus;

FIG. 5F shows the carrier and first film substrate of FIG. 4D inverted over the top filler frame and second film substrate of FIG. 5E;

FIG. 5G shows the carrier facing upward with the second film substrate between the frame and the carrier;

FIG. 6A shows the carrier and frame supporting the second film substrate on the bottom platen of the open laminating press previously illustrated in FIG. 3A;

FIG. 6B shows the laminating press of FIG. 6A in a closed condition applying heat and pressure to the second film substrate;

FIG. 6C shows the open press exposing the carrier, frame, and second film substrate;

FIG. 6D shows the carrier and frame removed from the press and the second film substrate covering and bonded to upper surfaces of the first and second microcircuits formed in the metallic ribbon on the first film substrate;

FIGS. 7A-7H depict the exposing of the electrode receiving pads and circuit attachment pads pursuant to step 4a of the process of FIG. 1;

FIG. 7A shows the inverted carrier and frame over the vacuum chuck of FIGS. 4A-4D for laser machining of bottom surfaces of the first film substrate to expose bottom surfaces of the electrode receiving pads and circuit attachment pads;

FIG. 7B illustrates the laser ablation of the bottom surface of the first film substrate to expose the bottom surfaces of the electrode receiving pads and circuit attachment pads of the first and second microcircuits previously machined in the metallic ribbon attached to an upper surface of the first film substrate;

FIG. 7C is an enlarged illustration of the laser exposed bottom surfaces of circuit attachment pads and a reference electrode receiving pad of the second microcircuit;

FIG. 7D is an enlarged showing of the exposed bottom surfaces of the electrode receiving pads adjacent forward ends of the first and second microcircuits;

FIG. 7E depicts the laser ablation to expose upper surfaces of the circuit attachment pads of the head portions of the microcircuits;

FIG. 7F shows the carrier on the vacuum chuck with upper surfaces of the circuit attachment pads of the microcircuits being exposed;

FIG. 7G is a cross-section the tail portion of one of the microcircuits illustrating the laser cutting of tail portions of the microcircuits and the flow of insulating adhesive of the first and second film substrates between and over adjacent conductors that occurred during the lamination of the first and second film substrates;

FIG. 7H is an enlarged showing of a portion of the cross-section of FIG. 7G;

8A-8G depict the excising of the first and second microcircuits from the first and second film substrates pursuant to step 5 of the process of FIG. 1;

FIG. 8A is a top view of the carrier with the backing of the second film substrate covering all of the first and second microcircuits formed in the metallic ribbon on the upper surface of the first film substrate except the exposed tops of the circuit attachment pads in the head portions of the microcircuits;

FIG. 8B illustrates the excising of the laminated first and second microcircuits from the carrier leaving the backing of the first film substrate within the carrier;

FIG. 8C is a top view of the excised first and second laminated microcircuits illustrating the exposed tops of the circuit attachment pads of the head portions of the backing covered first and second microcircuits;

FIG. 8D illustrates the removal of the exposed backing of the second film substrate of the first microcircuit;

FIG. 8E illustrates the removal of the exposed backing of the second film substrate of the second microcircuit;

FIG. 8F is an enlarged top view of head portions of microcircuits after removal of the backing of the second film substrate illustrating the exposed circuit attachment pads and the insulated upper surfaces of the remainders of the head portions of the microcircuits following removal of the backing;

FIG. 8G is an enlarged view of forward end of the tail portions of microcircuits after removal of the backing of the second film substrate illustrating the insulated upper surfaces of the electrode receiving pads and remainders of the tail portions of the microcircuits following removal of the backing, only the bottom surfaces of the electrode receiving pads being exposed as illustrated in FIG. 7D;

FIG. 8H shows flat microcircuits including head portions and tail portions;

FIGS. 9A-9J depict the helical wrapping of the tail portions of the first and second microcircuits in opposite direction pursuant to step 6 of the process of FIG. 1 for a first preferred embodiment of the present invention, namely a J-style cochlear electrode;

FIG. 9A shows a fan-shaped head portion of the second microcircuit clamped to a support base for a tooling bow with the tail portion thereof including its reference electrode receiving pad extending forward at an acute angle from the tail portion;

FIG. 9B shows a complementary fan-shaped head portion of the first microcircuit clamped to the support base for the tooling bow adjacent the fan-shaped head portion of the second microcircuit with its associated tail portion extending over and away from the tail portion of the second microcircuit;

FIG. 9C shows the tooling bow secured to its support base with a tensioned wire extending through one end of the bow over and between the microcircuits toward an opposite end of the bow;

FIG. 9D shows a reference ring electrode and a series of smaller ring electrodes on a forward end of the tensioned wire adjacent its connection to an opposite end of the bow;

FIG. 9E shows the tensioned wire extending along a longitudinally extending axis between the longitudinally extending tail portions of the first and second microcircuits under the tail portion of the first microcircuit and over the tail portion of the second microcircuit each of which extend longitudinally at acute angles from the tensioned wire;

FIG. 9F depicts a helical wrapping of the tail portion of the first microcircuit adjacent its associated head portion in a clockwise direction forward and around the longitudinally extending tensioned wire;

FIG. 9G depicts the continued forward helical clockwise wrapping of the tail portion of the first microcircuit until the electrode receiving pads thereof successively encircle the insulated outer surface of the helically wrapped tail portion with the bottom surfaces thereof exposed and forming a first series of longitudinally spaced metallic electrode receiving pads adjacent a forward end of the completely helically wrapped first microcircuit;

FIG. 9H shows the tooling bow with its tensioned wire supporting the helically wound tail portion of the first microcircuit with the tail portion of the second microcircuit ready for its helical wrapping over and forwardly along the helically wrapped tail portion of the first microcircuit and the longitudinal axis thereof;

FIG. 9I illustrates the helical wrapping of the a portion of the tail portion of the second microcircuit adjacent its associated head portion in a counterclockwise direction over and forward along the helically wrapped tail portion of the first microcircuit with the reference electrode receiving pad of the second microcircuit encircling the insulated outer surface of the of the helically wrapped second microcircuit with its bottom surface forming an exposed metallic reference electrode receiving pad;

FIG. 9J depicts the continued forward helical counterclockwise wrapping of the tail portion of the second microcircuit until the electrode receiving pads thereof successively encircle the insulated outer surface of the helically wrapped tail portion with the bottom surfaces thereof exposed and forming a second series of longitudinally spaced metallic electrode receiving pads immediately adjacent the first series formed by the helically wrapped electrode receiving pads of the first microcircuit;

FIGS. 10A-10C show the mounting and electrical connection of ring electrodes on and to the exposed ring electrode receiving pad pursuant to step 7 of the process of FIG. 1;

FIG. 10A depicts the reference ring electrode on the exposed metallic reference electrode receiving pad and ring electrodes on each of the exposed ring electrode receiving pads in the first and second series;

FIG. 10B depicts the reference electrode being electrically connected to and secured on the reference electrode receiving pad;

FIG. 10C depicts the ring electrodes being electrically connected to and secured on the electrode receiving pads of the first and second series;

FIGS. 11A-11J illustrate the shaping and overmolding of the cochlear electrode array comprising the first preferred embodiment of the present invention pursuant to step 8 of the process of FIG. 1;

FIG. 11A shows the tooling bow supporting the helically wrapped first and second microcircuits on the tensioned wire with ring electrodes welded to the electrode receiving pads and a portion of helically wrapped tail portions of the microcircuits between the head portions and the second series of electrode receiving pads positioned in a channel of a lower support plate of a conventional overmolding apparatus;

FIG. 11B shows the overmolding apparatus of FIG. 11A with its top cover in place over the portion of the helically wrapped tail portions of the microcircuits between the exposed head portions and the second series of electrode receiving pads ready to overmold sections on both sides of the ground electrode with a polymeric insulating material such as silicone;

FIG. 11C depicts the tooling bow and overmolded microcircuits removed from the overmolding apparatus with the tensioned wire being removed from the tooling bow allowing the overmolded microcircuits comprising the cochlear electrode array to be removed from the tooling bow;

FIG. 11D shows the cochlear electrode array of FIG. 11C removed from the tooling bow;

FIG. 11E shows an exposed forward end portion of the cochlear electrode array of FIG. 11D pre-formed in the shape of a "J";

FIG. 11F shows the J-shaped forward end of the electrode array positioned in a J-shaped channel of a lower support plate of the overmolding apparatus;

FIG. 11G shows the overmolding apparatus of FIG. 11F with its top cover in place ready to overmold the J-shaped forward end with a polymeric insulating material such as silicone, the top plate including bottom features that block the placing of polymer over the first and second series of longitudinally spaced ring electrodes;

FIG. 11H shows the overmolded J-style cochlear electrode array comprising the first preferred embodiment of the present invention being removed from the overmolding apparatus;

FIG. 11I is a slightly enlarged view of the J-style cochlear electrode of FIG. 11H showing the longitudinally spaced exposed ring electrodes of the J-style cochlear electrode of the present invention and a small polymeric electrode array insertion pad at a junction of the longitudinally extending helically wrapped portion of the tail of the electrode array formed by polymer flowing to a corresponding junction of the J-shaped channel and a side channel in the lower support plate of the overmolding apparatus as depicted in FIG. 11F, the insertion pad being utilized by a surgeon as an instrument or finger pressure point during the insertion of the electrode array into the cochlea of a patient;

FIG. 11J is an enlarged view of the forward end of the J-style cochlear electrode comprising a first preferred embodiment of the present invention;

FIGS. 12A-20C illustrate the processing of the first and second flat microcircuits into a spiral-style cochlear electrode array comprising a second preferred embodiment of the present invention pursuant to steps 6 through 8 of the process of FIG. 1;

FIG. 12A shows the fan-shaped head portion of the second microcircuit above the base support for the tooling bow;

FIG. 12B shows the head portion of FIG. 12A on and secured to the base support with its associated tail portion extending longitudinally forward over and from the base support;

FIG. 13A shows the fan-shaped head portion of the first microcircuit above the base support and the head portion of the second microcircuit secured thereto as shown in FIG. 12B with its associated tail portion extending longitudinally forward from the base support;

FIG. 13B shows the head portion of the first of microcircuit secured to the base support adjacent the head portion of the second microcircuit with the tail portion of the first microcircuit extending longitudinally over and forward beyond the tail portion of the second microcircuit as illustrated in FIG. 13C;

FIG. 14A shows the tooling bow of FIG. 9C secured to the base support with the tensioned wire of the tooling bow extending on a first longitudinal axis over the fan-shaped head portions of the first and second microcircuits secured to the base support and over and between the tail portions of the first and second microcircuits as they extend longitudinally forward from their associated head portions with their associated tail portions extending forward and away from each other and the tensioned wire of the tooling bow extending through one end of the bow over the microcircuits to an opposite end of the bow;

FIGS. 14B and 14C show an initial helical wrapping of a portion of the tail portion of the first microcircuit adjacent its associated head portion in a first direction (e.g. clockwise) on and around a first longitudinal axis defined by the tensioned wire toward a location that is (i) forward of where the reference electrode receiving pad of the second microcircuit will be subsequently helically wrapped during an initial helical wrapping of the tail portion of the second microcircuit in an opposite direction over the initially wrapped tail portion of the first microcircuit and (ii) rearward of the second series of ring electrode receiving pads;

FIGS. 14D-14G show the initial helical wrapping of the tail portion of the second microcircuit adjacent its head portion in an opposite direction (e.g., counterclockwise) on and forward around the initially wrapped tail portion of the first microcircuit to the location forward of the helically wrapped reference electrode receiving pad;

FIGS. 15A and 15B show the mounting of a longitudinally split reference ring electrode on the exposed reference electrode receiving pad encircling the helically wrapped tail portions of the first and second microcircuits and the closing of the reference electrode as by laser welding;

FIG. 15C shows reference ring electrode after it has been secured and electrically connected upon and to the exposed reference electrode receiving pad;

FIG. 16A shows the tooling bow and base support inverted and the helically wrapped initial tail portions of the first and second microcircuits mounted in a channel in the base of an overmolding apparatus with the electrode receiving pads of the tail portions extending beyond the apparatus;

FIG. 16B shows the overmolding apparatus of FIG. 16A with its top cover in place ready to overmold the helically wrapped initial portions of the first and second microcircuits with a polymeric material such as silicone, the top cover including features that block the placing of polymer over the reference ring electrode;

FIG. 17A shows the tooling bow removed from the overmolding apparatus of FIGS. 16A and 16B with the helically wrapped initial tail portions of the first and second microcircuits overmolded with a polymeric material and remaining forward portions of the first and second microcircuits including the first and second series of ring electrode receiving pads of the first and second series extending forward of the overmolded portions thereof;

FIG. 17B shows the first and second microcircuits of FIG. 17A removed from the tooling bow;

FIG. 17C shows the first and second microcircuits of FIG. 17B over a second base support for the tooling bow including an open longitudinally extending top channel;

FIG. 17D shows overmolded initially wrapped tail portions of the first and second microcircuits of FIG. 17B lowered into the top channel in the second base support with the head portions of the microcircuits secured in place rearward of the channel;

FIG. 17E shows overmolded initially wrapped tail portions of the first and second microcircuits of FIG. 17B in the open longitudinally extending top channel in the second base support with the remaining forward ends of the microcircuits extending forward of the second base support;

FIG. 17F shows the tooling bow with its tensioned wire supporting a series of ring electrodes located above the second support base;

FIG. 17G shows the tooling bow in a lowered position with its tensioned wire above and offset slightly from the overmolded initially wrapped tail portions of the first and second microcircuits within the top channel in the second base support, and the tensioned wire of the tooling bow laterally offset from and extending longitudinally along a second axis above and parallel to the channel and the overmolded initially wrapped tail portions of the microcircuits contained therein and also showing a series of ring electrodes supported on an end of tensioned wire adjacent its connection to the tooling bow;

FIGS. 17H and 17I show the tensioned wire of the tooling bow offset along the second longitudinal axis above and parallel to the top channel, the overmolded portions of the first and second microcircuits in the top channel, and forward ends of the remaining tail portions of the microcircuits;

FIGS. 17J-17N show the remaining tail portion of the first microcircuit including its electrode receiving pads as it is separately helically wrapped in the first or clockwise direction on the laterally offset second longitudinal axis defined by the tensioned wire toward the series of ring electrodes carried by the tensioned wire of the tooling bow, the laterally spaced helically wrapped remainder of the first microcircuit defining an internal stylet lumen extending along the second longitudinal axis offset from the first longitudinal axis, FIG. 17N depicting the electrode receiving pads of the first microcircuit encircling the insulation covering of the conductors in the tail portion thereof and the exposed bottom surfaces of the electrode receiving pads forming the first series of metal exposed ring electrode receiving pads immediately adjacent the series of ring electrodes carried by the tensioned wire;

FIGS. 17O-17Q show the remainder of the tail portion of the second microcircuit including its electrode receiving pads as it is separately helically wrapped in a second or counterclockwise helical direction on the laterally offset second longitudinal axis defined by the tensioned wire and over and forward along the helically wrapped remainders of the tail portions of the first microcircuit toward the first series of ring electrode receiving pads thereof, FIG. 17Q depicting the electrode receiving pads of the second microcircuit encircling the insulation covering of the tail portion thereof and the exposed bottom surfaces of the electrode receiving pads forming the second series of exposed metal ring electrode receiving pads immediately adjacent the first series of ring electrode receiving pads of the helically wrapped remainders of the tail portion of the first microcircuit;

FIG. 17R illustrates the placement of the ring electrodes carried by the tensioned wire on each electrode receiving pad in the first and second series of electrode receiving pads;

FIGS. 18A and 18B depict the securing and electrical connection of different ones of the ring electrodes on and to their associated electrode receiving pads as by laser welding;

FIG. 19A illustrates the helically wrapped tail portions of the cochlear electrode array removed from the tooling bow following the electrical connection of the ring electrodes as depicted in FIG. 18B and showing the helically wrapped remainders of the tail portions of the first and second microcircuits laterally off-set from the overmolded initially helically wrapped tail portions of the first and second microcircuits to form a stylet lumen;

FIG. 19B shows the placement of a plastic rod into the stylet lumen of FIG. 19A;

FIGS. 19C and 19D show the shaping of a forward end of the helically wrapped microcircuits into an inward spiral; and FIGS. 20A-20D depict the overmolding of the forward end of the helically wrapped microcircuits shown in FIGS. 19C and 19D pursuant to step 8 of the process of FIG. 1, FIG. 20A showing the forward end of the helically wrapped microcircuits of FIG. 19D mounted in a channel in a base of an overmolding apparatus with the head portions and adjacent tail portions exposed, FIG. 20B showing the overmolding apparatus of FIG. 20A with its top cover in place ready to overmold the forward end portion of the helically wrapped first and second microcircuits, FIG. 20C showing the spiral-style cochlear electrode array of the present invention removed from the overmolding apparatus, and FIG. 20D being an enlarged view of the forward end of the overmolded spiral-style cochlear electrode of FIG. 20C comprising a second preferred embodiment of the present invention.

DETAILED DESCRIPTION OF INVENTION

Basically, and as shown in FIGS. 11I and 20C, the process of the present invention depicted in FIG. 1 is intended to efficiently produce improved helically wound microcircuit cochlear electrode arrays, including preferred J-style and spiral-style cochlear electrode arrays designated by the numerals 10 and 11, respectively.

As illustrated in FIGS. 4D-4G and 8H, the cochlear electrode arrays 10 and 11 each comprise first and second flat microcircuits 12a and 12b. The flat microcircuits 12a and 12b, in turn, respectively include associated multi-conductor head portions 14a and 14b and tail portions 16a and 16b.

As illustrated in FIGS. 4D and 4E, the head portions 14a and 14b may comprise complementary multi-lobe fan-shaped sections 14c which, when placed adjacent each other as depicted in FIGS. 9B and 13B, combine to form a fan-shaped head portion 14 for each of the microcircuit cochlear electrode arrays 10 and 11. As further illustrated in FIG. 4E, lobes 14I of the head portions 14a and 14b are each covered with insulating material 14m, and each includes a top and bottom exposed circuit attachment pad 15 that is electrically connected to a different one of a plurality of longitudinally extending laterally spaced electrical conductors 18a and 18b respectively formed in the tail portions 16a and 16b as illustrated in FIGS. 4F and 4H.

Specifically, FIG. 4H shows a segment of the tail portion 16a wherein eight laterally spaced longitudinally extending flat electrical conductors 18a-1 through 18a-8 are shown covered with an insulating material 19a as depicted in FIGS. 7G and 7H. Likewise, FIG. 4F shows a segment of the tail portion 16b wherein nine laterally spaced longitudinally extending electrical conductors 18b-1 through 18b-9 are shown covered with an insulating material 19b as depicted for the conductors 18a-1 through 18a-8 in FIG. 7H.

As also depicted in FIGS. 4E, 4G, 8G, and 8H, respective ones of the conductors 18a-1 through and 18a-8 have flat, bottom surface exposed ring electrode receiving pads 20a-1 through 20a-8 each extending forward and laterally from a forward end portion thereof at an acute angle α of about 73 degrees to a longitudinal axis of the conductor from which it extends. Likewise, as depicted, respective ones of flat conductors 18b-1 through and 18b-9 have flat, bottom surface exposed ring electrode receiving pads 20b-1 through 20b-9 each extending forward and laterally from an end portion thereof at an acute angle of about 73 degrees to a longitudinal axis of the conductor from which it extends. Also, in the tail portion 16a of the first microcircuit 12a, the inner edge-most conductor 18a-1 of the longitudinally extending laterally spaced conductors 18a-1 through 18a-8 is relatively short compared to the progressively longer conductors 18a-2 through 18a-8. Also, as shown most clearly in FIG. 4G, in the tail portion 16b of the second microcircuit 12b, the inner edge-most conductor 18b-1 of the laterally spaced longitudinally extending conductors 18b-1 through 18b-9 is much shorter than its adjacent conductor 18b-2 and the remaining conductors 18b-3 through 18b-9 are progressively longer than the conductor 18b-2.

The process for forming the above-described multi-conductor microcircuits 12a and 12b is outlined in the process flow diagram of FIG. 1 as steps 1-5 and is illustrated more fully in FIGS. 2A through 8G. As indicated in FIG. 1, step 1 of the process is to secure and support a nonconductive film substrate 22. The film substrate 22 may be less than 25 microns thick, or about 4 to 7 microns thick, such as about 4 microns thick. As will be described further hereinafter and shown in FIG. 4I, film substrate 22 may comprise an adhesive layer upper surface 22u, which melts so that adhesive flows between the conductors 18a-1 through 18a-8 of the first microcircuit 12a and between the conductors 18b-1 through 18b-9 of the second microcircuit 12b during the lamination step 4 of the process depicted in FIG. 1. Also, the film substrate 22 may be provided with a thin "peel-off" backing 22b, such as a Kapton® polyimide film backing, allowing for easier handling and stabilizing of the film substrate 22 during the attachment of a flat metallic ribbon 24, such as platinum, to an upper surface 22u of the film substrate 22 in step 2 and during the machining of the first and second microcircuits 12a and 12b from the metallic ribbon 24 during step 3 of the process depicted in FIG. 1. The metallic ribbon 24 may be supplied in individual strips. Alternatively, the metallic ribbon 24 may be supplied in a continuous roll, and laminated to the film substrate 22 with adhesive using a continuous pinch-roller thermal/compression process. The laminated sheets are then cut to approximately 10.25" long×6" wide.

Figure 2A:
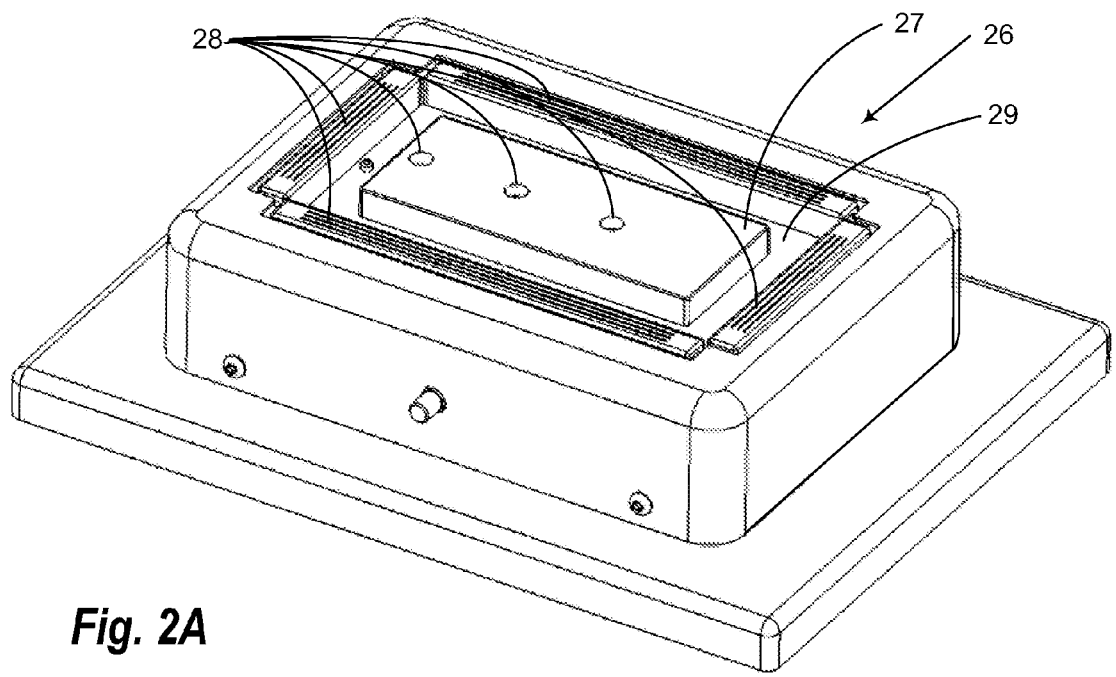
Figure 2B:
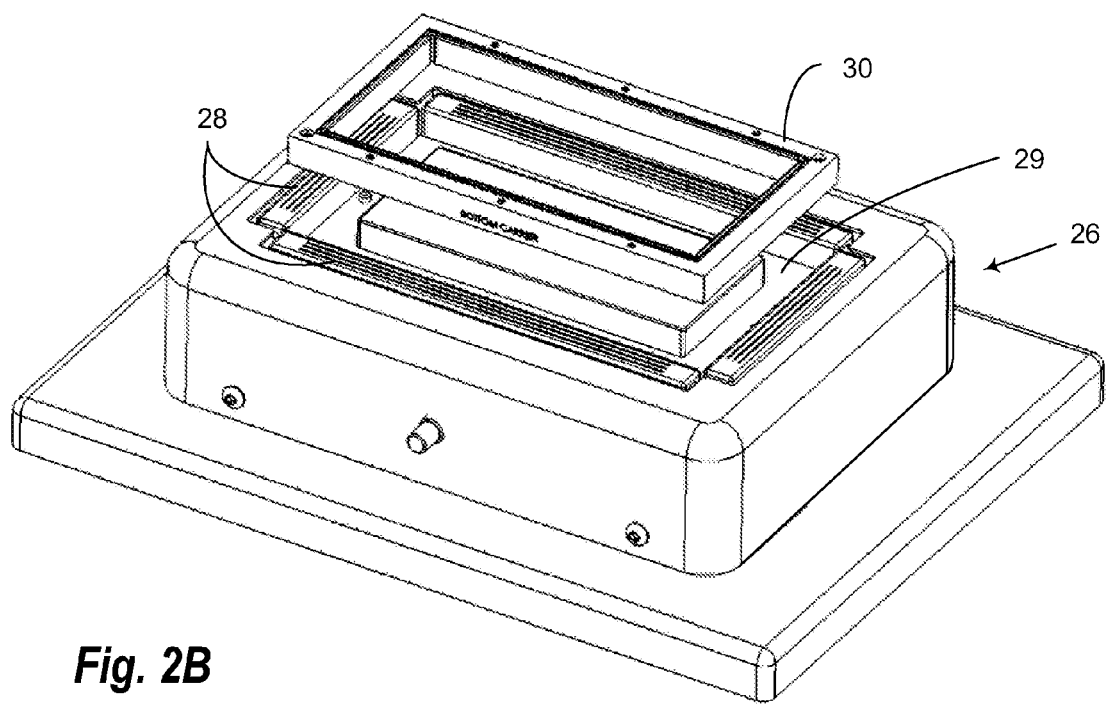
Figure 2C:
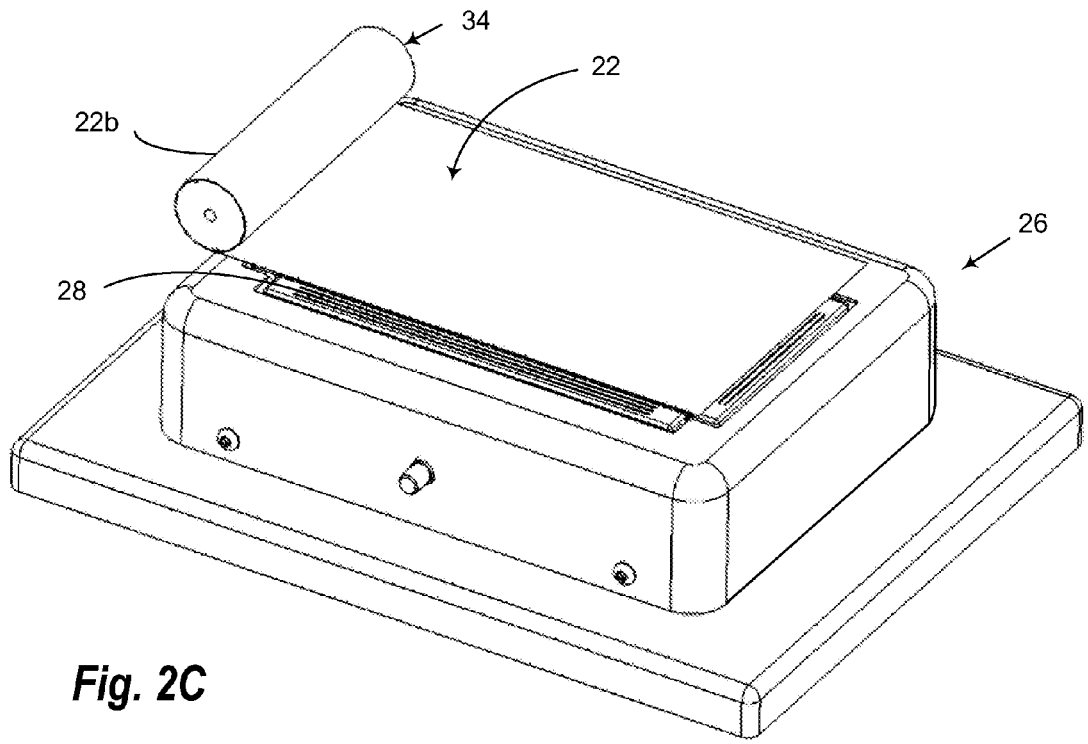

With regard to step 1, a film substrate vacuum support apparatus 26, such as depicted in FIG. 2A, may be employed to support and secure the film substrate 22 during the initial placement and attachment of the metallic ribbon 24 on and to the upper surface 22u of the film substrate pursuant to step 2 of the process depicted in FIG. 1 and during the placement of a second film substrate over a top surface of the metallic ribbon 24 preparatory to the lamination of the first and second microcircuits pursuant to step 4 of the process depicted in FIG. 1. As shown in FIG. 2A, a film substrate vacuum support apparatus 26 incorporates or is connected to a vacuum source and includes openings 28 in a flat top surface 27 for drawing air through the openings to the vacuum source to hold a film substrate on the flat top surface. The apparatus 26 is depicted as including a flat rectangular top channel 29 for receiving an open rectangular bottom frame 30 of a film carrier 32 utilized in the process steps of securing and supporting the nonconductive film substrate, the bottom frame 30 shown over the apparatus 26 in FIG. 2B and lowered into the rectangular top channel 29 in FIG. 2C. Also in FIG. 2C, a roll 34 of the nonconductive film substrate 22 is positioned adjacent an end of the film substrate vacuum support apparatus 26 shown in FIGS. 2A with the film extending over the open rectangular bottom frame 30 in the top channel 29. It should be noted that although the film is described herein as supported by a vacuum support, other means, such as magnets, may be used to clamp the film to a support fixture. Alternatively, the film may be clamped between two frames. As yet another alternative, the film may be pierced by a clamping device, such as screws, to hold the film in place for processing.

Figure 2D:
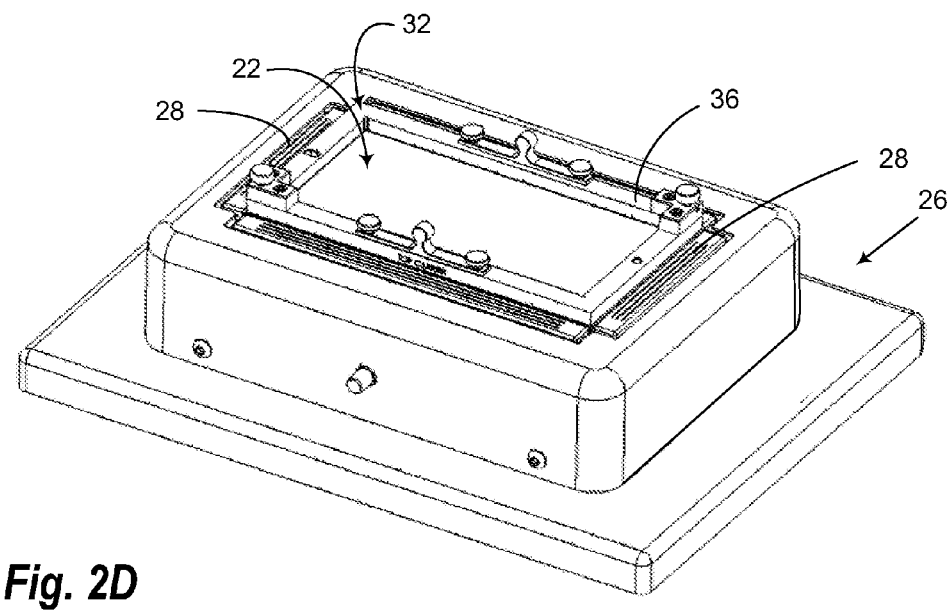
Figure 2E:
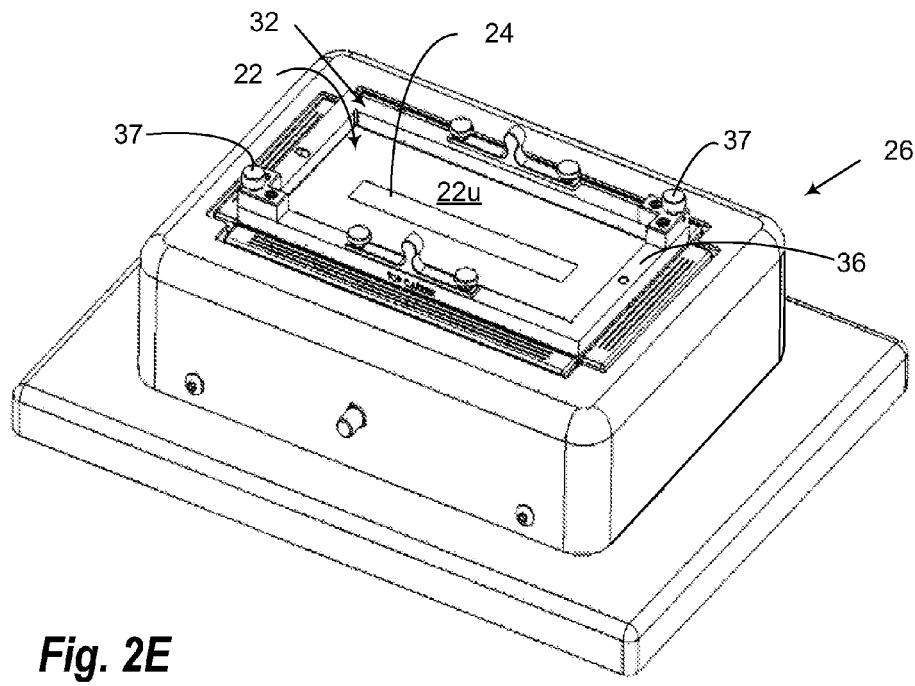

As represented in FIG. 2D, the film substrate 22 is moved downward onto the open bottom frame 30 within the channel 29 (shown in FIG. 2B) of the vacuum apparatus 26 with the backing 22b of the film substrate (shown in FIG. 2C) resting on the top of the lower frame and an open rectangular upper frame 36 of the film carrier 32 positioned above the top of the film substrate. As represented in FIG. 2E, the upper frame 36 of the film carrier 32 is lowered onto and secured to the top of the lower frame by attachment screws 37. As illustrated in FIG. 2E, this secures the film substrate 22 within the film carrier 32, allowing excess film outside the carrier to be removed and the metallic ribbon 24 to be securely placed on the upper surface 22u of the film substrate 22 thereby completing the securing and support of a first nonconductive film substrate pursuant to step 1 of the process of FIG. 1.

Figure 2F:
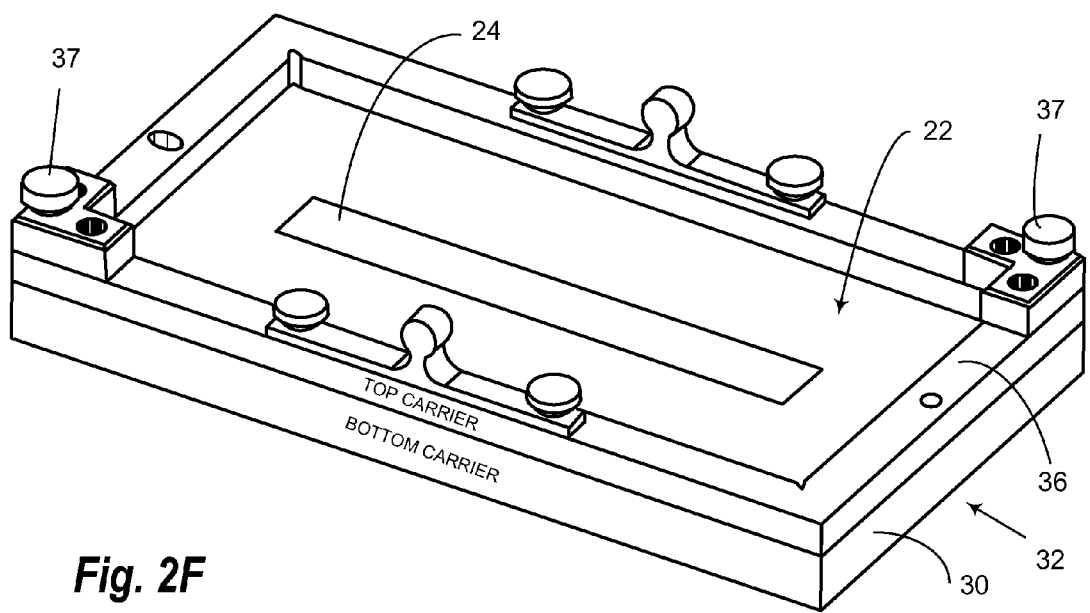
Figure 3B:
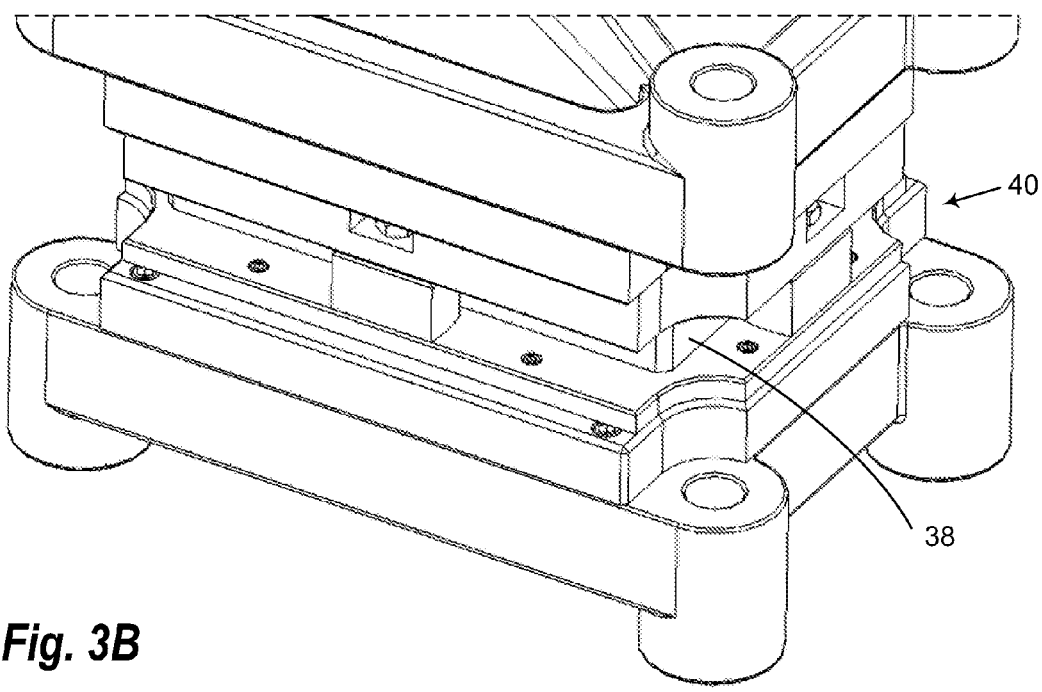
FIG. 3B shows the laminating press in a closed condition to secure the metallic ribbon to the upper surface of the film substrate by heat and pressure.
Figure 3C:
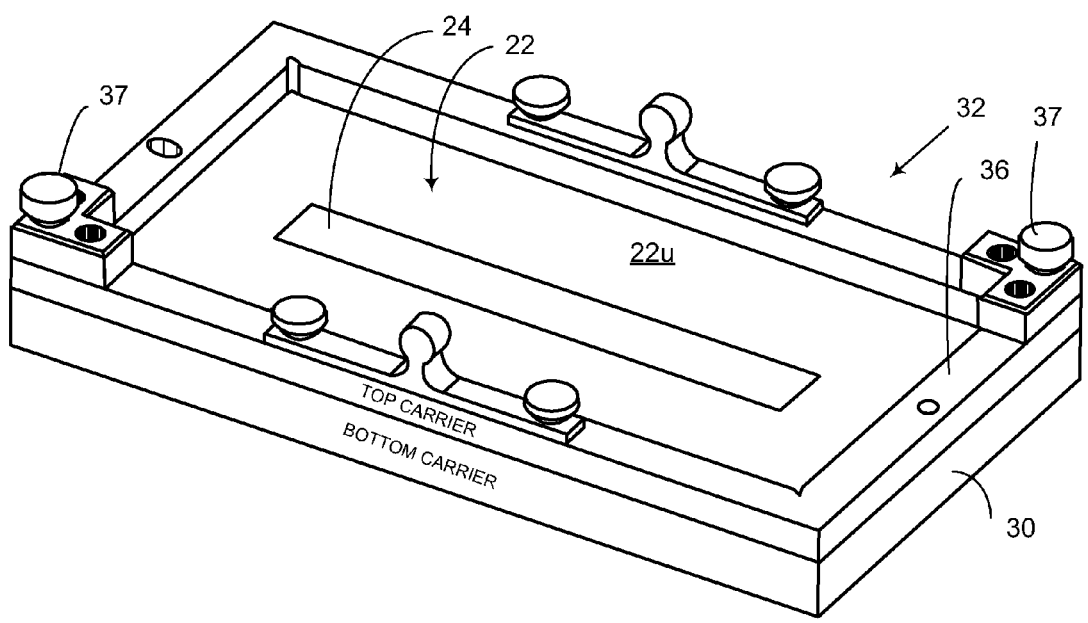

Thus secured, the film carrier 32 and film substrate supported metallic ribbon 24 are removed from the vacuum apparatus 26 as depicted in FIG. 2F and positioned on a bottom platen 38 of an open laminating press 40 as depicted in FIG. 3A. The laminating press 40 is then closed as depicted in FIG. 3B and heat and pressure are applied by the press to the film substrate 22 and metallic ribbon 24, bonding the metallic ribbon to the upper surface 22u of the film substrate. The press is then opened and the carrier 32 removed from the press as depicted in FIG. 3C, thereby completing attachment of the metallic ribbon 24 to the film substrate 22 pursuant to step 2 of the process of FIG. 1 and readying the metallic ribbon and its supporting film substrate for the machining of the first and second microcircuits pursuant to step 3 of the process of FIG. 1.

Such machining of the first and second multi-conductor microcircuits 12a and 12b from the metallic ribbon 24 is depicted in FIGS. 4A through 4I and includes laser machining of the metallic ribbon 24 so as to produce the structures of the head and tail portions of each of the microcircuits 12a and 12b as previously described with respect to FIGS. 4E through 4H and where the longitudinally extending laterally spaced conductors 18a and 18b in the tail portions 16a and 16b of the microcircuits 12a and 12b preferably are approximately 75 micron in width with 50 micron kerfs 18k between the conductors as depicted in FIG. 4I. In order to better control the shape of the microcircuits, very short pulse laser machining can be used to precisely form the desired geometry. As used herein, the term "very short pulse" means pulses less than a nanosecond, such as in the femtosecond to hundreds of picosecond range. These very short pulse lasers provide superior micromachining compared with longer pulse lasers. The very short pulse lasers ablate illuminated material without significant transfer of heat to surrounding material. This allows the very short lasers to machine fine details and leaves the unablated material in essentially its original state. For example, very short pulse laser machining may be performed using a picosecond laser, at UV, visible, or IR wavelengths.

More specifically as to the teachings of FIGS. 4A through 4I, FIG. 4A shows the film carrier 32 supporting the film substrate 22 and metallic ribbon 24 over a vacuum chuck 42 used to support film or plate-like materials for laser machining. As depicted, the vacuum chuck 42 includes a rectangular base 42b connected by a hose 42h to a vacuum source (not shown). The base 42b supports a pedestal 42p having openings (not shown) in a flat top surface 42ps for supporting the film substrate 22 and metallic ribbon 24 for laser machining of the metallic ribbon. FIG. 4B shows the carrier 32 on the flat top surface of the pedestal 42p (seen in FIG. 4A) of the vacuum chuck 42 where the film substrate 22 and metallic ribbon 24 are secured by vacuum forces generated by the vacuum chuck 42. FIG. 4C diagrammatically depicts the laser cutting of an outline of the microcircuits 12a and 12b in the metallic ribbon 24 supported by the pedestal while FIG. 4D shows the outline of the first and second microcircuits 12a and 12b formed within the ribbon 24. As represented, the microcircuits 12a and 12b include head portions 14a and 14b, respectively, each comprising a flat multi-conductor fan-shaped head portion with spaced exposed circuit attachment pads 15 and flat elongated multi-conductor tail portions 16a and 16b with longitudinally spaced laterally extending ring electrode receiving pads as previously described in detail with respect to FIGS. 4E-4H, the tail portions having a cross-section as depicted and previously described with respect to FIG. 4I for the tail portion 16a thereby completing the machining of the first and second multi-conductor microcircuits 12a and 12b from the metallic ribbon 24 all pursuant to step 3 of the process of FIG. 1, readying the microcircuits 12a and 12b for lamination between the first film substrate 22 and a second film substrate pursuant to step 4 of the process of FIG. 1.

Step 4 is depicted in FIGS. 5A-6D and begins with the use of the film substrate vacuum support apparatus 26 previously described with respect to FIGS. 2A-2D and step 1 of the process of FIG. 1. In FIG. 5A, the film vacuum support apparatus 26 is shown with an open rectangular top filler frame 44 above the open rectangular top channel 29 in the support apparatus. As shown, the filler frame 44 has front, back, and side support extensions 44a, 44b, 44c, and 44d for resting on a top of the apparatus 26 around the channel 29. Thus positioned, a top portion of the filler frame is exposed above upper surfaces of the extensions as shown in FIG. 5B to support a second film substrate 46 extending from a roll 47 over the apparatus 26 and shown in FIG. 5C. Preferably, the film substrate 46 is the same as the previously described film substrate 22, possessing the same physical and functional characteristics including a "peel-off" backing 46b resting on the filler frame 44 after it is seated in the channel 29 as depicted in FIG. 5D. Thus positioned, the vacuum support apparatus 26 is activated to secure the film substrate 46 to the top of the filler frame 44 and the film substrate extending beyond an outside of the frame is removed. The frame 44 and film substrate 46 are then removed from the apparatus 26 as shown in FIG. 5E and the film carrier 32 supporting the film substrate 22 inverted over the frame 44 and film substrate 46 as depicted in FIG. 5F. The carrier 32 and film substrate 22 are then lowered onto the frame 44 and the combination inverted as depicted in FIG. 5G showing the carrier 32 facing upward with the second film substrate 46 between the carrier and the frame 44. Thus positioned, the carrier and frame are ready for lamination of the second film substrate 46 to a top surface of the metallic ribbon 24 with the top surface of the film substrate 22 extending beyond the ribbon within the carrier.

Such lamination is performed in the previously described laminating press 40 which as shown in FIG. 6A receives and supports the carrier 32, frame 44, film substrates 22 and 46 and ribbon 24 on its lower platen (the substrates 22 and the ribbon 24 being covered by the film 46). When the press 40 is closed as depicted in FIG. 6B, heat and pressure are applied to laminate the film substrate 46 to the top surface of the film substrate 22 and to the ribbon 24 supported thereby. The press is then opened as shown in FIG. 6C and the carrier 32, frame 44 and film substrates 22 and 46 laminated to the ribbon 24 removed from the press as depicted in FIG. 6D to complete step 4 of the process of FIG. 1 and to ready the laminated microcircuits for excision from film substrates pursuant to step 5.

FIGS. 7A-7H depict the exposing of the electrode receiving pads and circuit attachment pads pursuant to step 4a of the process of FIG. 1, such as by using a laser to remove material by vaporization, i.e., ablation. The laser system used in this process may utilize a vision system that accurately aligns the laser with the microcircuits for the ablation and machining operations. Specifically, as depicted in FIG. 7A, the carrier 32, frame 44 and laminated film substrates 22 and 46 are inverted over the vacuum chuck 42 of FIGS. 4A-4D, and the backing 22b and lower surface of the film substrate 22 is laser ablated as represented in FIG. 7B to expose bottoms surfaces of the metal circuit attachment pads 15 of the head portions 14a and 14b and the bottom surface of the electrode receiving pad 20b-1 as depicted in FIG. 7C and to expose bottom surfaces of electrode receiving pads 20-a-1 through 20b-9 of the first and second microcircuits as depicted in FIG. 7D. As depicted in FIG. 7E, the carrier 32 and frame 44 are then returned to their original upright position and again placed on the vacuum chuck 42 for laser ablation of the backing 46b and film substrate 46 as represented in FIG. 7E. Such laser ablation exposes top surfaces of the metal circuit attachment pads 15 of the head portions 14a and 14b of the first and second microcircuits 12a and 12b as depicted in FIG. 7F and extends through the backing 46b and film substrates 46 and 22 and into the backing 22b along the outlines of the head portions 14a and 14b and the outlines of the tail portions 16a and 16b as depicted for the tail portion 16b of the second microcircuit 12b in FIGS. 7G and 7H. Specifically, as represented in FIGS. 7G and 7H, the microcircuit outline laser cutting passes completely through the upper backing 46b of the film substrate 46, the adhesive under the backing 46b, and over and under the flat conductors 18 and circuit attachment and electrodes receiving pads 15 and 20 within the head and tail portions of the first and second microcircuits 12a and 12b and through the film substrate 22 and into the backing 22b. Such laser cutting prepares the microcircuits for removal from the backing 22b of the film substrate 22 pursuant to FIGS. 8A-8C and removal of the backing 46b of the film substrate 46 pursuant to FIGS. 8D and 8E, leaving the excised microcircuits 12a and 12b as depicted in FIGS. 8F and 8G.

8A-8G depict the excising of the first and second microcircuits from the first and second film substrates pursuant to step 5 of the process of FIG. 1. More specifically, FIG. 8A is a top view of the carrier 32 with the backing 46b of the film substrate 46 covering all of the first and second microcircuits 12a and 12b formed in the metallic ribbon 24 on the upper surface of the film substrate 22 with the exception of the exposed tops of the circuit attachment pads 15 in the head portions 14a and 14b. FIG. 8B illustrates the excising of the laminated microcircuits 12a and 12b from the carrier 32, leaving the backing 22b of the film substrate 22 within the carrier. FIG. 8C is a top view of the excised first and second laminated microcircuits 12a and 12b illustrating the exposed tops of the circuit attachment pads 15 of the head portions 14a and 14b through the backing 46b of the film substrate 46. FIGS. 8D and 8E illustrate the removal of the exposed backing 46b of the film substrate 46 from the microcircuits 12a and 12b respectively. FIGS. 8F and 8G are enlarged top views of head and tail portions of microcircuits 12a and 12b after removal of the backing 46b of the film substrate 46. FIG. 8F illustrates the exposed circuit attachment pads 15 and the insulated upper surfaces of the remainders of the head portions of the microcircuits 12a and 12b. Circuit attachment pads 15 are used to electrically couple the electrodes to the cochlear implant circuitry. FIG. 8G illustrates the insulated upper surfaces of the electrode receiving pads and remainders of the tail portions of the microcircuits 12a and 12b. Only the metallic bottom surfaces of the electrode receiving pads 20a-1 through 20b-9 are exposed, as illustrated in FIG. 7D.

J-shaped Cochlear Electrode Array

As will be described in detail hereafter with respect to FIGS. 9A-11J, in the cochlear electrode array 10 comprising a first preferred embodiment of the present invention, the flat longitudinally extending tail portion 16a of the first microcircuit 12a is helically wrapped on a longitudinal axis 48 in a first direction (e.g. clockwise) with its flat electrode receiving pads 20a spaced longitudinally and extending around the insulation 19a covering the electrical conductors 18a of the first microcircuit 12a. Thus arranged, the electrode receiving pads 18a-1 through 18a-8 of the first microcircuit 12a define a first series 21a of longitudinally spaced exposed metallic electrode receiving pads. The electrode receiving pads of series 21a may wrap 360 degrees or more around the insulation 19a, forming a complete circle; alternatively, they may wrap only partially around the insulation 19a, forming a semicircle. The forwardmost pad 20a-8 of the first series 21a is adjacent a forward end of the helically wrapped tail portion 16a of the first microcircuit 12a with the remainder of the pads (20a-2 through 20a-8) comprising the first series 21a being longitudinally spaced rearward from the forwardmost pad 20a-8. The tail portion 16b of the second flat microcircuit 12b also is helically wrapped, but in a direction opposite to the first direction (e.g. counterclockwise), and is helically wrapped over the helically wrapped tail portion 16a of the first microcircuit 12a with its longitudinally spaced electrode receiving pads 20b extending around the insulation 19b covering the electrical conductors of the second microcircuit 12b. Thus arranged, the electrode receiving pads 20b-2 through 20b-9 of the second microcircuit 12b define a second series 21b of longitudinally spaced exposed metallic electrode receiving pads, a forwardmost pad 20b-9 of the second series 21b being located adjacent the rearmost electrode receiving pad 20a-1 of the first series 21a and a remainder of the electrode receiving pads of the second series (20b-2 through 20b-8) being spaced longitudinally rearward from the forwardmost pad 20b-9. The electrode receiving pads of series 21b may wrap 360 degrees or more around the insulation 19b, forming a complete circle; alternatively, they may wrap only partially around the insulation 19b, forming a semicircle. Also, a rearmost electrode receiving pad 20b-1 of second flat microcircuit 16b is longitudinally separated rearward from the second series 21b of pads 20b to define a reference or ground electrode receiving pad for the cochlear electrode array. Finally, the cochlear electrode array 10 comprises ring electrodes 23 located on and electrically connected to each of the longitudinally spaced electrode receiving pads 20a and 20b of the tail portions 16a and 16b of the first and second microcircuits 12a and 12b. Further, a forwardmost end portion 10e of the helically wrapped tail portions of the cochlear electrode array 10 is shaped in a "J" configuration and the entire helically wrapped tail portions 16a and 16b of the first and second microcircuits are overmolded with a suitable polymeric material 19c as depicted in FIGS. 11H-11J. As depicted most clearly in FIG. 11J, an insertion pad 10a is overmolded onto the electrode array at a junction of the "J" and the rearward balance of the array. The insertion pad 10a functions as an instrument or finger force applying pad for a surgeon during insertion of the array 10 into the cochlea of a patient.

In the cochlear electrode array 11, comprising a second preferred embodiment of the cochlear electrode array of the present invention depicted in FIGS. 19B and 20C, a forward-most end 11e of the helically wrapped tail portions 16a and 16b of the cochlear electrode array 11 including the first and second series 21a and 21b of electrode receiving pads 20a-1 through 20a-8 and 20b-2 through 20b-9 is helically wrapped on a second longitudinal axis 50. The axis 50 is laterally offset from the previously described longitudinal axis 48 of a rearward portion 11r of the helically wrapped tail portions of the cochlear array. Such wrapping of the forwardmost end 11e of the tail portions 16a and 16b results in a stylet receiving lumen 51 in the forwardmost end of the cochlear electrode array 11 that is shaped as an inward spiral that may be separately overmolded with a suitable polymeric material 19c to complete the spiral-style cochlear electrode array 11 as depicted in FIG. 20C.

The process for helically wrapping the tail portions of the first and second laminated microcircuits 16a and 16b, mounting and electrically connecting ring electrodes 23 on and to exposed electrode receiving pads 20a and 20b of the helically wrapped tail portions 16a and 16b and the overmolding thereof pursuant to steps 6, 7, and 8 of the process of FIG. 1 for the cochlear electrode array 10 is depicted in FIGS. 9A-11J. Similarly, the process for helically wrapping the tail portions of the first and second laminated microcircuits 16a and 16b, mounting and electrically connecting ring electrodes 23 on and to exposed electrode receiving pads 20a and 20b of the helically wrapped tail portions 16a and 16b, and the overmolding thereof pursuant to steps 6, 7, and 8 of the process of FIG. 1 for the cochlear electrode array 11 is depicted in FIGS. 12A-20C.

Specifically as to the cochlear electrode array 10 and as depicted in FIG. 9A, the fan-shaped head portion 14b of the second microcircuit 12b is placed on an upper flat portion 52u of a support base 52 for a tooling bow 54. Thus positioned, the tail portion 16b of the second microcircuit 12b extends forward from the head portion 14b with its flat reference electrode receiving pad 20b-1 extending forward at an acute angle of about 73 degrees from a forward end of the flat conductor 18b-1 formed in the tail portion 16b, as previously illustrated in and described with respect to FIG. 4E. As also shown in FIG. 9A, vertical pins 56a and 56b extend upward from the upper flat portion 52u of the support base 52 through corresponding holes in the head portion 14b to hold the head portion 14b flat on the support base. Likewise, as shown in FIG. 9B, the fan-shaped head portion 14a of the first microcircuit 12a is positioned on the upper flat portion 52u of the support base 52 to complement the head portion 14b and form a nearly complete fan 14. As also shown in FIG. 9B, vertical pins 56c and 56d extend upward from the upper flat portion 52u of the support base 52 through corresponding holes in the head portion 14a to hold the head portion 14a flat on the support base with the tail portion 16a extending from the head portion 14a over and at an angle away from the tail portion 16b. Vertical pin 56e extends upward from a lower flat portion 52l of the support base 52.

As depicted in FIG. 9C, the tooling bow 54 is placed on the lower flat portion 52l of the support base 52, and a first end 54a of the tooling bow secured to the support base by the vertical pin 56e extending through a corresponding hole in the first end of the tooling bow and a screw 54s having an upper knob 54k and a lower threaded portion (not shown) extending into a corresponding threaded hole in the lower flat portion of the support base. As thus constructed, a turning of the knob 54k in a first direction will firmly attach the tooling bow 54 to the support base 52 while a turning of the knob in an opposite direction will release the tooling bow from the support base. With the tooling bow 54 secured to the support base 52 as shown in FIG. 9C, a wire 58 is inserted through a horizontal hole 56h-1 extending horizontally through the end 54a of the tooling bow 54 as secured to the support base 52 and over the head portions 14a and 14b secured to the support base and between and over the tail portions 16a and 16b of the first and second microcircuits 12a and 12b.

As depicted in FIG. 9D, the forward end of the wire 58 is passed through a series of ring electrodes 23 into and secured within a hole 56h-2 in an opposite or second end 54b of the tooling bow 54 and axially tensioned. As illustrated in FIG. 9D, a rearmost ring electrode 23-1 is slightly larger in outer diameter and length than an immediately adjacent group of the ring electrodes comprising electrodes 23-2 through 23-9, while the ring electrodes 23-2 through 23-9 are slightly larger in outer and inner diameter than an immediately adjacent forward-most group of ring electrodes comprising ring electrodes 23-10 through 23-17.

As will be explained hereinafter, such size differences are to accommodate differences in the size of the exposed metallic ring electrode receiving pads 20 formed during the helical wrappings of the tail portions 16a and 16b of the first and second microcircuits 12a and 12b.

As depicted in FIG. 9E, beginning with the head portions 14a and 14b of the microcircuits 12a and 12b positioned on the support base 52 and the tail portions 16a and 16b of the microcircuits extending longitudinally away from the head portions and under the tensioned wire 58, the tail portion 16a of the first microcircuit 12a extending from the head portion 14a is helically wrapped in a first forward direction (e.g. clockwise) along a longitudinal axis 48 formed by the tensioned wire 58 as shown in FIG. 9F. The tail portion 16a is wrapped at an angle β such as about 22° so that the microcircuit lies flat. During such helical wrapping, the insulating material 19a from the film substrate 46 covering top portions of the conductors 18a engages the tensioned wire 58, and the insulation material 19a from the film substrate 22 covering bottom portions of the conductors is exposed. Such helical wrapping of the tail portion 16a is continued to the ring electrode receiving pad 20a-1 which, due to its forward acute angle to the longitudinal axis of the conductor 18a-1, encircles the insulation 19a with its exposed metallic bottom surface forming the exposed metallic ring electrode receiving pad 20a-1 of the cochlear electrode array 10. This is followed by a like formation of the longitudinally spaced exposed metallic ring electrode receiving pads 20a-2 through 20a-8 to form a first series 21a of longitudinally spaced exposed metallic ring electrode receiving pads, pad 20a-8 being the forward-most ring electrode receiving pad 20a-8 of the series 21a as depicted in FIG. 9G.

The above-described formation of the ring electrode receiving pads and the first series 21a of longitudinally spaced exposed metallic ring electrode receiving pads is followed by a helical wrapping of the tail portion 16b of microcircuit 12b on the axis 48 and forward over the previously wrapped tail portion 16a as depicted in FIGS. 9H-9J. As illustrated in FIGS. 9H and J, the helical wrapping of the tail portion 16b is in a second forward or opposite direction relative to the first forward direction associated with the helical wrapping of the tail portion 16a (e.g. counterclockwise). Such forward helical wrapping of the tail portion 16b begins adjacent the head portion 14b forward along and around the longitudinal axis 48 and over the previously helically wrapped tail portion 16a to neutralize any undesired lateral stresses in the microcircuit 12a that may have been created during the forward clockwise helical wrapping of the first microcircuit 12a. The tail portion 16b is wrapped at an angle γ such as about 22° so that the microcircuit lies flat. During the helical wrapping of the tail portion 16b, the insulation 19b covering the upper surfaces of the conductors 18b contacts the insulation 19a covering the helically wrapped tail portion 16a and the insulation 19b covering the bottom surfaces of the conductors 18b is exposed as is the exposed metallic bottom surfaces of the ring electrode receiving pads 20b-1 through 20b-9 as shown in FIGS. 9I and 9J. In particular, it is by virtue of the forward acute angle of the pads 20b-1 through 20b-9 relative to the longitudinal axes of conductors 18b from which they extend that the forward counterclockwise helical wrapping of the tail portion 16b results in the exposed metallic bottom surfaces of the pads 20b encircling the insulation covering of the helically wrapped tail portion 16a to form the exposed metallic ring electrode receiving pad 20b-1 extending from and electrically connected to the forward end of the conductor 18b-1 as well as a second series 21b of longitudinally spaced exposed metallic ring electrode receiving pads 20b-2 through 20b-9 extending from forward ends of and electrically connected to the conductors 18b-2 through 18b-9 respectively. As previously noted, the conductor 18b-1 is much shorter than its adjacent conductors 18b-2 through 18b-9. Therefore, the ring electrode receiving pad 20b-1 is spaced considerably rearward of the second series 21b of ring electrode receiving pads 20b-2 through 20b-9 as depicted in FIG. 9I, the pad 20b-9 being immediately rearward of the ring electrode receiving pad 20a-1 of the first series 21a of ring electrode receiving pads as depicted in FIG. 9J. Thus, step 6 of the process of FIG. 1 for the first preferred cochlear electrode array 10 is completed, readying the helically wrapped microcircuits 12a and 12b for the mounting and electrical connection of the ring electrodes 23-1 through 23-17 on and to the ring electrode receiving pads 20b-1 through 20b-9 pursuant to step 7 of the process of FIG. 1.

With respect to the mounting and electrical connection of the ring electrodes 23-1 through 23-7 on and to the ring electrode receiving pads 20b-1 through 20b-9 and as diagrammatically depicted in FIGS. 10A through 10C, each of the ring electrodes 23-1 through 23-17 supported on the tensioned wire 58 of the tooling bow 54 is moved rearward and mounted over and on a corresponding one of the exposed metallic ring electrode receiving pads 20a and 20b pursuant to step 7 of the process of FIG. 1. In that regard, it should be noted that each ring electrode fits securely on its associated ring electrode receiving pad due to the inner diameters and widths of the ring electrodes being nearly equal to or only slightly larger than the outer diameter and widths of the ring electrode receiving pad upon which it is positioned. In this regard, FIG. 10A depicts the ring electrode 23-1, comprising a reference or ground ring electrode for the cochlear electrode array 10, on and around the exposed metallic ring electrode receiving pad 20b-1, comprising the reference ring electrode receiving pad for the cochlear electrode array 10. Similarly, ring electrodes 23-2 through 23-17 are depicted on and around corresponding ones of the exposed metallic ring electrode receiving pads in the first and second series 21a and 21b. As depicted in FIGS. 10A to 10C, with the ring electrodes thus mounted, each, in turn, is welded to its supporting ring electrode receiving pad, such as by resistance, ultrasonic, or laser welding, as illustrated with laser beam 25. In this regard FIG. 10B is an enlarged showing of the welding of the ring electrode 23-1 on and to the ring electrode receiving pad 20b-1, while FIG. 10O depicts the successive welding of the ring electrodes 23-2 through 23-17 to corresponding ones of the first and second series of exposed metallic ring electrode receiving pads 21a and 21b, thereby completing step 7 of the process of FIG. 1 for the cochlear electrode array 10 and readying the array for overmolding pursuant to step 8 of the FIG. 1 process.

As shown in FIG. 11A, with respect to the overmolding of the cochlear electrode array 10, the tooling bow 54 shown in FIGS. 10A-10O is positioned over a first lower support plate 60p-1 of a conventional overmolding apparatus 60, such as liquid injection molding (LIM) apparatus. As there depicted, a portion 16p of helically wrapped tail portions 16a and 16b between the head portion 14 and the ring electrode 23-2 is positioned in a longitudinally extending open channel 60c in a top surface of a first lower support plate 60p-1. A top cover 60tc of the overmolding apparatus 60 is placed over the portion 16p as depicted in FIG. 11B and the portion 16p is overmolded with a polymeric material 16s such as silicone. FIG. 11C depicts the tooling bow 54 and overmolded portion 16p removed from the overmolding apparatus 60 with the tensioned wire 58 and support base 52 being removed from the tooling bow 54, allowing the microcircuits 12a and 12b to be removed from the tooling bow as shown in FIG. 11D. An end portion 10e of the of the cochlear electrode array 10 of FIG. 11D forward of the overmolded portion 16p is then shaped/pre-formed in the shape of a "J" as shown in FIG. 11E and placed in a J-shaped top channel 60j of a second lower support plate 60p-2 of the overmolding apparatus 60 as shown in FIG. 11F. As shown in FIG. 11G, the J-shaped end portion 10e is covered with the top cover 60tc and overmolded with the polymeric material 16s, the top cover 60tc including bottom features (not shown) that block the placing of polymer over the longitudinally spaced ring electrodes 23 of the J-shaped end portion 10e, pursuant to step 8. As shown in FIG. 11H, the top cover 60tc is then removed and the overmolded J-style cochlear electrode array 10 comprising the first preferred embodiment of the present invention is removed from the overmolding apparatus 60 as depicted in FIG. 11H, FIG. 11I being a slightly enlarged view of the J-style cochlear electrode array 10 of FIG. 11H showing the longitudinally spaced exposed ring electrodes 23-1 and 23-2 through 23-17 of the J-style cochlear electrode array 10 of the present invention and a small polymeric electrode array insertion pad 10a at a junction of the longitudinally extending helically wrapped portion 16p of the tail portions 16a and 16b and the J-shaped portion 10e of the electrode array 10. The pad 10a is formed by polymer flowing to a corresponding junction of the J-shaped channel 60J and a side channel 60s in the lower support plate 60p-2 of the overmolding apparatus 60 as depicted in FIGS. 11F and 11H and is utilized by a surgeon as an instrument or finger pressure point during the insertion of the electrode array into the cochlea of a patient. Finally, FIG. 11J is an enlarged view of the overmolded forward end 10e of the J-style cochlear electrode array 10 comprising a first preferred embodiment of the present invention formed pursuant to step 8 of the process of FIG. 1.

In the processes for forming both the first and second preferred embodiments 10 and 11 of the cochlear electrode array of the present invention (i.e. the J-style cochlear electrode array and spiral-style cochlear electrode array), the rearmost electrode receiving pad 20b-1 of the second microcircuit 12b and the ring electrode 23-1 positioned on and electrically connected thereto are spaced rearward of the second series 21b of electrode receiving pads 20b to define a reference or ground electrode for the associated cochlear electrode array. The manufacturing process described relative to FIGS. 9A-11J produces a J-style cochlear electrode array.

Spiral-shaped Cochlear Electrode Array

In the formation of the spiral-style cochlear electrode array 11, a slightly modified process depicted in FIGS. 12A-20D is employed, including the formation of a laterally spaced stylet lumen 51 in a helically wrapped forward end portion 11e of the cochlear electrode array 11. Basically, that process comprises two separate forward helical wrappings of the tail portions 16a and 16b of the first and second flat microcircuits 12a and 12b. The first separate helical wrapping comprises an initial helical wrapping of a portion 16a-1 of the tail portion 16a of the first microcircuit 12a adjacent its associated head portion 14a. That initial helical wrapping is in the first direction (e.g. clockwise) on and around the first longitudinal axis 48 and is immediately followed by an initial helical wrapping of a portion 16b-1 of the tail portion 16b of the second microcircuit 12b adjacent its head portion 14b in an opposite direction (e.g. counterclockwise) on and around the axis 48 and the initially wrapped tail portion 16a-1 of the first microcircuit 12a. Such forward initial wrappings of the initial tail portions 16a-1 and 16b-1 of the first and second microcircuits 12a and 12b continues to a location forward of the helically wrapped reference electrode receiving pad 20b-1 and rearward of the second series 21b of electrode receiving pads of the tail portion 16b of the second microcircuit 12b. Once such initial wrappings of the tail portions 16a-1 and 16b-1 of the first and second microcircuits 12a and 12b have been completed, the reference ring electrode 23-1 is mounted on and electrically connected to the exposed metallic outer surface of the reference electrode receiving pad 20b-1. Then, the initially wrapped tail portions 16a-1 and 16b-1 of the first and second microcircuits 12a and 12b are overmolded with a suitable polymeric material 16s followed by a second separate forward helical wrapping of remaining portions, or remainders, 16a-2 and 16b-2 of the tail portions 16a and 16b comprising (i) a forward helical wrapping of the remainder 16a-2 of the tail portion 16a of the first microcircuit 12a in the first or clockwise direction on and along a second longitudinal axis 50 parallel to and laterally spaced and offset from the first longitudinal axis 48 with the laterally extending electrode receiving pads 20a-1 through 20a-8 thereof extending around the insulating cover thereof to form the first series 21a of longitudinally spaced exposed metallic ring electrode receiving pads and (ii) a helical wrapping of the remainder 16b-2 of the tail portion 16b of the second microcircuit 12b in the second or counterclockwise direction on the axis 50 and around the helically wrapped remainder 16a-2 of the tail portion 16a of the first microcircuit 12a with the laterally extending electrode receiving pads 20b-2 through 20b-9 thereof extending around the insulating cover thereof to form the second series 21b of longitudinally spaced exposed metallic ring electrode receiving pads. By laterally offsetting the helical wrapping of the remainders 16a-2 and 16b-2 of the tail portions 16a and 16b from the initial wrapping of the initial portions 16a-1 and 16b-1 of the tail portions 16a and 16b, a longitudinally extending internal stylet lumen 51 is formed within the helically wrapped remainders 16a-2 and 16b-2, which, with the helically wrapped remainders, is shaped in the form of an inward spiral and overmolded with the polymeric material 16s to complete the second preferred embodiment, or spiral-style cochlear electrode array 11, of the present invention.

Figure 14D:
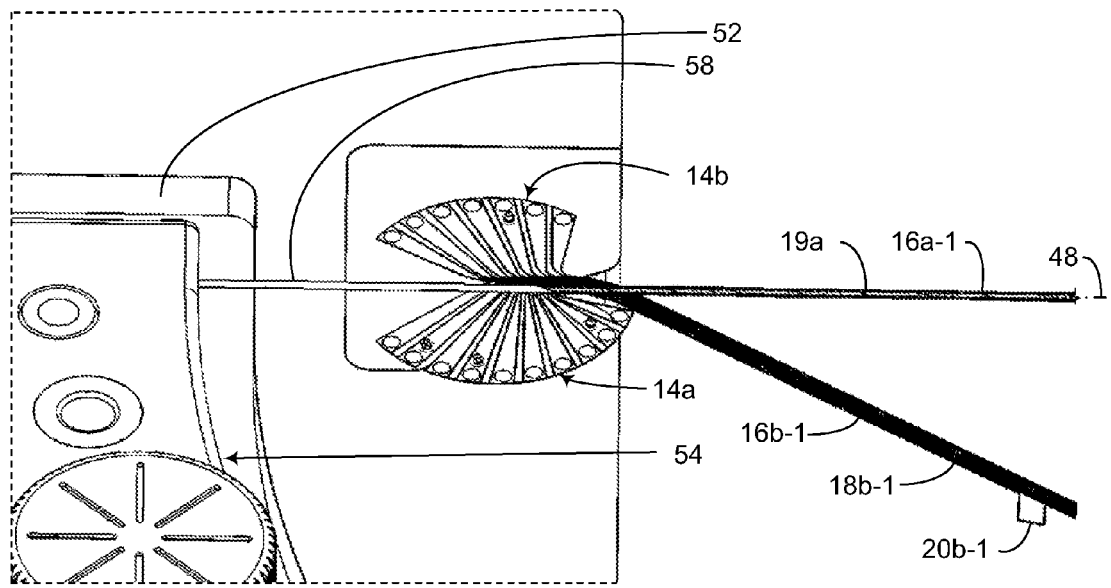
Figure 14E:
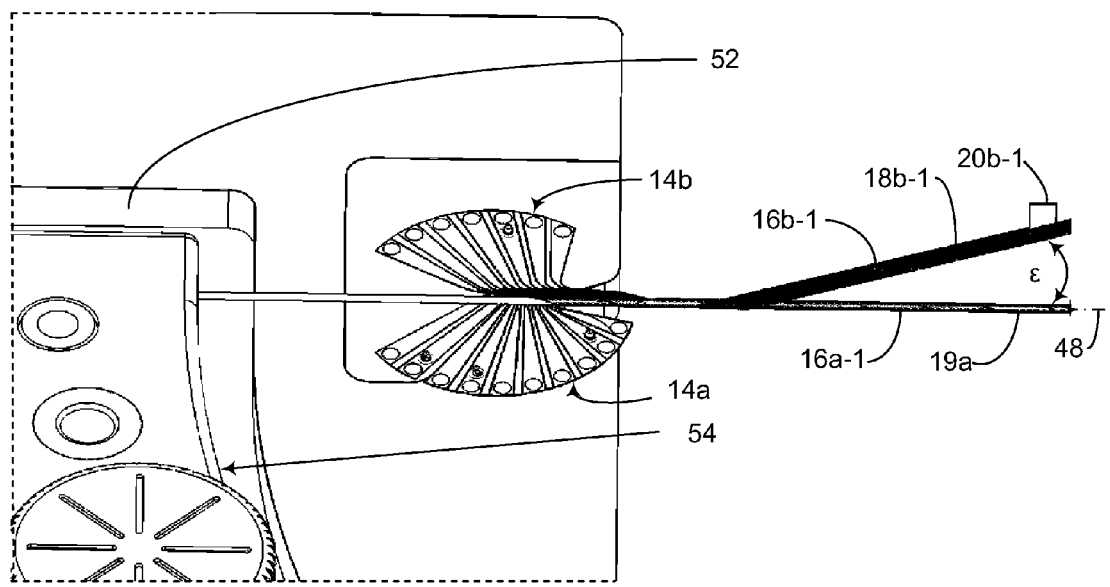
Figure 14F:
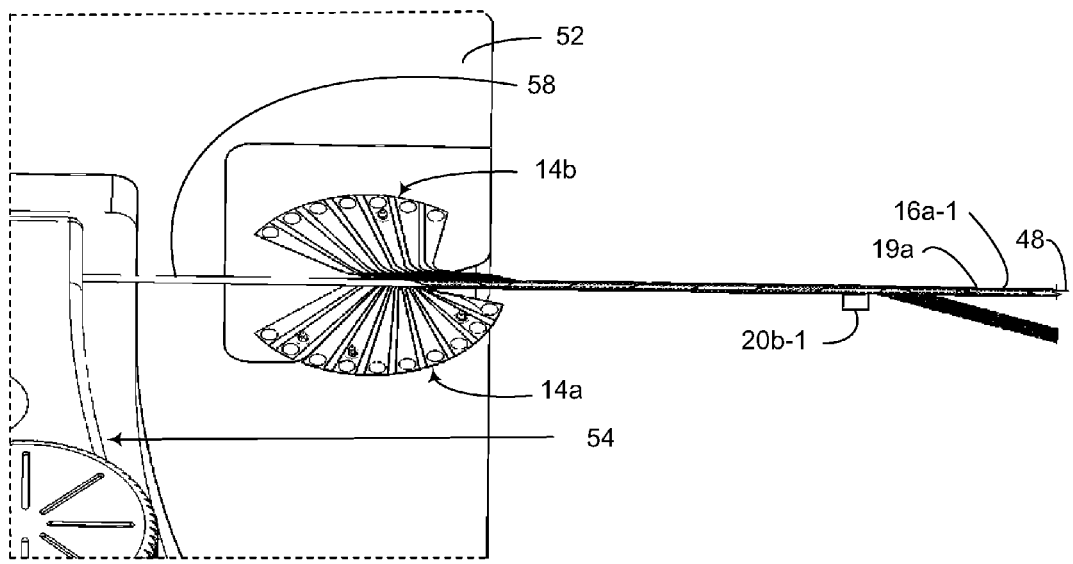
Figure 14G:
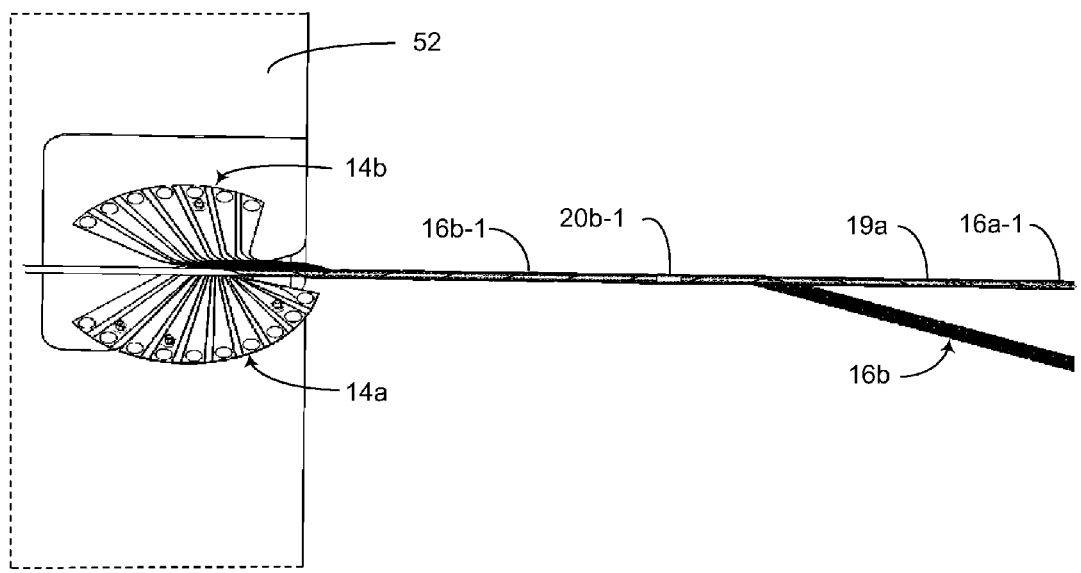

More specifically, as illustrated in FIG. 12A, the fan-shaped head portion 14b of the second microcircuit 12b is positioned above the base support 52 for the tooling bow 54 and lowered onto the base support as illustrated in FIG. 12B where it is secured by vertical pins 56a and 56b extending upward from the base support through corresponding holes in the head portion. Similarly, as illustrated in FIG. 13B, the fan-shaped head portion 14a of the first microcircuit 12a is positioned above the base support 52 of the tooling bow 54 and lowered onto the base support where it is secured by vertical pins 56c and 56d extending upward from the base support through corresponding holes in the head portion. As further illustrated, with the head portions 14a and 14b secured to the base support 52, the tail portion 16a extends longitudinally over and forward at an angle away from the tail portion 16b as more fully shown in FIG. 13C. Then, as illustrated in FIG. 14A, the tooling bow 54 is secured to the base support 52 in the manner previously described with respect to FIG. 9C-9D, with the tensioned wire 58 of the tooling bow extending on the first longitudinal axis 48 over the fan-shaped head portions 14a and 14b secured to the base support 52 and over and between the tail portions 16a and 16b as they extend longitudinally forward from their associated head portions. The wire 58 is tensioned after threading through the bow and contact rings are loaded, and is used as a winding mandrel. From the positions illustrated in FIG. 14A, and as illustrated in FIGS. 14B through 14G, the tail portions 16a and 16b are ready for the previously described initial forward helical wrapping of initial tail portions 16a-1 and 16b-1 to a location rearward of the second series 21b of ring electrode receiving pads as shown in FIGS. 17A and 17B. Specifically, FIGS. 14B-14D depict the initial wrapping of the initial tail portion 16a-1 in a forward clockwise direction on the tensioned wire 58 defining the first longitudinal axis 48, while FIGS. 14D-14F depict the initial wrapping of the initial tail portion 16b-1 in a forward counterclockwise direction on the axis 48 and over and along the helically wrapped tail portion 16a-1. As shown in FIG. 14C, the tail portion 16a is wrapped at angle δ such as about 22° so that the microcircuit lies flat. As shown in FIG. 14E, the tail portion 16b is wrapped at angle ε such as about 22° so that the microcircuit lies flat.

During the above described initial wrapping process, the flat ring electrode receiving pad 20b-1 of tail portion 16b-1 extends laterally and forward at an acute angle of about 73 degrees from the end of its associated conductor 18b-1. Thus constructed, during the forward helical wrapping of the initial tail portion 16b-1, the ring electrode receiving pad 20b-1 encircles or partially encircles the insulation 19a covering the outer surface of helically wrapped tail portion 16a with its metallic bottom surface forming the exposed metallic ring electrode receiving pad 20b-1 depicted in FIG. 14G. The electrode receiving pad 20b-1 may wrap 360 degrees or more around the insulation 19a, forming a complete circle; alternatively, pad 20b-1 may wrap only partially around the insulation 19a, forming a semicircle. As previously described, the pad 20b-1 provides support for a reference electrode of the cochlear electrode array 11.

FIGS. 15A-15C illustrate the mounting and electrical connection of the reference electrode on and to the pad 20b-1. As depicted in FIG. 15A, the ring electrode 23-1 for the cochlear electrode array 11 includes a longitudinally extending upper opening, or split, 23-1s dimensioned to allow the ring electrode fit over and onto the pad 20b-1 as shown in FIG. 15B where the split is closed and the electrode 23-1 electrically connected to the pad 20b-1 as by laser welding, as illustrated with laser beam 25. FIG. 15C is an enlarged view of the closed electrode 23-1 forming the reference electrode for the electrode array 11.

As depicted in FIGS. 16A and 16B, following the mounting and electrical connection of the of the reference electrode 23-1 to the ring electrode receiving pad 20b-1, the helically wrapped tail portions 16a-1 and 16b-1 supported on the tensioned wire 58 of the tooling bow 54 are overmolded with a suitable polymeric material using the previously described overmolding apparatus 60. As shown in FIG. 16A, the tooling bow 54 is inverted and the tensioned wire 58 placed in the longitudinally extending main channel 60c in the support plate 60-1p with the head portions 14a and 14b covered by the support base 52 and the electrode receiving pads 20a and 20b of the first and second series 21a and 21b extending outside the overmolding apparatus 60. The top cover 60tc of the overmolding apparatus 60 is then placed on the support base 60-1p, and the apparatus 60 is operated to overmold the helically initially wrapped tail portions 16a-1 and 16b-1 within the channel 60c with a polymeric material 16s with the exception of the reference ring electrode 23-1 that is protected by features (not shown) extending from a lower surface of the top cover 60tc. The tooling bow 54 is then removed from the overmolding apparatus 60 and returned to its upright condition as depicted in FIG. 17A and the overmolded helically wrapped initial tail portions of the microcircuits 12a and 12b removed from the tooling bow as shown in FIG. 17B for further processing of the remainders 16a-2 and 16b-2 of the microcircuits as depicted in FIGS. 17C-18B.

In that regard, FIG. 17C shows the overmolded helically wrapped initial tail portions of the first and second microcircuits 12a and 12b of FIG. 17B over a second, L-shaped support base 52-2 for the tooling bow 54. The support base 52-2 includes an open longitudinally extending top channel 53 into which the overmolded helically wrapped initial portions 16a-1 and 16b-1 of the microcircuits are placed as shown in FIG. 17D, the head portion 14 of the microcircuits being secured to the base support 52-2 by vertical pins 56a-56d as previously described and the first and second series 21a and 21b of electrode receiving pads of the remainders 16a-2 and 16b-2 of the microcircuits 12a and 12b extending forward beyond the channel 53 as shown in FIG. 17E.

As shown in FIG. 17F, ring electrodes 23 are preloaded onto a wire 58, which is then tensioned in the tooling bow 54. The tooling bow 54 with its tensioned wire 58 supporting ring electrodes 23 is then located above the second support base 52-2 and, as shown in FIG. 17G, lowered to a position where the tensioned wire 58 is just above, parallel to, and offset slightly from the overmolded helically wrapped initial portions 16a-1 and 16b-1 of the first and second microcircuits within the top channel 53 of the second base support 52-2.

As shown in FIG. 17H, the tooling bow 54 is then secured to the support base 52-2 in the same manner previously described relative to the base support 52 but with the tensioned wire 58 laterally offset from and extending longitudinally along a second axis 50 above and parallel to the channel 53 and the overmolded initial tail portions 16a-1 and 16b-1 that were helically wrapped on the axis 48. The parallel lateral off-set relationship of the tensioned wire 58 and its longitudinal axis 50 relative to the longitudinal axis 48 upon which the initial tail portions 16a-1 and 16b-1 were helically wrapped is also illustrated in FIGS. 17H and 17I. Specifically, FIGS. 17H and 17I show the tensioned wire 58 of the tooling bow 54 passing forward between the remainders 16a-2 and 16b-2 of the tail portions 16a and 16b and offset along the second longitudinal axis 50 above and parallel to the top channel 53 from which the remainders extend, the remainders being ready for separate forward helical wrapping as depicted in FIGS. 17J-17Q. FIGS. 17J-17N show the remainder 16a-2 of the tail portion 16a being helically wrapped in a forward clockwise direction on the tensioned wire 58 and its axis 50 ending with the ring electrode receiving pad 20a-8 immediately adjacent the series of ring electrodes 23 carried by the tensioned wire 58 adjacent the end 54b of the tooling bow 54. Likewise, FIGS. 17M-17Q show the remainder 16b-2 of the tail portion 16b being helically wrapped in a forward counterclockwise direction on the tensioned wire 58 and its axis 50 ending with the ring electrode receiving pad 20b-9 immediately adjacent the ring electrode receiving pad 20a-1 of the first series 21a of longitudinally spaced ring electrode receiving pads comprising pads 20a-1 through 20a-8. Specifically, FIG. 17J depicts the first forward clockwise wrap of the remainder 16a-2 on the axis 50 of the tensioned wire 58 forward of its position shown in FIG. 17I, while FIGS. 17K, 17L, and 17M depict second, third, and fourth forward clockwise wraps, respectively, of the remainder 16a-2 on the axis 50. As shown most clearly in FIGS. 17L and 17M, due to the acute angle relationship between the ring electrode receiving pads 20a-1 through 20a-8 and the longitudinal axes of the conductors 18a-1 through 18a-8 from which they respectively extend, such forward clockwise helical wrapping of the remainder 16a-2 results in the insulated upper surfaces of the pads 20a-1 through 20a-8 wrapping over the insulation of the remainder 16a-2 between the pads while the exposed metallic bottom surfaces of the pads 20a-1 through 20a-8 encircle their upper insulation. The electrode receiving pads 20a-1 through 20a-8 may wrap 360 degrees or more, forming a complete circle; alternatively, the receiving pads may wrap only partially, forming a semicircle. Such helical wrapping forms the series 21a of longitudinally spaced exposed metallic ring electrode receiving pads shown in FIG. 17N with the pad 20a-8 being immediately adjacent the series of ring electrodes 23 carried by the tensioned wire 58. Similarly, FIG. 17I depicts the first forward counterclockwise wrap of the remainder 16b-2 on the axis 50 of the tensioned wire 58 and over the helically wrapped remainder 16a-2 forward of its position shown in FIG. 17I. Further, FIG. 17P depicts the remainder 16b-2 after a number of forward counterclockwise turns on the axis 50 sufficient to encircle the helically wrapped remainder 16a-2 with the ring electrode receiving pads 20b-2 through 20b-6, pads 20b-7 and 20b-8 being in the process of encircling the remainder 16a-2 while pad 20b-9 is hidden from view. Again, due to the acute angle relationship between the ring electrode receiving pads 20b-2 through 20b-9 and the longitudinal axes of the conductors 18b-2 through 18b-9 from which they respectively extend, such forward counterclockwise helical wrapping of the remainder 16b-2 results in the insulated upper surfaces of the pads 20b-2 through 20b-9 wrapping over the insulation of the remainder 16a-2 while the exposed metallic bottom surfaces of the pads encircle their upper insulation. The electrode receiving pads 20b-2 through 20b-9 may wrap 360 degrees or more, forming a complete circle around the insulation; alternatively, the receiving pads may wrap only partially, forming a semicircle. Such helical wrapping forms the series 21b of longitudinally spaced exposed metallic ring electrode receiving pads shown in FIG. 17Q with the pad 20b-9 being immediately adjacent the pad 20a-1 of the series 21a. Thus, step 6 of the process of FIG. 1 is complete and the first and second series 21a and 21b of exposed metallic ring electrode receiving pads are ready for the mounting and electrical connection of the ring electrodes 23 pursuant to step 7 of the process of FIG. 1.

With regard to step 7 of the process of FIG. 1, FIG. 17R depicts the ring electrodes 23-2 though 23-17 carried by the tensioned wire 58 moved rearward on the tensioned wire 58 of the tooling bow 54 and placed upon the exposed metallic ring electrode receiving pads 20b-2 through 20a-8 respectively. Then, the ring electrodes are individually secured and electrically connected to their respective metallic ring electrode receiving pads as by the laser welding depicted in FIGS. 18A and 18B, as illustrated with laser beam 25. Thus, step 7 of the process of FIG. 1 is complete and the helically wrapped remainders 16a-2 and 16b-2 of the tail portions 16a and 16b are ready for overmolding pursuant to step 8 of the process of FIG. 1.

As to step 8, FIGS. 19A-19D illustrate the pre-forming of a forward end portion 11e of the cochlear electrode array 11 into a spiral shape ready for overmolding and the completion of the spiral-style cochlear electrode array comprising a second preferred embodiment of the present invention. First, as depicted in FIG. 19A, the helically wrapped remainders 16a-2 and 16b-2 are removed from the tooling bow 54 as by disconnecting the tensioned wire 58 from the end 54b of the tooling bow and the drawing of the tensioned wire from the helically wrapped remainders leaving the electrode array as shown in FIG. 19A. Then, as shown in FIG. 19B, a rod 70, comprising, for example, a plastic such as Teflon® polytetrafluoroethylene (PTFE), is inserted into the rear open end of the stylet lumen 51 and moved forward to the position shown. Next, the end portion 11e is progressively shaped, e.g., by hand, into the form of an inward spiral as depicted in FIGS. 19C and 19D.

As shown in FIG. 20A, the electrode array is transferred to the previously described overmolding apparatus 60 and positioned in an open channel 60c having a spiral-shaped end portion in a third bottom support plate 60p-3 for the overmolding apparatus 60. The spiral-shaped end portion of the electrode array is located in the spiral-shaped portion of the channel 60c with the head portion 14 and adjacent tail portion exposed outside the apparatus. The cover 60tc is then placed over the bottom plate and the overmolding apparatus 60 operated to overmold the remainders 16a-2 and 16b-2 and the spiral-shaped end portion 11e with a suitable polymeric material such as silicone. The overmolding apparatus 60 is then opened and the overmolded electrode array 11 lifted from the apparatus, as depicted in FIG. 20C. Finally, as shown in the enlarged view of the end portion 11e of the cochlear electrode 11 illustrated in FIG. 20D, the plastic rod 70 is removed from the lumen 51, thereby completing the process of FIG. 1 for a second preferred version of the present invention.

While preferred embodiments of the microcircuit cochlear electrode array including first and second microcircuits and processes for their manufacture have been illustrated and described in detail above, it is appreciated that changes and modifications may be made in the illustrated embodiments without departing from the spirit of the invention. For example, if it is desired to increase the number of longitudinally spaced ring electrode sites beyond those in the illustrated cochlear electrode array including two microcircuits, additional microcircuits may be laser machined in the manner already described and added to the overlaid helically wrapped structure described and illustrated in detail herein simply by securing the head portion of additional microcircuit(s) and helically wrapping the tail portion(s) of the additional microcircuit(s) over the existing helically wrapped structure as the second microcircuit was helically wrapped over the first microcircuit as described herein. Accordingly, the scope of present invention is to be limited only by the terms of the following claims.

The invention claimed is:

1. A process for manufacturing a microcircuit cochlear electrode array, comprising:
   providing a metallic ribbon secured to a nonconductive film substrate;
   machining first and second flat multiconductor microcircuits from the metallic ribbon each including
      a flat elongated longitudinally extending multiconductor tail portion with longitudinally spaced outwardly exposed electrode receiving pads, and a flat multiconductor head portion connected to the tail portion and having spaced outwardly exposed attachment pads;
   laminating the first and second flat microcircuits between the film substrate and an insulating cover;
   excising the first and second laminated microcircuits from the film substrate and metallic ribbon with the electrode receiving pads;
   helically wrapping the tail portion of the excised first laminated microcircuit in a first direction with its exposed electrode receiving pads wrapped around its insulating cover;
   helically wrapping the tail portion of the excised second laminated microcircuit over and along the helically wrapped excised first laminated microcircuit in a second direction with its exposed electrode receiving pads wrapped around its insulating cover;
   mounting and electrically connecting electrodes on and to the exposed electrode receiving pads; and
   overmolding the helically wrapped tail portions with a polymeric material.

2. The process of claim 1 wherein the mounting and electrically connecting of electrodes on and to the exposed electrode receiving pads comprises mounting and electrically connecting ring electrodes to the electrode receiving pads.

3. The process of claim 2, further comprising:
   placing he ring electrodes over a wire;
   tensioning the wire;
   wrapping the tail portions of the first and second microcircuits around the tensioned wire; and
   sliding the ring electrodes over the electrode receiving pads.

4. The process of claim 3, in which electrically connecting electrodes to the exposed electrode receiving pads comprises laser welding the ring electrodes to the electrode receiving pads through an aperture in each of the ring electrodes which exposes a portion of the underlying electrode receiving pad.

5. The process of claim 1 wherein he mounting and electrical connection of electrodes, helical wrapping of the excised first and second laminated microcircuits and the overmolding with a polymeric material comprise:
   mounting and electrically connecting a reference electrode on and to a rearmost one of the exposed electrode receiving pads of the helically wrapped tail portion of the excised second microcircuit followed by a mounting and electrical connection of electrodes on and to a remainder of the exposed electrode receiving pads;
   overmolding the reference electrode and an adjacent portion of the helically wrapped excised second laminated microcircuit;
   shaping a forward portion of the helically wrapped tail portions of the excised second and first microcircuits including the remainder of the exposed electrode receiving pads and the electrodes mounted thereon and electrically connected thereto into a "J" shape; and
   overmolding the forward portion of the helically wrapped tail portions of the excised second and first microcircuits.

6. The process of claim 1 wherein:
an initial portion of the excised tail portion of first flat microcircuit adjacent the head portion thereof is helically wrapped in the first direction on a first longitudinally extending axis followed by an initial portion of the excised tail portion of the second flat microcircuit adjacent the head portion thereof being helically wrapped in the second direction on and over the helically wrapped initial portion of the tail portion of the first flat microcircuit and a first exposed electrode receiving pad of the excised tad portion comprising a reference electrode receiving pad of the second flat microcircuit is wrapped there-around;
wherein a reference electrode is mounted on and electrically connected to the reference electrode receiving pad;
wherein the overmolding of claim 1 comprises the overmolding of the initial helically wrapped portions of the first and second microcircuits and the reference electrode with a polymeric material;
wherein the helical wrapping of the tail portions of the excised first and second laminated microcircuits as set forth in claim 1 is on a second longitudinal axis parallel to and offset laterally from the first longitudinally extending axis and forms a forward end portion of the microcircuit cochlear electrode array that is laterally offset from the helically wrapped initial portions of the first and second microcircuits and includes a stylet lumen in the forward end portion along the second longitudinal axis;
wherein the forward end portion of the microcircuit electrode array is pre-formed into a inward spiral, and
wherein the overmolding of claim 1 further comprises the overmolding of the spiral shaped end portion with a polymeric material to complete a spiral-style microcircuit electrode array.

7. The process of claim 1, in which the exposed electrode receiving pads extend laterally outward at an acute angle from tail portions of the first and second multiconductor microcircuits.

8. The process of claim 7, in which the acute angle and a helical wrapping angle are selected such that the exposed electrode receiving pads are substantially perpendicular to a longitudinal axis of the helically wrapped tail portion when wrapped around the helically wrapped tail portion.

9. The process of claim 1, in which the exposed electrode receiving pads have an insulated upper surface and an exposed lower surface such that the exposed lower surface is outwardly facing and the insulated upper surface is wrapped around and contacts the insulating cover of the tail portion.

10. The process of claim 1, in which the exposed electrode receiving pads of the first laminated microcircuit adjoin the exposed electrode receiving pads of the second laminated microcircuit to form an array of exposed electrode receiving pads.

11. The process of claim 1, in which lamina the first and second flat microcircuits between the film substrate and the insulating cover comprises:
placing the insulating cover on a vacuum support apparatus;
securing the insulating cover to a frame;
placing the frame over the first and second microcircuits; and
applying heat and pressure to laminate the first and second microcircuits between the film substrate and the insulating cover.

12. The process of claim 1, in which machining first and second flat multiconductor microcircuits comprises very short pulse laser machining.

13. The process of claim 1, in which each tail portion comprising parallel electrical conductors connected to an electrode receiving pad extending laterally outward at an acute angle from an end portion of its associated electrical conductor.

14. The process of claim 13, further comprising:
attaching the laminated microcircuits to a vacuum chuck; and
exposing one side of each of the electrode receiving pads using laser ablation.

15. The process of claim 1, wherein the film substrate comprises a removable lower backing carrying an upper insulating material, the process further comprising excising each of the laminated microcircuits from the metallic ribbon and film substrate by removing the lower backing.

16. The process of claim 1, further comprising pre-forming a forward portion of the helically wrapped tail portion by:
inserting a rod into a lumen formed in the forward portion of the helically wrapped tail portion;
forming the rod and the distal portion of the helically wrapped tail portion in an inward spiral;
overcoating the helically wrapped tail portion; and
removing the rod.

17. The process of claim 1, in which:
the electrode receiving pads extend at an acute angle from longitudinally extending conductors in the first and second flat microcircuits; and
helically wrapping the tail portions comprises wrapping the tail portions at an angle such that the electrode receiving pads form a uniform band around the tail portion.

18. The process of claim 1, in which helically wrapping the tail portion of the excised first laminated microcircuit and helically wrapping the tail portion of the excised second laminated microcircuit comprises:
helically wrapping an initial portion of the tail portion of the first microcircuit adjacent its head portion on a first longitudinal axis in a first direction;
helically wrapping an initial portion of the tail portion of the second microcircuit in a direction opposite to the first direction on and along the helically wrapped initial tail portion of the first microcircuit;
overmolding the initial portions of the helically wrapped first and second microcircuits with a polymeric material;
helically wrapping a remainder of the tail portion of the first microcircuit in the first direction on a second longitudinal axis offset laterally from the first longitudinal axis with its exposed electrode receiving pads extending around its insulating cover as a first series of separate longitudinally spaced laterally extending exposed ring electrode receiving pads;
helically wrapping a remainder of the tail portion of the second microcircuit in the direction opposite to the first direction on and along the helically wrapped remainder of the first microcircuit with its exposed electrode receiving pads extending around its insulating cover and the helically wrapped remainder of the tail portion of the first microcircuit and the second longitudinal axis offset laterally from the first longitudinal axis as a second series of separate longitudinally spaced laterally extending exposed ring electrode receiving pads immediately adjacent the first series of electrode receiving pads.

* * * * *

UNITED STATES PATENT AND TRADEMARK OFFICE
CERTIFICATE OF CORRECTION

PATENT NO.        : 8,332,052 B1  
APPLICATION NO.   : 12/727160  
DATED             : December 11, 2012  
INVENTOR(S)       : William G. Orinski Page 1 of 1

It is certified that error appears in the above-identified patent and that said Letters Patent is hereby corrected as shown below:

Column 26, Line 37, Claim 3, change "placing he ring electrodes over a wire" to
-- "placing the ring electrodes over a wire"

Column 26, Line 48, Claim 5, change "The process of claim 1 where in he mounting" to
-- "The process of claim 1 where in the mounting"

Column 27, Line 12, Claim 6, change "excised tad portion comprising" to
-- "excised tail portion comprising"

Column 27, Line 57, Claim 11, change "The process of claim 1, in which lamina" to
-- "The process of claim 1, in which laminating"

Signed and Sealed this  
Ninth Day of April, 2013

Teresa Stanek Rea  
*Acting Director of the United States Patent and Trademark Office*